United States Patent
Karlsson et al.

(10) Patent No.: US 11,740,237 B2
(45) Date of Patent: Aug. 29, 2023

(54) BIOMARKERS FOR DETECTING MICROBIAL INFECTION

(71) Applicants: Roger Karlsson, Mölnlycke (SE); Edward R B Moore, Västra Frölunda (SE)

(72) Inventors: Roger Karlsson, Mölnlycke (SE); Edward R B Moore, Västra Frölunda (SE)

(*) Notice: Subject to any disclaimer, the term of this patent is extended or adjusted under 35 U.S.C. 154(b) by 0 days.

(21) Appl. No.: 17/052,731

(22) PCT Filed: May 3, 2019

(86) PCT No.: PCT/EP2019/061462
§ 371 (c)(1),
(2) Date: Nov. 3, 2020

(87) PCT Pub. No.: WO2019/211477
PCT Pub. Date: Nov. 7, 2019

(65) Prior Publication Data
US 2021/0132064 A1    May 6, 2021

(30) Foreign Application Priority Data
May 4, 2018 (GB) ..................... 1807380

(51) Int. Cl.
| G01N 33/569 | (2006.01) |
| C07K 14/21 | (2006.01) |
| C07K 14/245 | (2006.01) |
| C07K 14/285 | (2006.01) |
| C07K 14/315 | (2006.01) |
| G01N 33/68 | (2006.01) |

(52) U.S. Cl.
CPC ..... *G01N 33/56944* (2013.01); *C07K 14/212* (2013.01); *C07K 14/245* (2013.01); *C07K 14/285* (2013.01); *C07K 14/3156* (2013.01); *G01N 33/6848* (2013.01); *G01N 2469/10* (2013.01)

(58) Field of Classification Search
CPC .. C07K 14/212; C07K 14/245; C07K 14/285; C07K 14/3156; G01N 2469/10; G01N 33/56944; G01N 33/6848
See application file for complete search history.

(56) References Cited

U.S. PATENT DOCUMENTS

2007/0009903 A1*  1/2007  Doucette-Stamm ..................... A61K 39/092
536/23.7

FOREIGN PATENT DOCUMENTS

| WO | 2004092209 A2 | 10/2004 |
| WO | 2007089866 A2 | 8/2007 |
| WO | 2012100233 A1 | 7/2012 |
| WO | 2014124228 A1 | 8/2014 |

OTHER PUBLICATIONS

Kuroda et al. 2001 (Whole genome sequencing of methicillin-resistant *Staphylococcus*; sequence submissions) PIR database; Lancet 357: 1225-1240; provided herein. (Year: 2001).*
Boulund et al. "Typing and Characterization of Bacteria Using Bottom-up Tandem Mass Spectrometry Proteomics" Molecular & Cellular Proteomics, 16.6:1052-1063 (2017).
International Search Report and the Written Opinion of the International Searching Authority corresponding to International Patent Application No. PCT/EP2019/061462 (23 pages) (dated Sep. 16, 2019).
"PEPperCHIP® Custom Peptide Microarrays" product information, https://www.pepperprint.com/products/pepperchipr-custom-microarrays/ (2 pages) (2021).
Tuerk et al. "Systematic Evolution of Ligands by Exponential Enrichment: RNA Ligands to Bacteriophage T4 DNA Polymerase" Science, 249(4968):505-510 (1990).

* cited by examiner

*Primary Examiner* — Mary Maille Lyons
(74) *Attorney, Agent, or Firm* — Myers Bigel, P.A.

(57) ABSTRACT

The present invention provides specific peptide biomarkers and sets of peptide biomarkers for use in methods of detecting or identifying bacterial biomarkers in a sample, wherein said bacterial biomarkers can be used to detect *Streptococcus pneumoniae, Staphylococcus aureus, Haemophilus influenzae, Escherichia coli*, and/or *Moraxella catarrhalis* in a sample. Kits and diagnostic methods are also provided.

13 Claims, 7 Drawing Sheets

Figure 1:
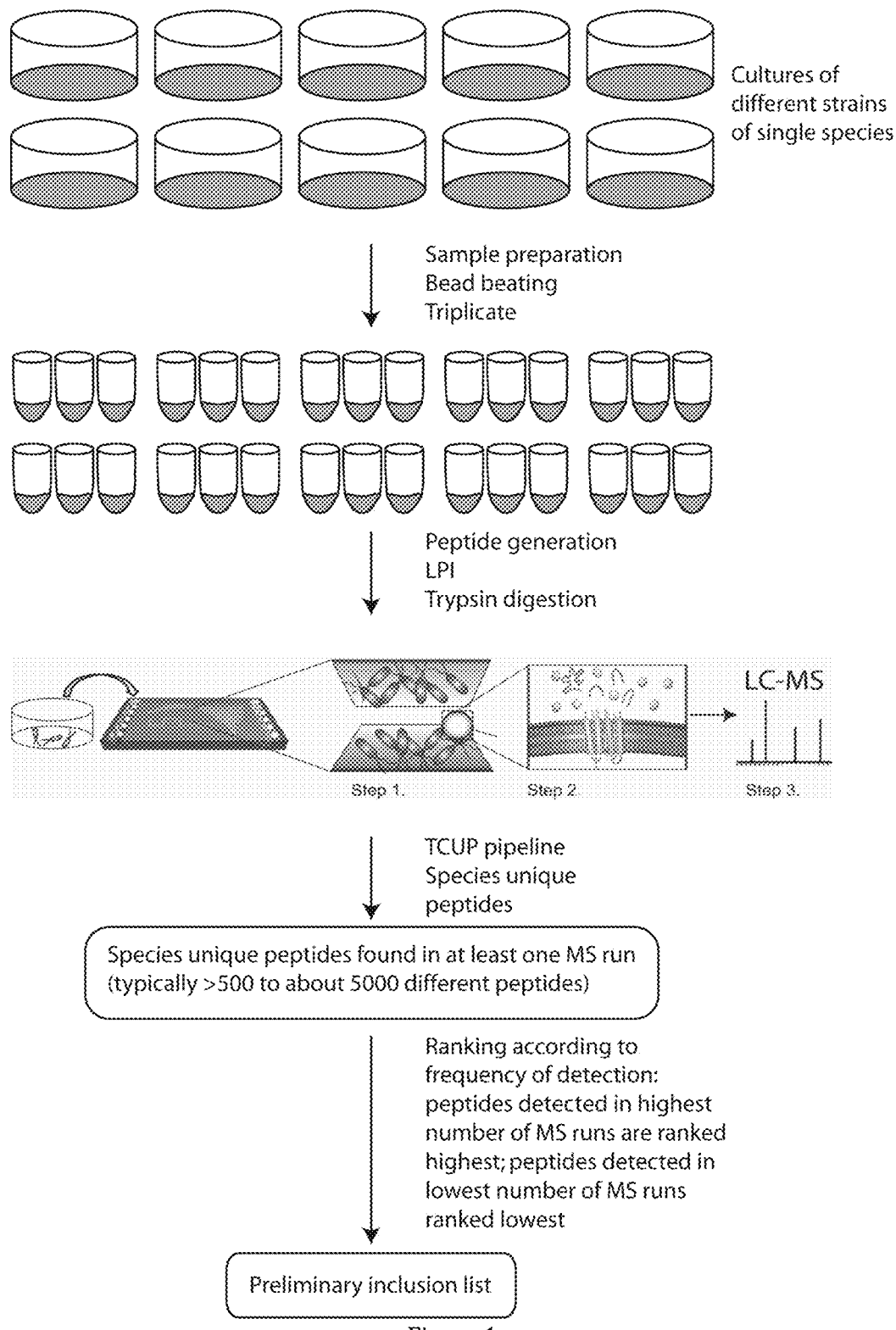

Specification includes a Sequence Listing.

```
                        SEQUENCE LISTING

<160> NUMBER OF SEQ ID NOS: 280

<210> SEQ ID NO 1
<211> LENGTH: 16
<212> TYPE: PRT
<213> ORGANISM: Staphylococcus aureus

<400> SEQUENCE: 1

Thr Val Gln Pro Ile Asp Val Asp Thr Ile Val Ala Ser Val Glu Lys
1               5                   10                  15

<210> SEQ ID NO 2
<211> LENGTH: 15
<212> TYPE: PRT
<213> ORGANISM: Staphylococcus aureus

<400> SEQUENCE: 2

Gln Ala Gly Val Gly Ala Ala Val Val Ala Glu Leu Ser Glu Arg
1               5                   10                  15

<210> SEQ ID NO 3
<211> LENGTH: 11
<212> TYPE: PRT
<213> ORGANISM: Staphylococcus aureus

<400> SEQUENCE: 3

Glu Leu Ile Asn Asn Ile Gln Ser Gly Gln Arg
1               5                   10

<210> SEQ ID NO 4
<211> LENGTH: 16
<212> TYPE: PRT
<213> ORGANISM: Staphylococcus aureus

<400> SEQUENCE: 4

Leu Gly Ile Ser Asp Gly Asp Val Glu Glu Thr Glu Asp Ala Pro Lys
1               5                   10                  15

<210> SEQ ID NO 5
<211> LENGTH: 16
<212> TYPE: PRT
<213> ORGANISM: Staphylococcus aureus

<400> SEQUENCE: 5
```

```
Ala Leu Leu Asn Asn Met Val Gln Gly Val Ser Gln Gly Tyr Val Lys
1               5                   10                  15
```

<210> SEQ ID NO 6
<211> LENGTH: 17
<212> TYPE: PRT
<213> ORGANISM: Staphylococcus aureus

<400> SEQUENCE: 6

```
Ser Asn Val Asn Asp Ala Thr Asp Tyr Ser Ser Glu Thr Pro Glu Gly
1               5                   10                  15

Lys
```

<210> SEQ ID NO 7
<211> LENGTH: 15
<212> TYPE: PRT
<213> ORGANISM: Staphylococcus aureus

<400> SEQUENCE: 7

```
Ala Asn Asn Val Ala Thr Asp Ala Asn His Ser Tyr Thr Ser Arg
1               5                   10                  15
```

<210> SEQ ID NO 8
<211> LENGTH: 15
<212> TYPE: PRT
<213> ORGANISM: Staphylococcus aureus

<400> SEQUENCE: 8

```
Ile Leu Ala Glu Ser Pro Asn Leu Ala Ile Ser Ser Ser Ser Arg
1               5                   10                  15
```

<210> SEQ ID NO 9
<211> LENGTH: 14
<212> TYPE: PRT
<213> ORGANISM: Staphylococcus aureus

<400> SEQUENCE: 9

```
Asn Val Val Glu Ile Pro Leu Asn Asp Glu Glu Gln Ser Lys
1               5                   10
```

<210> SEQ ID NO 10
<211> LENGTH: 29
<212> TYPE: PRT
<213> ORGANISM: Staphylococcus aureus

<400> SEQUENCE: 10

```
Ala Thr Glu Ala Thr Asn Ala Thr Asn Asn Gln Ser Thr Gln Val Ser
1               5                   10                  15

Gln Ala Thr Ser Gln Pro Ile Asn Phe Gln Val Gln Lys
            20                  25
```

<210> SEQ ID NO 11
<211> LENGTH: 16
<212> TYPE: PRT
<213> ORGANISM: Staphylococcus aureus

<400> SEQUENCE: 11

```
Ile His Leu Val Gly Asp Glu Ile Ala Asn Gly Gln Gly Ile Gly Arg
1               5                   10                  15
```

<210> SEQ ID NO 12
<211> LENGTH: 16
<212> TYPE: PRT

<213> ORGANISM: Staphylococcus aureus

<400> SEQUENCE: 12

Asn Ile Ser Asn Asn Val Leu Val Thr Ile Asp Ala Ala Gln Gly Lys
1               5                   10                  15

<210> SEQ ID NO 13
<211> LENGTH: 16
<212> TYPE: PRT
<213> ORGANISM: Staphylococcus aureus

<400> SEQUENCE: 13

Thr Ala Lys Pro Val Ala Glu Val Glu Ser Gln Thr Glu Val Thr Glu
1               5                   10                  15

<210> SEQ ID NO 14
<211> LENGTH: 15
<212> TYPE: PRT
<213> ORGANISM: Staphylococcus aureus

<400> SEQUENCE: 14

Ser Gln Gly Val Ser Glu Glu Leu Asn Glu Ser Ile Asp Arg
1               5                   10                  15

<210> SEQ ID NO 15
<211> LENGTH: 18
<212> TYPE: PRT
<213> ORGANISM: Staphylococcus aureus

<400> SEQUENCE: 15

Ala Glu Glu Asn Gly Leu Thr Val Val Asp Ala Phe Asn Phe Glu Ala
1               5                   10                  15

Pro Lys

<210> SEQ ID NO 16
<211> LENGTH: 19
<212> TYPE: PRT
<213> ORGANISM: Staphylococcus aureus

<400> SEQUENCE: 16

Glu Lys Ala Asn Glu Leu Leu Lys Asp Asn Ala Glu Leu Ile Ala Ser
1               5                   10                  15

Phe Ser Arg

<210> SEQ ID NO 17
<211> LENGTH: 18
<212> TYPE: PRT
<213> ORGANISM: Staphylococcus aureus

<400> SEQUENCE: 17

Leu Leu Gly Ile Asn Ala Thr Ile Val Met Pro Glu Thr Ala Pro Gln
1               5                   10                  15

Ala Lys

<210> SEQ ID NO 18
<211> LENGTH: 12
<212> TYPE: PRT
<213> ORGANISM: Moraxella catarrhalis

<400> SEQUENCE: 18

Val Val Leu Ala Gly Asp Thr Val Val Ser Asp Arg
1               5                   10

<210> SEQ ID NO 19
<211> LENGTH: 18
<212> TYPE: PRT
<213> ORGANISM: Moraxella catarrhalis

<400> SEQUENCE: 19

Gln Ile Val Ser Asn Ala Gly Asp Glu Ala Ser Val Ile Val Asn Glu
1               5                   10                  15

Val Lys

<210> SEQ ID NO 20
<211> LENGTH: 22
<212> TYPE: PRT
<213> ORGANISM: Moraxella catarrhalis

<400> SEQUENCE: 20

Ala Ile Ala Gln Val Gly Ser Ile Ser Ala Asn Ser Asp Ala Thr Ile
1               5                   10                  15

Gly Glu Leu Ile Ser Lys
            20

<210> SEQ ID NO 21
<211> LENGTH: 12
<212> TYPE: PRT
<213> ORGANISM: Moraxella catarrhalis

<400> SEQUENCE: 21

Glu Leu Ser Asn Thr Ala Ala Glu Thr Gln Pro Lys
1               5                   10

<210> SEQ ID NO 22
<211> LENGTH: 12
<212> TYPE: PRT
<213> ORGANISM: Moraxella catarrhalis

<400> SEQUENCE: 22

Val Asp Ala Thr Val Asp Ala Gln Asn Pro Thr Lys
1               5                   10

<210> SEQ ID NO 23
<211> LENGTH: 10
<212> TYPE: PRT
<213> ORGANISM: Moraxella catarrhalis

<400> SEQUENCE: 23

Gln Ser Asp Val Gly Gln Leu Thr Gly Lys
1               5                   10

<210> SEQ ID NO 24
<211> LENGTH: 13
<212> TYPE: PRT
<213> ORGANISM: Moraxella catarrhalis

<400> SEQUENCE: 24

Phe Asn Ala Thr Ala Ala Leu Gly Gly Tyr Gly Ser Lys
1               5                   10

<210> SEQ ID NO 25
<211> LENGTH: 17
<212> TYPE: PRT
<213> ORGANISM: Moraxella catarrhalis

<400> SEQUENCE: 25

Thr His Thr Ser Ala Leu Ala Glu Glu Asn Gln Gln Ala Ser Ile Pro
1               5                   10                  15

Arg

<210> SEQ ID NO 26
<211> LENGTH: 19
<212> TYPE: PRT
<213> ORGANISM: Moraxella catarrhalis

<400> SEQUENCE: 26

Tyr Val Val Glu Gly Ala Asn Met Pro Leu Asp Ala Gln Ala Ile Asp
1               5                   10                  15

Ile Val Arg

<210> SEQ ID NO 27
<211> LENGTH: 14
<212> TYPE: PRT
<213> ORGANISM: Moraxella catarrhalis

<400> SEQUENCE: 27

Ser Gln Ile Tyr Gln Thr Thr Ala Ser Val Ser Gly Ala Arg
1               5                   10

<210> SEQ ID NO 28
<211> LENGTH: 12
<212> TYPE: PRT
<213> ORGANISM: Moraxella catarrhalis

<400> SEQUENCE: 28

Leu Leu Asn Glu Thr Thr Gly Gln Val Val Pro Lys
1               5                   10

<210> SEQ ID NO 29
<211> LENGTH: 11
<212> TYPE: PRT
<213> ORGANISM: Moraxella catarrhalis

<400> SEQUENCE: 29

Ser Ser Glu Asn Val Val Val Ser Val Arg
1               5                   10

<210> SEQ ID NO 30
<211> LENGTH: 17
<212> TYPE: PRT
<213> ORGANISM: Moraxella catarrhalis

<400> SEQUENCE: 30

Ala Ile Ser Tyr Gly Asn Ser Ala Asp Ala Gln Pro Tyr Val Gly Ala
1               5                   10                  15

Lys

<210> SEQ ID NO 31
<211> LENGTH: 22
<212> TYPE: PRT
<213> ORGANISM: Moraxella catarrhalis

<400> SEQUENCE: 31

Gly Leu Pro Val Ser Asn Ser Gly Ala Pro Ile Ser Val Pro Val Gly
1               5                   10                  15

Gln Ala Thr Leu Gly Arg
                20

-continued

```
<210> SEQ ID NO 32
<211> LENGTH: 17
<212> TYPE: PRT
<213> ORGANISM: Moraxella catarrhalis

<400> SEQUENCE: 32

Val Asn Tyr Asn Gly Asp Thr Asp Thr Val Thr Leu Ser Gly Val Ala
1               5                   10                  15

Lys

<210> SEQ ID NO 33
<211> LENGTH: 16
<212> TYPE: PRT
<213> ORGANISM: Moraxella catarrhalis

<400> SEQUENCE: 33

Ala Val Ala Thr Gln Gln Ala Thr Val Ser Ala Glu Tyr Leu Gln Lys
1               5                   10                  15

<210> SEQ ID NO 34
<211> LENGTH: 15
<212> TYPE: PRT
<213> ORGANISM: Moraxella catarrhalis

<400> SEQUENCE: 34

Ala Asp Ser Gly Leu Ser Glu Ser Glu Ile Glu Glu Met Ile Arg
1               5                   10                  15

<210> SEQ ID NO 35
<211> LENGTH: 13
<212> TYPE: PRT
<213> ORGANISM: Moraxella catarrhalis

<400> SEQUENCE: 35

Leu Gly Ala Gln Glu Ala Glu Leu Val Ser Asn Ser Lys
1               5                   10

<210> SEQ ID NO 36
<211> LENGTH: 14
<212> TYPE: PRT
<213> ORGANISM: Haemophilus influenzae

<400> SEQUENCE: 36

Gly Val Ala Ala Asp Ala Ile Ser Ala Thr Gly Tyr Gly Lys
1               5                   10

<210> SEQ ID NO 37
<211> LENGTH: 22
<212> TYPE: PRT
<213> ORGANISM: Haemophilus influenzae

<400> SEQUENCE: 37

Ala Asn Leu Lys Pro Gln Ala Gln Ala Thr Leu Asp Ser Ile Tyr Gly
1               5                   10                  15

Glu Met Ser Gln Val Lys
            20

<210> SEQ ID NO 38
<211> LENGTH: 11
<212> TYPE: PRT
<213> ORGANISM: Haemophilus influenzae

<400> SEQUENCE: 38

Ala Asp Ser Val Ala Asn Tyr Phe Val Ala Lys
```

<210> SEQ ID NO 39
<211> LENGTH: 14
<212> TYPE: PRT
<213> ORGANISM: Haemophilus influenzae

<400> SEQUENCE: 39

Gly Ser Tyr Glu Val Leu Asp Gly Leu Asp Val Tyr Gly Lys
1               5                   10

<210> SEQ ID NO 40
<211> LENGTH: 16
<212> TYPE: PRT
<213> ORGANISM: Haemophilus influenzae

<400> SEQUENCE: 40

Leu Ser Gln Glu Arg Ala Asp Ser Val Ala Asn Tyr Phe Val Ala Lys
1               5                   10                  15

<210> SEQ ID NO 41
<211> LENGTH: 16
<212> TYPE: PRT
<213> ORGANISM: Haemophilus influenzae

<400> SEQUENCE: 41

Ala Val Val Tyr Asn Asn Glu Gly Thr Asn Val Glu Leu Gly Gly Arg
1               5                   10                  15

<210> SEQ ID NO 42
<211> LENGTH: 14
<212> TYPE: PRT
<213> ORGANISM: Haemophilus influenzae

<400> SEQUENCE: 42

Tyr Asp Ala Asn Asn Ile Ile Ala Gly Ile Ala Tyr Gly Arg
1               5                   10

<210> SEQ ID NO 43
<211> LENGTH: 18
<212> TYPE: PRT
<213> ORGANISM: Haemophilus influenzae

<400> SEQUENCE: 43

Ala Thr His Asn Phe Gly Asp Gly Phe Tyr Ala Gln Gly Tyr Leu Glu
1               5                   10                  15

Thr Arg

<210> SEQ ID NO 44
<211> LENGTH: 16
<212> TYPE: PRT
<213> ORGANISM: Haemophilus influenzae

<400> SEQUENCE: 44

Ala Val Val Tyr Asn Asn Glu Gly Thr Lys Val Glu Leu Gly Gly Arg
1               5                   10                  15

<210> SEQ ID NO 45
<211> LENGTH: 13
<212> TYPE: PRT
<213> ORGANISM: Haemophilus influenzae

<400> SEQUENCE: 45

Gln Gln Val Asn Gly Ala Leu Ser Thr Leu Gly Tyr Arg
1               5                   10

```
1               5               10
```

<210> SEQ ID NO 46
<211> LENGTH: 14
<212> TYPE: PRT
<213> ORGANISM: Haemophilus influenzae

<400> SEQUENCE: 46

```
Tyr Val Pro Thr Asn Gly Asn Thr Val Gly Tyr Thr Phe Lys
1               5                   10
```

<210> SEQ ID NO 47
<211> LENGTH: 12
<212> TYPE: PRT
<213> ORGANISM: Haemophilus influenzae

<400> SEQUENCE: 47

```
Leu Ser Val Ile Ala Glu Gln Ser Asn Ser Thr Arg
1               5                   10
```

<210> SEQ ID NO 48
<211> LENGTH: 17
<212> TYPE: PRT
<213> ORGANISM: Haemophilus influenzae

<400> SEQUENCE: 48

```
Ser Ala Asp Leu Thr Asn Glu Val Ala Val Gly Asp Val Val Glu Ala
1               5                   10                  15
Lys
```

<210> SEQ ID NO 49
<211> LENGTH: 17
<212> TYPE: PRT
<213> ORGANISM: Haemophilus influenzae

<400> SEQUENCE: 49

```
Ser Ala Asp Leu Thr Ser Glu Val Ala Val Gly Asp Val Val Glu Ala
1               5                   10                  15
Lys
```

<210> SEQ ID NO 50
<211> LENGTH: 15
<212> TYPE: PRT
<213> ORGANISM: Haemophilus influenzae

<400> SEQUENCE: 50

```
Thr Ser Pro Thr Gln Asn Leu Ser Leu Asp Ala Phe Val Ala Arg
1               5                   10                  15
```

<210> SEQ ID NO 51
<211> LENGTH: 13
<212> TYPE: PRT
<213> ORGANISM: Haemophilus influenzae

<400> SEQUENCE: 51

```
Ala Gln Tyr Ile Val Glu Gln Val Ile Gly Gln Ala Arg
1               5                   10
```

<210> SEQ ID NO 52
<211> LENGTH: 18
<212> TYPE: PRT
<213> ORGANISM: Streptococcus pneumoniae

<400> SEQUENCE: 52

```
Val Ser Asp Val Ala Glu Ser Thr Gly Glu Phe Thr Ser Glu Gln Phe
1               5                   10                  15

Glu Lys

<210> SEQ ID NO 53
<211> LENGTH: 13
<212> TYPE: PRT
<213> ORGANISM: Streptococcus pneumoniae

<400> SEQUENCE: 53

Gly Ala Ala Asn Gly Val Val Ser His Glu Asn Thr Arg
1               5                   10

<210> SEQ ID NO 54
<211> LENGTH: 10
<212> TYPE: PRT
<213> ORGANISM: Streptococcus pneumoniae

<400> SEQUENCE: 54

Glu Glu Ala Pro Val Ala Ser Gln Ser Lys
1               5                   10

<210> SEQ ID NO 55
<211> LENGTH: 12
<212> TYPE: PRT
<213> ORGANISM: Streptococcus pneumoniae

<400> SEQUENCE: 55

Ser Ala Asp Gln Gln Ala Glu Glu Asp Tyr Ala Arg
1               5                   10

<210> SEQ ID NO 56
<211> LENGTH: 10
<212> TYPE: PRT
<213> ORGANISM: Streptococcus pneumoniae

<400> SEQUENCE: 56

Ala Pro Leu Gln Ser Glu Leu Asp Thr Lys
1               5                   10

<210> SEQ ID NO 57
<211> LENGTH: 14
<212> TYPE: PRT
<213> ORGANISM: Streptococcus pneumoniae

<400> SEQUENCE: 57

Leu Lys Glu Ile Asp Glu Ser Asp Ser Glu Asp Tyr Val Lys
1               5                   10

<210> SEQ ID NO 58
<211> LENGTH: 14
<212> TYPE: PRT
<213> ORGANISM: Streptococcus pneumoniae

<400> SEQUENCE: 58

Ala Lys Leu Glu Glu Ala Glu Lys Lys Ala Thr Glu Ala Lys
1               5                   10

<210> SEQ ID NO 59
<211> LENGTH: 20
<212> TYPE: PRT
<213> ORGANISM: Streptococcus pneumoniae

<400> SEQUENCE: 59
```

```
Ala Val Asn Glu Pro Glu Lys Pro Ala Glu Glu Ser Glu Asn Pro Ala
1               5                   10                  15

Pro Ala Pro Lys
            20

<210> SEQ ID NO 60
<211> LENGTH: 14
<212> TYPE: PRT
<213> ORGANISM: Streptococcus pneumoniae

<400> SEQUENCE: 60

Asn Val Glu Ile Ile Glu Asp Asp Lys Gln Gly Val Ile Arg
1               5                   10

<210> SEQ ID NO 61
<211> LENGTH: 18
<212> TYPE: PRT
<213> ORGANISM: Streptococcus pneumoniae

<400> SEQUENCE: 61

Asn Leu Pro Val Gly Ser Asp Gly Thr Phe Thr Pro Glu Asp Tyr Val
1               5                   10                  15

Gly Arg

<210> SEQ ID NO 62
<211> LENGTH: 12
<212> TYPE: PRT
<213> ORGANISM: Streptococcus pneumoniae

<400> SEQUENCE: 62

Thr Leu Glu Leu Glu Ile Ala Glu Ser Asp Val Lys
1               5                   10

<210> SEQ ID NO 63
<211> LENGTH: 17
<212> TYPE: PRT
<213> ORGANISM: Streptococcus pneumoniae

<400> SEQUENCE: 63

Asp Ile Gly Leu Ala Asn Asp Gly Ser Ile Val Gly Ile Asn Tyr Ala
1               5                   10                  15

Lys

<210> SEQ ID NO 64
<211> LENGTH: 10
<212> TYPE: PRT
<213> ORGANISM: Streptococcus pneumoniae

<400> SEQUENCE: 64

Ile Ala Glu Leu Glu Tyr Glu Val Gln Arg
1               5                   10

<210> SEQ ID NO 65
<211> LENGTH: 14
<212> TYPE: PRT
<213> ORGANISM: Streptococcus pneumoniae

<400> SEQUENCE: 65

Ala Val Ala Ala Ala Asp Ala Ala Asp Ala Gly Ala Ala Lys
1               5                   10

<210> SEQ ID NO 66
```

```
<211> LENGTH: 17
<212> TYPE: PRT
<213> ORGANISM: Streptococcus pneumoniae

<400> SEQUENCE: 66

Gly Gln Asp Trp Val Ile Ala Ala Glu Val Val Thr Lys Pro Glu Val
1               5                   10                  15
Lys

<210> SEQ ID NO 67
<211> LENGTH: 17
<212> TYPE: PRT
<213> ORGANISM: Streptococcus pneumoniae

<400> SEQUENCE: 67

Thr Leu Ser Pro Glu Glu Tyr Ala Val Thr Gln Glu Asn Gln Thr Glu
1               5                   10                  15
Arg

<210> SEQ ID NO 68
<211> LENGTH: 12
<212> TYPE: PRT
<213> ORGANISM: Streptococcus pneumoniae

<400> SEQUENCE: 68

Lys Asp Glu Ala Glu Ala Ala Phe Ala Thr Ile Arg
1               5                   10

<210> SEQ ID NO 69
<211> LENGTH: 18
<212> TYPE: PRT
<213> ORGANISM: Streptococcus pneumoniae

<400> SEQUENCE: 69

Ser Gln Pro Ser Ser Glu Thr Glu Leu Ser Gly Asn Lys Gln Glu Gln
1               5                   10                  15
Glu Arg

<210> SEQ ID NO 70
<211> LENGTH: 16
<212> TYPE: PRT
<213> ORGANISM: Streptococcus pneumoniae

<400> SEQUENCE: 70

Ile Gly Val Ile Ser Val Val Glu Asp Gly Asp Glu Ala Leu Ala Lys
1               5                   10                  15

<210> SEQ ID NO 71
<211> LENGTH: 14
<212> TYPE: PRT
<213> ORGANISM: Streptococcus pneumoniae

<400> SEQUENCE: 71

Val Ala Tyr Phe Asn Glu Ile Asp Thr Tyr Ser Glu Val Lys
1               5                   10

<210> SEQ ID NO 72
<211> LENGTH: 13
<212> TYPE: PRT
<213> ORGANISM: Moraxella catarrhalis

<400> SEQUENCE: 72

Ala Gln Tyr Asp Ile Thr Gln Asn Ala Gly Thr Glu Arg
```

-continued

```
<210> SEQ ID NO 73
<211> LENGTH: 26
<212> TYPE: PRT
<213> ORGANISM: Moraxella catarrhalis

<400> SEQUENCE: 73

Thr Phe His Val Gly Gly Ala Ala Ser Ala Ala Ser Val Asp Asn Ser
1               5                   10                  15

Val Ser Val Gly Asn Ala Gly Ser Val Arg
            20                  25

<210> SEQ ID NO 74
<211> LENGTH: 11
<212> TYPE: PRT
<213> ORGANISM: Moraxella catarrhalis

<400> SEQUENCE: 74

Ala Asn Leu Asp Thr Ser Thr Glu Glu Ala Arg
1               5                   10

<210> SEQ ID NO 75
<211> LENGTH: 11
<212> TYPE: PRT
<213> ORGANISM: Moraxella catarrhalis

<400> SEQUENCE: 75

Ala Ser Ser Glu Asn Thr Gln Asn Ile Ala Lys
1               5                   10

<210> SEQ ID NO 76
<211> LENGTH: 13
<212> TYPE: PRT
<213> ORGANISM: Moraxella catarrhalis

<400> SEQUENCE: 76

Asp Ala Asp Ala Val Glu Ala Gly Gln Val Ile Ala Lys
1               5                   10

<210> SEQ ID NO 77
<211> LENGTH: 10
<212> TYPE: PRT
<213> ORGANISM: Moraxella catarrhalis

<400> SEQUENCE: 77

Phe Ala Ala Thr Ala Asp Ala Ile Thr Lys
1               5                   10

<210> SEQ ID NO 78
<211> LENGTH: 21
<212> TYPE: PRT
<213> ORGANISM: Moraxella catarrhalis

<400> SEQUENCE: 78

Leu Asn Thr Gln Gly Ala Ser Phe Asp Tyr Pro Val Ala Ser Asn Ala
1               5                   10                  15

Thr Glu Gln Gly Arg
            20

<210> SEQ ID NO 79
<211> LENGTH: 14
<212> TYPE: PRT
<213> ORGANISM: Moraxella catarrhalis
```

<400> SEQUENCE: 79

Asn Lys Ala Asp Ala Asp Ala Ser Phe Glu Thr Leu Thr Lys
1               5                   10

<210> SEQ ID NO 80
<211> LENGTH: 13
<212> TYPE: PRT
<213> ORGANISM: Moraxella catarrhalis

<400> SEQUENCE: 80

Ala Lys Leu Glu Ser Leu Thr Glu Asp Met Val Ala Arg
1               5                   10

<210> SEQ ID NO 81
<211> LENGTH: 21
<212> TYPE: PRT
<213> ORGANISM: Moraxella catarrhalis

<400> SEQUENCE: 81

Ile Ile Thr Asn Asn His Ala Ile Ala Leu Asn Leu Ala Ala Glu Gly
1               5                   10                  15

Tyr Gly Ile Ala Lys
            20

<210> SEQ ID NO 82
<211> LENGTH: 19
<212> TYPE: PRT
<213> ORGANISM: Moraxella catarrhalis

<400> SEQUENCE: 82

Ile Leu Ala Asp Ile Ala Met His Asp Ala Ala Ala Phe Thr Ala Ile
1               5                   10                  15

Thr Glu Lys

<210> SEQ ID NO 83
<211> LENGTH: 18
<212> TYPE: PRT
<213> ORGANISM: Moraxella catarrhalis

<400> SEQUENCE: 83

Ile Tyr Arg Pro Glu Ile Tyr Asn Ala Asn Ser Val Ala Gly Gln Ile
1               5                   10                  15

Tyr Lys

<210> SEQ ID NO 84
<211> LENGTH: 11
<212> TYPE: PRT
<213> ORGANISM: Moraxella catarrhalis

<400> SEQUENCE: 84

Leu Asp Ile Thr Glu Thr Thr Asp Asp Ser Arg
1               5                   10

<210> SEQ ID NO 85
<211> LENGTH: 16
<212> TYPE: PRT
<213> ORGANISM: Moraxella catarrhalis

<400> SEQUENCE: 85

Ala Leu Glu Ser Asn Val Glu Glu Gly Leu Leu Asp Leu Ser Gly Arg
1               5                   10                  15

<210> SEQ ID NO 86
<211> LENGTH: 13
<212> TYPE: PRT
<213> ORGANISM: Moraxella catarrhalis

<400> SEQUENCE: 86

Glu Phe Tyr Ala Ala Glu Thr Leu Pro Ala Glu Ser Arg
1               5                   10

<210> SEQ ID NO 87
<211> LENGTH: 15
<212> TYPE: PRT
<213> ORGANISM: Moraxella catarrhalis

<400> SEQUENCE: 87

Met Asn Ile Glu Gln Thr Leu Gln Ser Ala Glu Asp Thr Ala Arg
1               5                   10                  15

<210> SEQ ID NO 88
<211> LENGTH: 11
<212> TYPE: PRT
<213> ORGANISM: Moraxella catarrhalis

<400> SEQUENCE: 88

Gln Asp Pro Ala Asn Gln Glu Val Tyr Thr Lys
1               5                   10

<210> SEQ ID NO 89
<211> LENGTH: 15
<212> TYPE: PRT
<213> ORGANISM: Moraxella catarrhalis

<400> SEQUENCE: 89

Ser Val Thr Ala Thr Asp Asn Thr Thr Gln Ala Thr Val Ile Lys
1               5                   10                  15

<210> SEQ ID NO 90
<211> LENGTH: 20
<212> TYPE: PRT
<213> ORGANISM: Moraxella catarrhalis

<400> SEQUENCE: 90

Val Gly Val Met Ala Gly Pro Glu Gln Ala Val Ala Glu Val Ala Gly
1               5                   10                  15

Gln Val Ala Lys
            20

<210> SEQ ID NO 91
<211> LENGTH: 24
<212> TYPE: PRT
<213> ORGANISM: Moraxella catarrhalis

<400> SEQUENCE: 91

Ala His Ile Gly Leu Ala Gln Ala Gln Phe Pro Glu Gly Leu Ala Ser
1               5                   10                  15

Ser Gln Val Asp Ala Leu Ala Arg
            20

<210> SEQ ID NO 92
<211> LENGTH: 18
<212> TYPE: PRT
<213> ORGANISM: Moraxella catarrhalis

<400> SEQUENCE: 92

```
Ala Leu Ala Thr Asp Tyr Ser His Val Val Ala Pro Ala Thr Thr Thr
1               5                   10                  15

Gly Lys
```

<210> SEQ ID NO 93
<211> LENGTH: 18
<212> TYPE: PRT
<213> ORGANISM: Moraxella catarrhalis

<400> SEQUENCE: 93

```
Glu Asn Thr Val Ile Val Asp Gly Ala Gly Asp Lys Ala Ser Ile Glu
1               5                   10                  15

Ala Arg
```

<210> SEQ ID NO 94
<211> LENGTH: 21
<212> TYPE: PRT
<213> ORGANISM: Moraxella catarrhalis

<400> SEQUENCE: 94

```
Leu Pro Val Asp Lys Glu Thr Ala Pro Ser Asp Asp Ala Thr Ala Thr
1               5                   10                  15

Thr Gln Phe Ser Arg
            20
```

<210> SEQ ID NO 95
<211> LENGTH: 14
<212> TYPE: PRT
<213> ORGANISM: Moraxella catarrhalis

<400> SEQUENCE: 95

```
Leu Thr Tyr Thr Asp Gly Ser Asp Pro Gly Ser Tyr Tyr Arg
1               5                   10
```

<210> SEQ ID NO 96
<211> LENGTH: 26
<212> TYPE: PRT
<213> ORGANISM: Moraxella catarrhalis

<400> SEQUENCE: 96

```
Asn Leu Gly Ala Ala Val Asn Glu Val Thr Ala Asn Glu Gln Ser Ala
1               5                   10                  15

Glu Ala Lys Ala Pro Glu Asp Gln Gln Tyr
            20                  25
```

<210> SEQ ID NO 97
<211> LENGTH: 12
<212> TYPE: PRT
<213> ORGANISM: Moraxella catarrhalis

<400> SEQUENCE: 97

```
Ser Asp Ala Leu Tyr Val Val Glu Asp Ser Val Lys
1               5                   10
```

<210> SEQ ID NO 98
<211> LENGTH: 10
<212> TYPE: PRT
<213> ORGANISM: Moraxella catarrhalis

<400> SEQUENCE: 98

```
Leu Ala Asp Glu Gly Asp Ile Asp Val Arg
1               5                   10
```

<210> SEQ ID NO 99
<211> LENGTH: 14
<212> TYPE: PRT
<213> ORGANISM: Moraxella catarrhalis

<400> SEQUENCE: 99

Leu Thr Gln Ala Thr Ala Gln Ala Ser Ala Pro Gln Gly Arg
1               5                   10

<210> SEQ ID NO 100
<211> LENGTH: 14
<212> TYPE: PRT
<213> ORGANISM: Moraxella catarrhalis

<400> SEQUENCE: 100

Leu Tyr Pro Asn Asp Pro Thr Tyr Gln Ala Ala Ser Glu Lys
1               5                   10

<210> SEQ ID NO 101
<211> LENGTH: 27
<212> TYPE: PRT
<213> ORGANISM: Moraxella catarrhalis

<400> SEQUENCE: 101

Asn Gln Ala Asp Ile Ala Asn Asn Ile Asn Asn Ile Tyr Glu Leu Ala
1               5                   10                  15

Gln Gln Gln Asp Gln His Ser Ser Asp Ile Lys
            20                  25

<210> SEQ ID NO 102
<211> LENGTH: 18
<212> TYPE: PRT
<213> ORGANISM: Moraxella catarrhalis

<400> SEQUENCE: 102

Ser Glu Val Leu Asp Gly Met Asn Ser Ala Tyr Asn Pro Val Val Glu
1               5                   10                  15

Asp Lys

<210> SEQ ID NO 103
<211> LENGTH: 13
<212> TYPE: PRT
<213> ORGANISM: Moraxella catarrhalis

<400> SEQUENCE: 103

Ser Leu Glu Asn Asp Leu Gly Val Ser Leu Leu His Arg
1               5                   10

<210> SEQ ID NO 104
<211> LENGTH: 13
<212> TYPE: PRT
<213> ORGANISM: Haemophilus influenzae

<400> SEQUENCE: 104

Phe Gly Gly Asn Ala Gln Gln Thr Ala Gln Leu Pro Arg
1               5                   10

<210> SEQ ID NO 105
<211> LENGTH: 17
<212> TYPE: PRT
<213> ORGANISM: Haemophilus influenzae

<400> SEQUENCE: 105

Gly Leu Ser Val Gly Asp Gln Ile Gln Ala Gly Ile Asn Ser Pro Ile
1               5                   10                  15

Lys

<210> SEQ ID NO 106
<211> LENGTH: 16
<212> TYPE: PRT
<213> ORGANISM: Haemophilus influenzae

<400> SEQUENCE: 106

Ala Thr Gly Glu Ile Asn Leu Asp Gly Glu Asn Leu Leu Thr Thr Lys
1               5                   10                  15

<210> SEQ ID NO 107
<211> LENGTH: 18
<212> TYPE: PRT
<213> ORGANISM: Haemophilus influenzae

<400> SEQUENCE: 107

Ala Thr His Asn Leu Gly Asp Gly Phe Tyr Ala Gln Gly Tyr Leu Glu
1               5                   10                  15

Thr Arg

<210> SEQ ID NO 108
<211> LENGTH: 16
<212> TYPE: PRT
<213> ORGANISM: Haemophilus influenzae

<400> SEQUENCE: 108

Gly Ile Ala Ser Gly Thr Glu Val Ser Phe Gly Thr Tyr Gly Leu Lys
1               5                   10                  15

<210> SEQ ID NO 109
<211> LENGTH: 13
<212> TYPE: PRT
<213> ORGANISM: Haemophilus influenzae

<400> SEQUENCE: 109

Gly Val Ala Ala Ile Val Thr Leu Ser Ser Thr Gly Arg
1               5                   10

<210> SEQ ID NO 110
<211> LENGTH: 12
<212> TYPE: PRT
<213> ORGANISM: Haemophilus influenzae

<400> SEQUENCE: 110

Asn Asn Glu Gly Thr Asn Val Glu Leu Gly Gly Arg
1               5                   10

<210> SEQ ID NO 111
<211> LENGTH: 18
<212> TYPE: PRT
<213> ORGANISM: Haemophilus influenzae

<400> SEQUENCE: 111

Thr Ile Ser Asp Gly Ile Thr Ser Ala Glu Asp Lys Glu Tyr Gly Val
1               5                   10                  15

Leu Lys

<210> SEQ ID NO 112
<211> LENGTH: 14

<212> TYPE: PRT
<213> ORGANISM: Haemophilus influenzae

<400> SEQUENCE: 112

Ala Ile Leu Pro Pro Gln Glu Ile Glu Gln Gly Thr Val Lys
1               5                   10

<210> SEQ ID NO 113
<211> LENGTH: 17
<212> TYPE: PRT
<213> ORGANISM: Haemophilus influenzae

<400> SEQUENCE: 113

Ala Thr Asn Leu Ser Ala Glu Gln Leu Asn Val Thr Asp Ala Ser Glu
1               5                   10                  15

Lys

<210> SEQ ID NO 114
<211> LENGTH: 22
<212> TYPE: PRT
<213> ORGANISM: Haemophilus influenzae

<400> SEQUENCE: 114

Phe Lys Gln Thr Ala Pro Ser Asn Asn Glu Val Glu Asn Glu Leu Thr
1               5                   10                  15

Asn Glu Gln Leu Thr Lys
            20

<210> SEQ ID NO 115
<211> LENGTH: 17
<212> TYPE: PRT
<213> ORGANISM: Haemophilus influenzae

<400> SEQUENCE: 115

Gly Ile Asp Gly Leu Val Leu Gly Ala Asn Tyr Leu Leu Ala Gln Glu
1               5                   10                  15

Arg

<210> SEQ ID NO 116
<211> LENGTH: 13
<212> TYPE: PRT
<213> ORGANISM: Haemophilus influenzae

<400> SEQUENCE: 116

Ile Ala Glu Gln Ser Asn Ser Thr Ile Lys Asp Gln Lys
1               5                   10

<210> SEQ ID NO 117
<211> LENGTH: 14
<212> TYPE: PRT
<213> ORGANISM: Haemophilus influenzae

<400> SEQUENCE: 117

Thr Ala Gln Phe Ser Thr Gly Gly Val Tyr Ile Asp Ser Arg
1               5                   10

<210> SEQ ID NO 118
<211> LENGTH: 15
<212> TYPE: PRT
<213> ORGANISM: Haemophilus influenzae

<400> SEQUENCE: 118

Tyr Ala Tyr Val Thr Leu Gly Asn Asn Thr Phe Gly Glu Val Lys

<210> SEQ ID NO 119
<211> LENGTH: 22
<212> TYPE: PRT
<213> ORGANISM: Haemophilus influenzae

<400> SEQUENCE: 119

Ala Asn Leu Lys Pro Gln Ala Gln Ala Thr Leu Asp Ser Val Tyr Gly
1               5                   10                  15

Glu Ile Ser Gln Val Lys
            20

<210> SEQ ID NO 120
<211> LENGTH: 11
<212> TYPE: PRT
<213> ORGANISM: Haemophilus influenzae

<400> SEQUENCE: 120

Ala Gln Gln Leu Ser Thr Asp Val Lys Asn Lys
1               5                   10

<210> SEQ ID NO 121
<211> LENGTH: 16
<212> TYPE: PRT
<213> ORGANISM: Haemophilus influenzae

<400> SEQUENCE: 121

Glu Ile Thr Glu Asp Pro Ala Ile Tyr Pro Ser Ala Asp Ile Leu Lys
1               5                   10                  15

<210> SEQ ID NO 122
<211> LENGTH: 18
<212> TYPE: PRT
<213> ORGANISM: Haemophilus influenzae

<400> SEQUENCE: 122

Gly Leu Lys Val Glu Asn Thr Asn Asn Pro Ile Gln Val Pro Val Gly
1               5                   10                  15

Thr Lys

<210> SEQ ID NO 123
<211> LENGTH: 18
<212> TYPE: PRT
<213> ORGANISM: Haemophilus influenzae

<400> SEQUENCE: 123

Gly Val Ile Thr Val Ser Ala Val Gly Asp Gln Ile Asn Pro Thr Leu
1               5                   10                  15

Ala Arg

<210> SEQ ID NO 124
<211> LENGTH: 16
<212> TYPE: PRT
<213> ORGANISM: Haemophilus influenzae

<400> SEQUENCE: 124

Ile Asn Ala Thr Glu Gly Ala Ala Thr Leu Thr Ala Glu Ser Gly Lys
1               5                   10                  15

<210> SEQ ID NO 125
<211> LENGTH: 16
<212> TYPE: PRT

```
<213> ORGANISM: Haemophilus influenzae

<400> SEQUENCE: 125

Leu Ser Val Ile Ala Glu Gln Ser Asn Ser Thr Ala Asp Asp Gln Lys
1               5                   10                  15

<210> SEQ ID NO 126
<211> LENGTH: 16
<212> TYPE: PRT
<213> ORGANISM: Haemophilus influenzae

<400> SEQUENCE: 126

Leu Ser Val Ile Ala Glu Gln Ser Asn Thr Thr Val Asp Asp Gln Lys
1               5                   10                  15

<210> SEQ ID NO 127
<211> LENGTH: 19
<212> TYPE: PRT
<213> ORGANISM: Haemophilus influenzae

<400> SEQUENCE: 127

Leu Val Ser Ala Gln Ser Gly Thr Glu Ser Asp Asn Phe Gly His Ile
1               5                   10                  15

Ile Thr Lys

<210> SEQ ID NO 128
<211> LENGTH: 11
<212> TYPE: PRT
<213> ORGANISM: Haemophilus influenzae

<400> SEQUENCE: 128

Asn Glu Gly Thr Asn Val Glu Leu Gly Gly Arg
1               5                   10

<210> SEQ ID NO 129
<211> LENGTH: 18
<212> TYPE: PRT
<213> ORGANISM: Haemophilus influenzae

<400> SEQUENCE: 129

Arg Ala Glu Leu Glu Ala Thr Ala Ala Ala Asn Leu Ala Ala Ala Gln
1               5                   10                  15

Ala Arg

<210> SEQ ID NO 130
<211> LENGTH: 17
<212> TYPE: PRT
<213> ORGANISM: Haemophilus influenzae

<400> SEQUENCE: 130

Ser Ala Asp Leu Thr Ser Glu Val Ala Val Gly Asp Val Val Asp Ala
1               5                   10                  15

Lys

<210> SEQ ID NO 131
<211> LENGTH: 15
<212> TYPE: PRT
<213> ORGANISM: Haemophilus influenzae

<400> SEQUENCE: 131

Ser Ile Ile Ala Glu Gln Ser Asn Ser Thr Ile Lys Asp Gln Lys
1               5                   10                  15
```

<210> SEQ ID NO 132
<211> LENGTH: 17
<212> TYPE: PRT
<213> ORGANISM: Haemophilus influenzae

<400> SEQUENCE: 132

Ser Val Asp Leu Thr Ser Glu Val Ala Val Gly Asp Val Val Glu Ala
1               5                   10                  15

Lys

<210> SEQ ID NO 133
<211> LENGTH: 21
<212> TYPE: PRT
<213> ORGANISM: Haemophilus influenzae

<400> SEQUENCE: 133

Thr Ile Ala Asp Gly Ile Thr Ser Ala Glu Asp Lys Glu Tyr Gly Val
1               5                   10                  15

Leu Asn Asn Ser Lys
            20

<210> SEQ ID NO 134
<211> LENGTH: 19
<212> TYPE: PRT
<213> ORGANISM: Haemophilus influenzae

<400> SEQUENCE: 134

Thr Ile Ile Gly Ala Asn Leu Ser Gln Leu Thr Gln Asn Glu Leu Ser
1               5                   10                  15

Ala Gly Lys

<210> SEQ ID NO 135
<211> LENGTH: 12
<212> TYPE: PRT
<213> ORGANISM: Haemophilus influenzae

<400> SEQUENCE: 135

Thr Gln Thr Ser Thr Ser Ile Gly Phe Asn Ala Lys
1               5                   10

<210> SEQ ID NO 136
<211> LENGTH: 15
<212> TYPE: PRT
<213> ORGANISM: Staphylococcus aureus

<400> SEQUENCE: 136

Asn Ala Leu Ile Ile Glu Asp Thr Gly Asp Asn Val Val Lys
1               5                   10                  15

<210> SEQ ID NO 137
<211> LENGTH: 16
<212> TYPE: PRT
<213> ORGANISM: Staphylococcus aureus

<400> SEQUENCE: 137

Asp Leu Ser Phe Gly Glu Asn Tyr Gly Val Val Met Glu Glu Leu Arg
1               5                   10                  15

<210> SEQ ID NO 138
<211> LENGTH: 12
<212> TYPE: PRT
<213> ORGANISM: Staphylococcus aureus

<400> SEQUENCE: 138

Thr Pro Thr Glu Gln Thr Lys Pro Val Gln Pro Lys
1               5                   10

<210> SEQ ID NO 139
<211> LENGTH: 14
<212> TYPE: PRT
<213> ORGANISM: Staphylococcus aureus

<400> SEQUENCE: 139

Val Met Gly Val Asp Tyr Val Ser Asn Ile Thr Glu Ala Arg
1               5                   10

<210> SEQ ID NO 140
<211> LENGTH: 13
<212> TYPE: PRT
<213> ORGANISM: Staphylococcus aureus

<400> SEQUENCE: 140

Tyr Leu Gly Asp Glu Glu Ile Ser Val Ser Glu Leu Lys
1               5                   10

<210> SEQ ID NO 141
<211> LENGTH: 15
<212> TYPE: PRT
<213> ORGANISM: Staphylococcus aureus

<400> SEQUENCE: 141

Ala Glu Ala Gln Ala Asn Gln Met Val Gly Asp Ala Val Glu Lys
1               5                   10                  15

<210> SEQ ID NO 142
<211> LENGTH: 17
<212> TYPE: PRT
<213> ORGANISM: Staphylococcus aureus

<400> SEQUENCE: 142

Ala Asn Glu Leu Leu Lys Asp Asn Ala Glu Leu Ile Ala Ser Phe Ser
1               5                   10                  15

Arg

<210> SEQ ID NO 143
<211> LENGTH: 15
<212> TYPE: PRT
<213> ORGANISM: Staphylococcus aureus

<400> SEQUENCE: 143

Ala Thr Asp Ala Glu Asn Val Glu Lys Glu Glu Ala Ile Thr Lys
1               5                   10                  15

<210> SEQ ID NO 144
<211> LENGTH: 15
<212> TYPE: PRT
<213> ORGANISM: Staphylococcus aureus

<400> SEQUENCE: 144

Ala Val Ala Gly Ala Ala Gly Gly Ala Asp Ala Ala Ala Glu Lys
1               5                   10                  15

<210> SEQ ID NO 145
<211> LENGTH: 15
<212> TYPE: PRT
<213> ORGANISM: Staphylococcus aureus

<400> SEQUENCE: 145

Glu Leu Ile Asn Gly Val Phe Thr Asp Ile Asn Pro Tyr Ile Lys
1               5                   10                  15

<210> SEQ ID NO 146
<211> LENGTH: 18
<212> TYPE: PRT
<213> ORGANISM: Staphylococcus aureus

<400> SEQUENCE: 146

His Ile Gly Thr Pro Gly Glu Val Leu Glu Pro Gly Gln Gln Val Asn
1               5                   10                  15

Val Lys

<210> SEQ ID NO 147
<211> LENGTH: 13
<212> TYPE: PRT
<213> ORGANISM: Staphylococcus aureus

<400> SEQUENCE: 147

Lys Ala Gln Ser Glu Gln Asp Gln Ala Phe Leu Ser Lys
1               5                   10

<210> SEQ ID NO 148
<211> LENGTH: 13
<212> TYPE: PRT
<213> ORGANISM: Staphylococcus aureus

<400> SEQUENCE: 148

Met Ile Ala Val Leu Ile Pro Asp Asp Gly Ser Gly Lys
1               5                   10

<210> SEQ ID NO 149
<211> LENGTH: 19
<212> TYPE: PRT
<213> ORGANISM: Staphylococcus aureus

<400> SEQUENCE: 149

Asn Ala Gly Ile Gly Ser Gly Phe Ser Asn Asp Met Tyr Glu Lys Glu
1               5                   10                  15

Gly Ala Lys

<210> SEQ ID NO 150
<211> LENGTH: 18
<212> TYPE: PRT
<213> ORGANISM: Staphylococcus aureus

<400> SEQUENCE: 150

Gln Asn Leu Pro Val Leu Asp Val Pro Glu Asp Val Val Glu Glu Gly
1               5                   10                  15

Val Arg

<210> SEQ ID NO 151
<211> LENGTH: 28
<212> TYPE: PRT
<213> ORGANISM: Staphylococcus aureus

<400> SEQUENCE: 151

Val Val Ile Thr Ala Gln Thr Ile Asn Glu Glu Thr Glu Pro Glu Leu
1               5                   10                  15

Tyr Asp Ala Glu Gly Asn Leu Ile Asn Asn Ser Lys
            20                  25

<210> SEQ ID NO 152
<211> LENGTH: 12
<212> TYPE: PRT
<213> ORGANISM: Staphylococcus aureus

<400> SEQUENCE: 152

Ala Asp Ser Gly Thr Val Ile Gln Ala Ile Ser Lys
1               5                   10

<210> SEQ ID NO 153
<211> LENGTH: 17
<212> TYPE: PRT
<213> ORGANISM: Staphylococcus aureus

<400> SEQUENCE: 153

Ala Thr Ile Asp Gly Leu Gln Asn Leu Lys Asn Ala Glu Asp Val Ala
1               5                   10                  15

Lys

<210> SEQ ID NO 154
<211> LENGTH: 16
<212> TYPE: PRT
<213> ORGANISM: Staphylococcus aureus

<400> SEQUENCE: 154

Asp Ser Asp Ile Ala Thr Thr Ala Thr Lys Val Glu Leu Ala Thr Lys
1               5                   10                  15

<210> SEQ ID NO 155
<211> LENGTH: 17
<212> TYPE: PRT
<213> ORGANISM: Staphylococcus aureus

<400> SEQUENCE: 155

Phe Ile Ala Glu Thr Tyr Leu Asp Asp Val Glu Gln Phe Asn Thr Val
1               5                   10                  15

Arg

<210> SEQ ID NO 156
<211> LENGTH: 17
<212> TYPE: PRT
<213> ORGANISM: Staphylococcus aureus

<400> SEQUENCE: 156

Phe Ile Glu Glu Thr Pro Glu Leu Phe Asp Ile Gln Pro Ser Leu Asp
1               5                   10                  15

Arg

<210> SEQ ID NO 157
<211> LENGTH: 14
<212> TYPE: PRT
<213> ORGANISM: Staphylococcus aureus

<400> SEQUENCE: 157

Gly Leu Trp Asn Glu Asn Lys Glu Asn Glu Val Ile Glu Arg
1               5                   10

<210> SEQ ID NO 158
<211> LENGTH: 16
<212> TYPE: PRT
<213> ORGANISM: Staphylococcus aureus

<400> SEQUENCE: 158

Ile Phe Ser Glu Val Glu Pro Asn Pro Ser Thr Asn Thr Val Tyr Lys
1               5                   10                  15

<210> SEQ ID NO 159
<211> LENGTH: 17
<212> TYPE: PRT
<213> ORGANISM: Staphylococcus aureus

<400> SEQUENCE: 159

Leu Ala Glu Gln Lys Ala Thr Asp Ala Glu Asn Val Glu Lys Glu Glu
1               5                   10                  15

Ala

<210> SEQ ID NO 160
<211> LENGTH: 13
<212> TYPE: PRT
<213> ORGANISM: Staphylococcus aureus

<400> SEQUENCE: 160

Leu Ala Val Asn Glu Met Leu Asn Ala Ile Gln Asn Lys
1               5                   10

<210> SEQ ID NO 161
<211> LENGTH: 16
<212> TYPE: PRT
<213> ORGANISM: Staphylococcus aureus

<400> SEQUENCE: 161

Leu Asn Asp Val Glu Gln Thr Asn Thr Pro Gly Ser Leu Asn Pro Lys
1               5                   10                  15

<210> SEQ ID NO 162
<211> LENGTH: 16
<212> TYPE: PRT
<213> ORGANISM: Staphylococcus aureus

<400> SEQUENCE: 162

Met Gln Glu Val Gly Val Thr Ala Ile Ser Gly Glu Thr Ile Ile Lys
1               5                   10                  15

<210> SEQ ID NO 163
<211> LENGTH: 12
<212> TYPE: PRT
<213> ORGANISM: Staphylococcus aureus

<400> SEQUENCE: 163

Asn Leu Ser Glu Gln Gly Ile Asn Glu Ala Thr Arg
1               5                   10

<210> SEQ ID NO 164
<211> LENGTH: 15
<212> TYPE: PRT
<213> ORGANISM: Staphylococcus aureus

<400> SEQUENCE: 164

Asn Met Leu Pro Glu Val Lys Pro Ser Ser Glu Val Tyr Gly Lys
1               5                   10                  15

<210> SEQ ID NO 165
<211> LENGTH: 39
<212> TYPE: PRT
<213> ORGANISM: Staphylococcus aureus -continued

<400> SEQUENCE: 165

Asn Val Lys Asp Asn Ala Ile Val Leu Glu Ala Ile Ser Gly Ala Asp
1               5                   10                  15

Val Asn Asp Ser Thr Ser Ala Pro Val Asp Asp Val Asp Phe Thr Ser
            20                  25                  30

Asp Ile Gly Lys Asp Ile Lys
            35

<210> SEQ ID NO 166
<211> LENGTH: 19
<212> TYPE: PRT
<213> ORGANISM: Staphylococcus aureus

<400> SEQUENCE: 166

Gln Asn Leu Pro Val Leu Asp Val Pro Glu Asp Val Val Glu Glu Gly
1               5                   10                  15

Val Arg Lys

<210> SEQ ID NO 167
<211> LENGTH: 27
<212> TYPE: PRT
<213> ORGANISM: Staphylococcus aureus

<400> SEQUENCE: 167

Ser Gly Ala Asp Val Asn Asp Ser Thr Ser Ala Pro Val Asp Asp Val
1               5                   10                  15

Asp Phe Thr Ser Asp Ile Gly Lys Asp Ile Lys
            20                  25

<210> SEQ ID NO 168
<211> LENGTH: 15
<212> TYPE: PRT
<213> ORGANISM: Streptococcus pneumoniae

<400> SEQUENCE: 168

Asp Val Pro Glu Asn Leu Ile Thr Ala Val Val Gln Ser Asn Lys
1               5                   10                  15

<210> SEQ ID NO 169
<211> LENGTH: 12
<212> TYPE: PRT
<213> ORGANISM: Streptococcus pneumoniae

<400> SEQUENCE: 169

Glu Ala Glu Ala Asn Phe Asn Thr Glu Gln Ala Lys
1               5                   10

<210> SEQ ID NO 170
<211> LENGTH: 16
<212> TYPE: PRT
<213> ORGANISM: Streptococcus pneumoniae

<400> SEQUENCE: 170

Glu Ile Asp Glu Ser Asp Ser Glu Asp Tyr Leu Lys Glu Gly Leu Arg
1               5                   10                  15

<210> SEQ ID NO 171
<211> LENGTH: 16
<212> TYPE: PRT
<213> ORGANISM: Streptococcus pneumoniae

<400> SEQUENCE: 171

```
Ile Asp Thr Phe Gly Thr Gly Thr Val Ala Glu Ser Gln Leu Glu Lys
1               5                   10                  15
```

<210> SEQ ID NO 172
<211> LENGTH: 18
<212> TYPE: PRT
<213> ORGANISM: Streptococcus pneumoniae

<400> SEQUENCE: 172

```
Leu Lys Glu Ile Asp Glu Ser Asp Ser Glu Asp Tyr Val Lys Glu Gly
1               5                   10                  15

Phe Arg
```

<210> SEQ ID NO 173
<211> LENGTH: 18
<212> TYPE: PRT
<213> ORGANISM: Streptococcus pneumoniae

<400> SEQUENCE: 173

```
Leu Lys Glu Ile Asp Glu Ser Asp Ser Glu Asp Tyr Val Lys Glu Gly
1               5                   10                  15

Leu Arg
```

<210> SEQ ID NO 174
<211> LENGTH: 17
<212> TYPE: PRT
<213> ORGANISM: Streptococcus pneumoniae

<400> SEQUENCE: 174

```
Leu Leu Ala Gly Ala Asp Pro Asp Asp Gly Thr Glu Val Ile Glu Ala
1               5                   10                  15

Lys
```

<210> SEQ ID NO 175
<211> LENGTH: 18
<212> TYPE: PRT
<213> ORGANISM: Streptococcus pneumoniae

<400> SEQUENCE: 175

```
Asn Gly Asn Tyr Glu Thr Ala Glu Gly Ser Glu Glu Thr Ser Ser Glu
1               5                   10                  15

Val Lys
```

<210> SEQ ID NO 176
<211> LENGTH: 14
<212> TYPE: PRT
<213> ORGANISM: Streptococcus pneumoniae

<400> SEQUENCE: 176

```
Asn Thr Leu Leu Glu Leu Gly Leu Asp Glu Ser Gln Ile Lys
1               5                   10
```

<210> SEQ ID NO 177
<211> LENGTH: 16
<212> TYPE: PRT
<213> ORGANISM: Streptococcus pneumoniae

<400> SEQUENCE: 177

```
Val Ala Ala Gly Asp Leu Leu Val Thr Ala Asp Leu Asn Ala Ile Arg
1               5                   10                  15
```

<210> SEQ ID NO 178

```
<211> LENGTH: 12
<212> TYPE: PRT
<213> ORGANISM: Streptococcus pneumoniae

<400> SEQUENCE: 178

Val Ile Pro Lys Glu Thr Glu Leu Ala Thr Thr Lys
1               5                   10

<210> SEQ ID NO 179
<211> LENGTH: 12
<212> TYPE: PRT
<213> ORGANISM: Streptococcus pneumoniae

<400> SEQUENCE: 179

Val Val Pro Glu Ala Glu Gln Leu Ala Glu Thr Lys
1               5                   10

<210> SEQ ID NO 180
<211> LENGTH: 16
<212> TYPE: PRT
<213> ORGANISM: Streptococcus pneumoniae

<400> SEQUENCE: 180

Ala Glu Lys Asp Tyr Asp Ala Ala Met Lys Asn Ala Glu Asp Ala Lys
1               5                   10                  15

<210> SEQ ID NO 181
<211> LENGTH: 15
<212> TYPE: PRT
<213> ORGANISM: Streptococcus pneumoniae

<400> SEQUENCE: 181

Ala Glu Lys Pro Ala Asp Gln Gln Ala Glu Glu Asp Tyr Ala Arg
1               5                   10                  15

<210> SEQ ID NO 182
<211> LENGTH: 14
<212> TYPE: PRT
<213> ORGANISM: Streptococcus pneumoniae

<400> SEQUENCE: 182

Ala Glu Ser Thr Gly Glu Phe Thr Ser Glu Gln Phe Glu Lys
1               5                   10

<210> SEQ ID NO 183
<211> LENGTH: 14
<212> TYPE: PRT
<213> ORGANISM: Streptococcus pneumoniae

<400> SEQUENCE: 183

Ala Gly Ile Thr Tyr Ser Glu Gly Leu Val Phe Glu Ser Lys
1               5                   10

<210> SEQ ID NO 184
<211> LENGTH: 13
<212> TYPE: PRT
<213> ORGANISM: Streptococcus pneumoniae

<400> SEQUENCE: 184

Ala Gly Val Val Val Val Asp Asn Thr Ser Tyr Phe Arg
1               5                   10

<210> SEQ ID NO 185
<211> LENGTH: 16
<212> TYPE: PRT
```

-continued

<213> ORGANISM: Streptococcus pneumoniae

<400> SEQUENCE: 185

Ala Ile Glu Ala Gly Gln Thr Val Asp Phe Ser Asp Leu Ala Ile Lys
1               5                   10                  15

<210> SEQ ID NO 186
<211> LENGTH: 10
<212> TYPE: PRT
<213> ORGANISM: Streptococcus pneumoniae

<400> SEQUENCE: 186

Ala Leu Thr Pro Glu Glu Val Gln Lys Arg
1               5                   10

<210> SEQ ID NO 187
<211> LENGTH: 17
<212> TYPE: PRT
<213> ORGANISM: Streptococcus pneumoniae

<400> SEQUENCE: 187

Ala Gln Asn Thr Glu Ser Thr Val Val Gln Leu Asn Asn Gly Asp Val
1               5                   10                  15

Lys

<210> SEQ ID NO 188
<211> LENGTH: 13
<212> TYPE: PRT
<213> ORGANISM: Streptococcus pneumoniae

<400> SEQUENCE: 188

Asp Ala Glu His Ala Glu Glu Val Ala Pro Gln Val Lys
1               5                   10

<210> SEQ ID NO 189
<211> LENGTH: 13
<212> TYPE: PRT
<213> ORGANISM: Streptococcus pneumoniae

<400> SEQUENCE: 189

Asp Ile Ile Leu Ala Gln Thr Glu Glu Asn Leu Thr Arg
1               5                   10

<210> SEQ ID NO 190
<211> LENGTH: 23
<212> TYPE: PRT
<213> ORGANISM: Streptococcus pneumoniae

<400> SEQUENCE: 190

Asp Leu Glu Asn Val Glu Thr Val Ile Glu Lys Glu Asp Val Glu Thr
1               5                   10                  15

Asn Ala Ser Asn Gly Gln Arg
            20

<210> SEQ ID NO 191
<211> LENGTH: 13
<212> TYPE: PRT
<213> ORGANISM: Streptococcus pneumoniae

<400> SEQUENCE: 191

Glu Ala Gly Asp Gln Ala Thr Tyr Phe Asp Glu Ile Arg
1               5                   10

-continued

```
<210> SEQ ID NO 192
<211> LENGTH: 19
<212> TYPE: PRT
<213> ORGANISM: Streptococcus pneumoniae

<400> SEQUENCE: 192

Glu Gly Phe Val Lys Asn Val Glu Ile Ile Glu Asp Asp Lys Gln Gly
1               5                   10                  15

Val Ile Arg

<210> SEQ ID NO 193
<211> LENGTH: 11
<212> TYPE: PRT
<213> ORGANISM: Streptococcus pneumoniae

<400> SEQUENCE: 193

Glu Leu Ala Thr Gln Ile Tyr Gln Val Ala Arg
1               5                   10

<210> SEQ ID NO 194
<211> LENGTH: 17
<212> TYPE: PRT
<213> ORGANISM: Streptococcus pneumoniae

<400> SEQUENCE: 194

Gly Ser Asp Gly Lys Gln Phe Tyr Asn Asn Tyr Asn Asp Ala Pro Leu
1               5                   10                  15

Lys

<210> SEQ ID NO 195
<211> LENGTH: 17
<212> TYPE: PRT
<213> ORGANISM: Streptococcus pneumoniae

<400> SEQUENCE: 195

Gly Ser Ile Glu Ser Met His Asn Leu Pro Val Asn Leu Ala Gly Ala
1               5                   10                  15

Arg

<210> SEQ ID NO 196
<211> LENGTH: 24
<212> TYPE: PRT
<213> ORGANISM: Streptococcus pneumoniae

<400> SEQUENCE: 196

Ile Ala Glu Ala Thr Lys Glu Val Gln Gln Ala Tyr Leu Ala Tyr Gln
1               5                   10                  15

Gln Ala Ser Asn Glu Ser Gln Arg
                20

<210> SEQ ID NO 197
<211> LENGTH: 13
<212> TYPE: PRT
<213> ORGANISM: Streptococcus pneumoniae

<400> SEQUENCE: 197

Ile Gly Gly Gly Tyr Ala Gly Gln Ser Gly Ala Ile Arg
1               5                   10

<210> SEQ ID NO 198
<211> LENGTH: 16
<212> TYPE: PRT
<213> ORGANISM: Escherichia coli
```

```
<400> SEQUENCE: 198

Ala Ile Asp Asp Leu Val Lys Gly Phe Glu Glu Leu Asp Thr Ser Lys
1               5                   10                  15

<210> SEQ ID NO 199
<211> LENGTH: 13
<212> TYPE: PRT
<213> ORGANISM: Escherichia coli

<400> SEQUENCE: 199

Ala Asn Ser Ser Thr Thr Thr Ala Ala Glu Pro Leu Lys
1               5                   10

<210> SEQ ID NO 200
<211> LENGTH: 11
<212> TYPE: PRT
<213> ORGANISM: Escherichia coli

<400> SEQUENCE: 200

Gln Val Pro Ile Leu Gln Lys Asp Asp Ser Arg
1               5                   10

<210> SEQ ID NO 201
<211> LENGTH: 15
<212> TYPE: PRT
<213> ORGANISM: Escherichia coli

<400> SEQUENCE: 201

Val Phe Asp Val Asn Glu Pro Leu Ser Gln Ile Asn Gln Ala Lys
1               5                   10                  15

<210> SEQ ID NO 202
<211> LENGTH: 15
<212> TYPE: PRT
<213> ORGANISM: Escherichia coli

<400> SEQUENCE: 202

Val Pro Val Phe Ala Gly Asp Thr Glu Asp Ile Thr Ala Arg
1               5                   10                  15

<210> SEQ ID NO 203
<211> LENGTH: 23
<212> TYPE: PRT
<213> ORGANISM: Escherichia coli

<400> SEQUENCE: 203

Ser Val Gln Thr Val Thr Gly Gln Pro Asp Val Asp Gln Val Val Leu
1               5                   10                  15

Asp Glu Ala Ile Lys Asn Arg
            20

<210> SEQ ID NO 204
<211> LENGTH: 19
<212> TYPE: PRT
<213> ORGANISM: Escherichia coli

<400> SEQUENCE: 204

Leu Ile Ala Ala Ala Pro Thr Ala Val Ala Pro Glu Glu Ser Gly Phe
1               5                   10                  15

Tyr Ala Arg

<210> SEQ ID NO 205
```

```
<211> LENGTH: 18
<212> TYPE: PRT
<213> ORGANISM: Escherichia coli

<400> SEQUENCE: 205

Asn Ala Glu Phe Leu Gln Ala Tyr Gly Val Ala Ile Ala Asp Gly Pro
1               5                   10                  15

Leu Lys

<210> SEQ ID NO 206
<211> LENGTH: 12
<212> TYPE: PRT
<213> ORGANISM: Escherichia coli

<400> SEQUENCE: 206

Glu Ile Ala Phe Glu Glu Leu Gly Ser Gln Ala Arg
1               5                   10

<210> SEQ ID NO 207
<211> LENGTH: 17
<212> TYPE: PRT
<213> ORGANISM: Escherichia coli

<400> SEQUENCE: 207

Ala Glu Val Pro Ser Gly Thr Val Leu Ala Glu Lys Gln Glu Leu Val
1               5                   10                  15

Arg

<210> SEQ ID NO 208
<211> LENGTH: 20
<212> TYPE: PRT
<213> ORGANISM: Escherichia coli

<400> SEQUENCE: 208

Ala Pro Arg Pro Ala Pro Ala Pro Gln Ala Pro Ala Gln Asn Thr Thr
1               5                   10                  15

Pro Val Thr Lys
            20

<210> SEQ ID NO 209
<211> LENGTH: 12
<212> TYPE: PRT
<213> ORGANISM: Escherichia coli

<400> SEQUENCE: 209

Arg Thr Glu Pro Ala Ala Pro Val Ala Ser Thr Lys
1               5                   10

<210> SEQ ID NO 210
<211> LENGTH: 14
<212> TYPE: PRT
<213> ORGANISM: Escherichia coli

<400> SEQUENCE: 210

Ser Asp Thr Tyr Gly Trp Gln Glu Asp Ser Thr Tyr Ile Arg
1               5                   10

<210> SEQ ID NO 211
<211> LENGTH: 11
<212> TYPE: PRT
<213> ORGANISM: Escherichia coli

<400> SEQUENCE: 211
```

Ser Tyr Glu Glu Glu Leu Ala Lys Asp Pro Arg
1               5                   10

<210> SEQ ID NO 212
<211> LENGTH: 23
<212> TYPE: PRT
<213> ORGANISM: Escherichia coli

<400> SEQUENCE: 212

Arg Thr Glu Pro Ala Ala Pro Val Ala Ser Thr Lys Ala Pro Ala Ala
1               5                   10                  15

Thr Ser Thr Pro Ala Pro Lys
            20

<210> SEQ ID NO 213
<211> LENGTH: 19
<212> TYPE: PRT
<213> ORGANISM: Escherichia coli

<400> SEQUENCE: 213

Ala Asp Gly Ile Asn Pro Glu Glu Leu Leu Gly Asn Ser Ser Ala Ala
1               5                   10                  15

Ala Pro Arg

<210> SEQ ID NO 214
<211> LENGTH: 16
<212> TYPE: PRT
<213> ORGANISM: Escherichia coli

<400> SEQUENCE: 214

Ile Val Gln Ser Pro Asp Val Ile Pro Ala Asp Ser Glu Ala Gly Arg
1               5                   10                  15

<210> SEQ ID NO 215
<211> LENGTH: 17
<212> TYPE: PRT
<213> ORGANISM: Escherichia coli

<400> SEQUENCE: 215

Met Ala Glu Arg Pro Glu Val Gln Asp Ala Leu Ser Ala Glu Gly Leu
1               5                   10                  15

Lys

<210> SEQ ID NO 216
<211> LENGTH: 23
<212> TYPE: PRT
<213> ORGANISM: Escherichia coli

<400> SEQUENCE: 216

Asn Ala Glu Phe Leu Gln Ala Tyr Gly Val Ala Ile Ala Asp Gly Pro
1               5                   10                  15

Leu Lys Gly Leu Ala Ala Arg
            20

<210> SEQ ID NO 217
<211> LENGTH: 10
<212> TYPE: PRT
<213> ORGANISM: Escherichia coli

<400> SEQUENCE: 217

Gln Gln Ala Glu Val Thr Glu Lys Ala Arg
1               5                   10

<210> SEQ ID NO 218
<211> LENGTH: 11
<212> TYPE: PRT
<213> ORGANISM: Escherichia coli

<400> SEQUENCE: 218

Ala Pro Ala Ala Thr Ser Thr Pro Ala Pro Lys
1               5                   10

<210> SEQ ID NO 219
<211> LENGTH: 15
<212> TYPE: PRT
<213> ORGANISM: Escherichia coli

<400> SEQUENCE: 219

Ala Phe Asp Ser Gln Thr Glu Asp Ser Ser Pro Ala Ile Gly Arg
1               5                   10                  15

<210> SEQ ID NO 220
<211> LENGTH: 12
<212> TYPE: PRT
<213> ORGANISM: Escherichia coli

<400> SEQUENCE: 220

Pro Asn Glu Leu Leu Asn Ser Leu Ala Ala Val Lys
1               5                   10

<210> SEQ ID NO 221
<211> LENGTH: 22
<212> TYPE: PRT
<213> ORGANISM: Escherichia coli

<400> SEQUENCE: 221

Ala Pro Ala Lys Glu Ser Ala Pro Ala Ala Ala Pro Ala Ala Gln
1               5                   10                  15

Pro Ala Leu Ala Ala Arg
            20

<210> SEQ ID NO 222
<211> LENGTH: 17
<212> TYPE: PRT
<213> ORGANISM: Escherichia coli

<400> SEQUENCE: 222

Met Asn Ala Phe Asp Ser Gln Thr Glu Asp Ser Ser Pro Ala Ile Gly
1               5                   10                  15

Arg

<210> SEQ ID NO 223
<211> LENGTH: 18
<212> TYPE: PRT
<213> ORGANISM: Escherichia coli

<400> SEQUENCE: 223

Ser Gly Asp Leu Thr Ala Phe Glu Pro Glu Leu Leu Lys Glu His Asn
1               5                   10                  15

Ala Arg

<210> SEQ ID NO 224
<211> LENGTH: 16
<212> TYPE: PRT
<213> ORGANISM: Escherichia coli

```
<400> SEQUENCE: 224

Ser Leu Ser Asp Thr Leu Glu Glu Val Leu Ser Ser Ser Gly Glu Lys
1               5                   10                  15

<210> SEQ ID NO 225
<211> LENGTH: 19
<212> TYPE: PRT
<213> ORGANISM: Escherichia coli

<400> SEQUENCE: 225

Asn Ile Pro Val Glu Leu His Val Leu Leu Asn Asp Asp Ala Glu Thr
1               5                   10                  15

Pro Thr Arg

<210> SEQ ID NO 226
<211> LENGTH: 18
<212> TYPE: PRT
<213> ORGANISM: Escherichia coli

<400> SEQUENCE: 226

Gln Ala Gln Ile Asn Gly Leu Glu Met Ala Phe Leu Ser Ala Glu Glu
1               5                   10                  15

Lys Arg

<210> SEQ ID NO 227
<211> LENGTH: 16
<212> TYPE: PRT
<213> ORGANISM: Escherichia coli

<400> SEQUENCE: 227

Gln Glu Ala Ala Pro Ala Ala Ala Pro Ala Pro Ala Ala Gly Val Lys
1               5                   10                  15

<210> SEQ ID NO 228
<211> LENGTH: 12
<212> TYPE: PRT
<213> ORGANISM: Escherichia coli

<400> SEQUENCE: 228

Ser Arg Leu Pro Gln Asn Ile Thr Leu Thr Glu Val
1               5                   10

<210> SEQ ID NO 229
<211> LENGTH: 26
<212> TYPE: PRT
<213> ORGANISM: Escherichia coli

<400> SEQUENCE: 229

His Leu Ala Lys Ala Pro Ala Lys Glu Ser Ala Pro Ala Ala Ala Ala
1               5                   10                  15

Pro Ala Ala Gln Pro Ala Leu Ala Ala Arg
            20                  25

<210> SEQ ID NO 230
<211> LENGTH: 22
<212> TYPE: PRT
<213> ORGANISM: Escherichia coli

<400> SEQUENCE: 230

Leu Thr Ser Ser Thr Ala Thr Ala Ala Thr Ser Lys Pro Val Thr Ser
1               5                   10                  15

Val Ala Ser Gly Pro Arg
```

-continued

```
<210> SEQ ID NO 231
<211> LENGTH: 14
<212> TYPE: PRT
<213> ORGANISM: Escherichia coli

<400> SEQUENCE: 231

Asn Val Glu Tyr Leu Val Val Glu Ala Ala Gly Ala Thr Arg
1               5                   10

<210> SEQ ID NO 232
<211> LENGTH: 19
<212> TYPE: PRT
<213> ORGANISM: Escherichia coli

<400> SEQUENCE: 232

Ser Asp Asp Met Ser Met Gly Leu Pro Ser Ser Ala Gly Glu His Gly
1               5                   10                  15

Val Leu Arg

<210> SEQ ID NO 233
<211> LENGTH: 34
<212> TYPE: PRT
<213> ORGANISM: Escherichia coli

<400> SEQUENCE: 233

Val Arg Tyr Glu Gln Ser Val Ala Glu Ala Val Val Ala Pro Val
1               5                   10                  15

Val Glu Glu Thr Val Ala Ala Glu Pro Ile Val Gln Glu Ala Pro Ala
            20                  25                  30

Pro Arg

<210> SEQ ID NO 234
<211> LENGTH: 16
<212> TYPE: PRT
<213> ORGANISM: Escherichia coli

<400> SEQUENCE: 234

Ala Val Thr Asn Ser Pro Val Val Val Ala Leu Asp Tyr His Asn Arg
1               5                   10                  15

<210> SEQ ID NO 235
<211> LENGTH: 19
<212> TYPE: PRT
<213> ORGANISM: Escherichia coli

<400> SEQUENCE: 235

Glu Ala Pro Leu Ala Val Glu Leu Asp His Asp Lys Val Met Asn Met
1               5                   10                  15

Gln Val Lys

<210> SEQ ID NO 236
<211> LENGTH: 18
<212> TYPE: PRT
<213> ORGANISM: Escherichia coli

<400> SEQUENCE: 236

Ile Met Ser Gly Asn Ser Glu Thr Glu Thr Gln Glu Val Gly Phe Lys
1               5                   10                  15

Glu Arg
```

```
<210> SEQ ID NO 237
<211> LENGTH: 35
<212> TYPE: PRT
<213> ORGANISM: Escherichia coli

<400> SEQUENCE: 237

Lys Arg Pro Glu Gln Pro Ala Leu Ala Thr Phe Ala Met Pro Asp Val
1               5                   10                  15

Pro Pro Ala Pro Thr Pro Ala Glu Pro Ala Ala Pro Val Val Ala Pro
            20                  25                  30

Ala Pro Lys
        35

<210> SEQ ID NO 238
<211> LENGTH: 16
<212> TYPE: PRT
<213> ORGANISM: Escherichia coli

<400> SEQUENCE: 238

Ser Gln Pro Ile Phe Asn Asp Lys Gln Phe Gln Glu Ala Leu Ser Arg
1               5                   10                  15

<210> SEQ ID NO 239
<211> LENGTH: 13
<212> TYPE: PRT
<213> ORGANISM: Escherichia coli

<400> SEQUENCE: 239

Ala Leu Asp Leu Ser Ala Glu Glu Lys Ala Ala Val Arg
1               5                   10

<210> SEQ ID NO 240
<211> LENGTH: 16
<212> TYPE: PRT
<213> ORGANISM: Escherichia coli

<400> SEQUENCE: 240

Ala Leu Glu Lys Val Val Gly Leu Gln Thr Glu Ala Pro Leu Lys Arg
1               5                   10                  15

<210> SEQ ID NO 241
<211> LENGTH: 18
<212> TYPE: PRT
<213> ORGANISM: Escherichia coli

<400> SEQUENCE: 241

Glu Ala Ala Ile Gln Val Ser Asn Val Ala Ile Phe Asn Ala Thr Thr
1               5                   10                  15

Gly Lys

<210> SEQ ID NO 242
<211> LENGTH: 25
<212> TYPE: PRT
<213> ORGANISM: Escherichia coli

<400> SEQUENCE: 242

Glu Thr Ala Thr Thr Ala Pro Val Gln Thr Ala Ser Pro Ala Gln Thr
1               5                   10                  15

Thr Ala Thr Pro Ala Ala Gly Gly Lys
            20                  25

<210> SEQ ID NO 243
```

```
<211> LENGTH: 17
<212> TYPE: PRT
<213> ORGANISM: Escherichia coli

<400> SEQUENCE: 243

Phe Ser Ala Val Leu Glu Gln Gly Ala Ile Ala Ala Gly Ser Asp Asn
1               5                   10                  15
Lys

<210> SEQ ID NO 244
<211> LENGTH: 16
<212> TYPE: PRT
<213> ORGANISM: Escherichia coli

<400> SEQUENCE: 244

Leu His His Ala Asn Asp Thr Asp Ser Phe Ser Ala Thr Asn Val His
1               5                   10                  15

<210> SEQ ID NO 245
<211> LENGTH: 14
<212> TYPE: PRT
<213> ORGANISM: Escherichia coli

<400> SEQUENCE: 245

Asn Val Glu Tyr Leu Val Val Glu Ala Ala Gly Thr Thr Arg
1               5                   10

<210> SEQ ID NO 246
<211> LENGTH: 15
<212> TYPE: PRT
<213> ORGANISM: Escherichia coli

<400> SEQUENCE: 246

Ser Leu Glu His Glu Val Thr Leu Val Asp Asp Thr Leu Val Arg
1               5                   10                  15

<210> SEQ ID NO 247
<211> LENGTH: 15
<212> TYPE: PRT
<213> ORGANISM: Escherichia coli

<400> SEQUENCE: 247

Thr Asn Gly Ser Leu Asn Ala Ala Glu Ala Thr Glu Thr Leu Arg
1               5                   10                  15

<210> SEQ ID NO 248
<211> LENGTH: 18
<212> TYPE: PRT
<213> ORGANISM: Staphylococcus aureus

<400> SEQUENCE: 248

Ala Gln Glu Asn Gly Leu Thr Val Val Asp Ala Phe Asn Phe Glu Ala
1               5                   10                  15
Pro Lys

<210> SEQ ID NO 249
<211> LENGTH: 17
<212> TYPE: PRT
<213> ORGANISM: Haemophilus influenzae

<400> SEQUENCE: 249

Phe Gly Gln Gly Glu Ala Pro Val Val Ala Ala Pro Glu Val Val Ser
1               5                   10                  15
```

Lys

<210> SEQ ID NO 250
<211> LENGTH: 16
<212> TYPE: PRT
<213> ORGANISM: Haemophilus influenzae

<400> SEQUENCE: 250

Asp Gly Gln Val Thr Gly Ala Leu Ala Thr Leu Gly Glu Pro Tyr Lys
1               5                   10                  15

<210> SEQ ID NO 251
<211> LENGTH: 15
<212> TYPE: PRT
<213> ORGANISM: Moraxella catarrhalis

<400> SEQUENCE: 251

Val Gly Asp Glu Ile Glu Ile Ile Gly Ile Lys Pro Thr Ala Lys
1               5                   10                  15

<210> SEQ ID NO 252
<211> LENGTH: 12
<212> TYPE: PRT
<213> ORGANISM: Moraxella catarrhalis

<400> SEQUENCE: 252

Thr Asp Glu Gln Leu Gln Ala Glu Leu Asp Asn Lys
1               5                   10

<210> SEQ ID NO 253
<211> LENGTH: 15
<212> TYPE: PRT
<213> ORGANISM: Moraxella catarrhalis

<400> SEQUENCE: 253

Gly Leu Ile Thr Asn Ser Ile Glu Asn Thr Asn Asn Ile Thr Lys
1               5                   10                  15

<210> SEQ ID NO 254
<211> LENGTH: 18
<212> TYPE: PRT
<213> ORGANISM: Moraxella catarrhalis

<400> SEQUENCE: 254

Asn Thr Ile Glu Gly Glu Asn Ser Val Ala Ile Gly Ser Asn Asn Thr
1               5                   10                  15

Val Lys

<210> SEQ ID NO 255
<211> LENGTH: 11
<212> TYPE: PRT
<213> ORGANISM: Moraxella catarrhalis

<400> SEQUENCE: 255

Gln Gln Thr Glu Ala Ile Asp Ala Leu Asn Lys
1               5                   10

<210> SEQ ID NO 256
<211> LENGTH: 13
<212> TYPE: PRT
<213> ORGANISM: Streptococcus pneumoniae

<400> SEQUENCE: 256

Val Gln Tyr Glu Gly Gly Thr Glu Asp Glu Leu Ile Arg

```
1               5                   10
```

<210> SEQ ID NO 257
<211> LENGTH: 21
<212> TYPE: PRT
<213> ORGANISM: Streptococcus pneumoniae

<400> SEQUENCE: 257

```
Gly Leu Asp Val Thr Asp Glu Glu Gly Asp Asp Val Thr Asn Gly Ile
1               5                   10                  15

Phe Val Gly Ala Lys
            20
```

<210> SEQ ID NO 258
<211> LENGTH: 12
<212> TYPE: PRT
<213> ORGANISM: Streptococcus pneumoniae

<400> SEQUENCE: 258

```
Ser Gln Thr Glu Gln Gly Glu Ile Asn Ile Glu Arg
1               5                   10
```

<210> SEQ ID NO 259
<211> LENGTH: 15
<212> TYPE: PRT
<213> ORGANISM: Streptococcus pneumoniae

<400> SEQUENCE: 259

```
Pro Ala Pro Ala Pro Gln Pro Ala Pro Ala Pro Lys Pro Glu Lys
1               5                   10                  15
```

<210> SEQ ID NO 260
<211> LENGTH: 14
<212> TYPE: PRT
<213> ORGANISM: Streptococcus pneumoniae

<400> SEQUENCE: 260

```
Ala Glu Ala Asp Lys Pro Glu Thr Glu Ala Gly Lys Glu Arg
1               5                   10
```

<210> SEQ ID NO 261
<211> LENGTH: 22
<212> TYPE: PRT
<213> ORGANISM: Streptococcus pneumoniae

<400> SEQUENCE: 261

```
Ala Glu Gly Val Ala Thr Ala Ser Glu Thr Ala Glu Ala Ala Ser Ala
1               5                   10                  15

Ala Lys Pro Glu Glu Lys
            20
```

<210> SEQ ID NO 262
<211> LENGTH: 15
<212> TYPE: PRT
<213> ORGANISM: Staphylococcus aureus

<400> SEQUENCE: 262

```
Ile Thr Tyr Thr Met Ile Gly Asp Pro Ser Gln Thr Ile Thr Arg
1               5                   10                  15
```

<210> SEQ ID NO 263
<211> LENGTH: 24
<212> TYPE: PRT
<213> ORGANISM: Staphylococcus aureus

<400> SEQUENCE: 263

Ala Ile Leu Asn Asn Glu Asn Asn Val Leu Asn Val Ser Ile Gln Leu
1               5                   10                  15

Asp Gly Gln Tyr Gly Gly His Lys
            20

<210> SEQ ID NO 264
<211> LENGTH: 17
<212> TYPE: PRT
<213> ORGANISM: Staphylococcus aureus

<400> SEQUENCE: 264

Gly Leu Glu Val Gly Gln Ile Val Glu Ser Gly Ala Glu Ala Asp Ile
1               5                   10                  15

Lys

<210> SEQ ID NO 265
<211> LENGTH: 17
<212> TYPE: PRT
<213> ORGANISM: Staphylococcus aureus

<400> SEQUENCE: 265

Thr Val Glu Val Asp Gly Tyr Asn Ala Ile Gln Val Gly Phe Glu Asp
1               5                   10                  15

Lys

<210> SEQ ID NO 266
<211> LENGTH: 16
<212> TYPE: PRT
<213> ORGANISM: Staphylococcus aureus

<400> SEQUENCE: 266

Ser Ile Asn Pro Ala Asp Thr Ser Gln Val Ile Ala Asn Ala Ser Lys
1               5                   10                  15

<210> SEQ ID NO 267
<211> LENGTH: 28
<212> TYPE: PRT
<213> ORGANISM: Staphylococcus aureus

<400> SEQUENCE: 267

Gly Gly Leu Thr Asp Thr Phe Thr Asn Ala Phe Ser Ser Gly Asn Asn
1               5                   10                  15

Val Thr Gln Gly Val Ser Val Glu Val Gly Glu Lys
            20                  25

<210> SEQ ID NO 268
<211> LENGTH: 14
<212> TYPE: PRT
<213> ORGANISM: Staphylococcus aureus

<400> SEQUENCE: 268

Asn Phe Asp Val Leu Asp Glu Ala Thr Gly Leu Ala Gln Arg
1               5                   10

<210> SEQ ID NO 269
<211> LENGTH: 17
<212> TYPE: PRT
<213> ORGANISM: Streptococcus pneumoniae

<400> SEQUENCE: 269

Ala Ile Glu Asn Pro Phe Ala Val Glu Val Ala Asp Val Glu Thr Glu
1               5                   10                  15

Lys

<210> SEQ ID NO 270
<211> LENGTH: 16
<212> TYPE: PRT
<213> ORGANISM: Streptococcus pneumoniae

<400> SEQUENCE: 270

Ala Val Val Val Asn Pro Glu Ser Thr Gly Val Ala Ile Glu Glu Lys
1               5                   10                  15

<210> SEQ ID NO 271
<211> LENGTH: 16
<212> TYPE: PRT
<213> ORGANISM: Streptococcus pneumoniae

<400> SEQUENCE: 271

Ile Leu Asp Leu Asn Glu Glu Glu Gly Arg Val Ser Leu Ser Ile Lys
1               5                   10                  15

<210> SEQ ID NO 272
<211> LENGTH: 11
<212> TYPE: PRT
<213> ORGANISM: Streptococcus pneumoniae

<400> SEQUENCE: 272

Leu Tyr Gln Asn Ala Glu Glu Val Ile Asn Lys
1               5                   10

<210> SEQ ID NO 273
<211> LENGTH: 15
<212> TYPE: PRT
<213> ORGANISM: Streptococcus pneumoniae

<400> SEQUENCE: 273

Leu Tyr Gln Asn Ala Glu Glu Val Ile Asn Lys Leu Ser Asp Lys
1               5                   10                  15

<210> SEQ ID NO 274
<211> LENGTH: 22
<212> TYPE: PRT
<213> ORGANISM: Streptococcus pneumoniae

<400> SEQUENCE: 274

Val Ser Asp Val Thr Thr Leu Glu Glu Ala Arg Pro Ala Thr Thr Pro
1               5                   10                  15

Ser Ser Pro Asn Val Arg
            20

<210> SEQ ID NO 275
<211> LENGTH: 15
<212> TYPE: PRT
<213> ORGANISM: Streptococcus pneumoniae

<400> SEQUENCE: 275

Asp Ala Glu Leu Leu Phe Ala Gly Ile Val Gly Asp Thr Gly Arg
1               5                   10                  15

<210> SEQ ID NO 276
<211> LENGTH: 16
<212> TYPE: PRT
<213> ORGANISM: Streptococcus pneumoniae

```
<400> SEQUENCE: 276

Tyr Thr Leu Leu Ala Gly Glu Thr Pro Ala Val Ala Ala Ala Ile Arg
1               5                   10                  15

<210> SEQ ID NO 277
<211> LENGTH: 21
<212> TYPE: PRT
<213> ORGANISM: Streptococcus pneumoniae

<400> SEQUENCE: 277

Ala His Ile Tyr Phe Ile Asn Ser Glu Glu Pro Ser Gln Leu Asn Asp
1               5                   10                  15

Leu Gln Ala Phe Arg
            20

<210> SEQ ID NO 278
<211> LENGTH: 9
<212> TYPE: PRT
<213> ORGANISM: Streptococcus pneumoniae

<400> SEQUENCE: 278

Ala Asn Tyr Gly Val Ser Ala Asp Lys
1               5

<210> SEQ ID NO 279
<211> LENGTH: 15
<212> TYPE: PRT
<213> ORGANISM: Streptococcus pneumoniae

<400> SEQUENCE: 279

Ala Val Ser Ala Ile Leu Gly Glu Leu Asn Gly Asn Glu Gly Lys
1               5                   10                  15

<210> SEQ ID NO 280
<211> LENGTH: 15
<212> TYPE: PRT
<213> ORGANISM: Streptococcus pneumoniae

<400> SEQUENCE: 280

Leu Met Asp Val Ala Gln Pro Glu Leu Ala Ile Val Phe Gly Arg
1               5                   10                  15
```

BIOMARKERS FOR DETECTING MICROBIAL INFECTION

STATEMENT OF PRIORITY

This application is a 35 U.S.C. § 371 national phase application of International Application No. PCT/EP2019/061462, filed May 3, 2019, which claims priority to Great Britain Patent Application No. 1807380.9, filed May 4, 2018, the entire contents of each of which is incorporated by reference herein in its entirety.

STATEMENT REGARDING ELECTRONIC FILING OF A SEQUENCE LISTING

A Sequence Listing in ASCII text format, submitted under 37 C.F.R. § 1.821, entitled 9737-83seqlist_ST25.txt, 62,194 bytes in size, generated on Nov. 19, 2021 and filed via EFS-Web, is provided in lieu of a paper copy. This Sequence Listing is incorporated by reference into the specification for its disclosures.

FIELD OF THE INVENTION

This invention relates to the identification of specific biomarkers for microbial infection, e.g., bacterial infection, e.g. respiratory tract infections, and their use in detecting microbes/bacteria in a sample, such as detecting respiratory tract infections directly in clinical samples.

BACKGROUND OF THE INVENTION

Correct and effective diagnosis and treatment of patients suffering from infections is an ever-present goal in healthcare, impacting both socio-economic factors but also mortality rates in cases of severe infections. With the increased attention to microbes/bacteria displaying multi-resistance and virulence traits, tools and methods responding to meet the need of better diagnostics are continuously being developed and tested. The more established and commonly used methods involve traditional cultivation-based methods and profiling based on phenotypes, but also polymerase chain reaction (PCR) assays and DNA sequencing of biomarker genes for genotype classification. Motivations to remove some of the inherent drawbacks of these methods includes automation (less manual labor) and increased speed, which has resulted in development of so-called next-generation sequencing (NGS) tools. This has also significantly impacted on the analysis cost very positively.

Still, both traditional and newer technologies often lack information about gene expression levels, and therefore current diagnostics and assays are trending towards looking also at the expressed genome, i.e. the proteome, for more in-depth analysis and characterization and typing of microbes/bacteria. During the last decade, mass spectrometry has emerged as an important tool in the clinic for characterization and typing of microbes/bacteria with the implementation of MALDI-TOF instruments. This technique is very rapid and accurate down to a certain level of information, including what species is present in the sample. Still, in general both MALDI-TOF and other currently implemented technologies based on sequencing approaches benefit significantly from isolating and culturing the microbes/bacteria prior to analysis and characterization from the patient samples, and in many cases the isolation and culturing step is a pre-requisite in order to perform the analysis. In order to further increase the speed of analysis and diagnosis, and also provide a more in-depth level of information about the infecting microbes/bacteria, new methods are still needed.

One of the most common causes of hospital visits are respiratory tract infections. Difficulties to accurately judge whether the infection is bacterial or non-bacterial (i.e. viral or fungal infections) based on fever and other symptoms may lead to over-prescription of antibiotics and the use of broad spectrum antibiotics as common practice, especially in cases of milder respiratory tract infections. Additional tests are usually needed to confirm the infectious agent, often including a culturing step, and this step may further force doctors to prescribe antibiotics "just-in-case". This may lead to contributing to the spread of antibiotic resistance, and also increased risk for patients for other adverse events with the treatment.

Knowledge of the identity of a pathogen causing disease facilitates adequate medical treatment, and, e.g., in clinical settings, information about the identity of a microbe/bacterium can be particularly useful. For example, knowledge regarding the identity of microbe/bacterium causing an infection can help to guide treatment decisions. A quick decision on the most suitable antimicrobial treatment can significantly shorten the duration of the infection and in some cases, such as *meningitides* or sepsis, potentially be life-saving.

Respiratory tract infections are one of the leading causes of death, causing several million deaths worldwide. Viral infection cause the majority of acute respiratory tract infections, but bacterial infections are also a significant cause, including infections by *Streptococcus pneumoniae, Staphylococcus aureus, Haemophilus influenzae, Moraxella catarrhalis, Chlamydia pneumoniae, Mycoplasma pneumoniae, Klebsiella pneumoniae, Escherichia coli,* and/or *Pseudomonas aeruginosa. Streptococcus pneumoniae* is a human pathogen and one of the most common causes of bacteremia, *pneumoniae*, meningitis in young children, leading to hundreds of deaths in USA and Europe, and pneumococcal *pneumoniae* is the most common community-acquired bacterial pneumonia (approx. 100 per 100000 adults each year).

A method of typing and characterization of microbes such as bacteria using bottom-up tandem mass-spectrometry proteomics is disclosed by Boulund et al. in Molecular & Cellular Proteomics 16.6, pages 1052-1063 (2017). The method, called "TCUP" compares the generated peptide sequence data to reference databases.

The listing or discussion of an apparently prior-published document in this specification should not necessarily be taken as an acknowledgement that the document is part of the state of the art or is common general knowledge.

DISCLOSURE OF THE INVENTION

The inventors have developed methods for detecting and/or identifying microbes and/or microbial biomarkers, e.g. bacteria and/or bacterial biomarkers. In particular, they have developed a method to detect specific biomarker sequences originating from microbes, such as bacteria in samples, e.g. clinical samples, using, e.g., mass spectrometry. Preferably, such biomarker sequences are peptides.

Thus, there is provided a method or diagnostic assay to detect specific biomarker peptides from microbes/bacteria in clinical samples using mass spectrometry. The specific biomarker peptides may be generated by proteolytic digestion of microbial/bacterial proteins. They may be identified by any suitable means, e.g. mass spectrometry analysis. The methods provided herein do not require a step of culturing microbes/bacteria prior to the biomarker detection step. Thus, they may advantageously be carried out on a sample that has not been cultured.

Embodiments and preferred embodiments of the invention are defined in the claims.

The invention provides a method of detecting or identifying a microbial/bacterial biomarker in a sample, wherein said microbial/bacterial biomarker is a peptide selected from the list of peptides 1-50 of Table 5, peptides 1-48 of Table 6, peptides 1-50 of Table 7, peptides 1-50 of Table 8, and/or peptides 1-50 of Table 9. The invention also provides a method of detecting or identifying a microbial/bacterial biomarker in a sample, wherein said microbial/bacterial biomarker is a peptide selected from those disclosed in Table 2 and/or 3. More preferably, said microbial/bacterial biomarker is a peptide selected from the list of peptides of table 10, peptides of table 11, peptides of table 12, and/or peptides of table 13. More preferably, said microbial/bacterial biomarker is a peptide selected from the list of peptides of table 14, 15, 16, and/or 17.

Any reference herein to a microbial biomarker should be understood to encompass, and preferably be, a bacterial biomarker, particularly a bacterial biomarker selected from the list of peptides 1-50 of Table 5, peptides 1-48 of Table 6, peptides 1-50 of Table 7, peptides 1-50 of Table 8, and/or peptides 1-50 of Table 9. Alternatively or in addition, the microbial biomarker may be a peptide selected from those disclosed in Table 2 and/or 3. More preferably, said microbial/bacterial biomarker is a peptide selected from the list of peptides of table 10, peptides of table 11, peptides of table 12, and/or peptides of table 13. More preferably, said microbial/bacterial biomarker is a peptide selected from the list of peptides of table 14, 15, 16, and/or 17.

The shorthand "microbes/bacteria" and derivatives thereof, such as "microbial/bacterial" should be understood to mean a microbe, which may be a bacterium.

The method may be used to detect and/or confirm the presence of microbes/bacteria in a sample.

The method may be used to identify a microbe/bacterium in a sample. Thus, it may be used to determine and/or confirm whether a particular type of microbe/bacterium is present in the sample. More particularly, it may be used to determine and/or confirm that a particular type of microbe/bacterium is present or absent in the sample.

The method may involve detecting a microbial/bacterial biomarker using mass spectrometry and/or an affinity reagent specific for the biomarker.

The microbial/bacterial biomarker may be indicative of the presence of a microbe/bacterium in the sample. Preferably, the biomarker may be indicative of the presence of a specific type of microbe/bacterium. Preferably, the biomarker may be discriminatory for a specific type of microbe/bacterium. Thus, the method may, e.g., be used to detect and/or identify a microbe/bacterium in the sample. The identification may, e.g., be at the family, genus, species, sub-species, or strain level. Preferably, it is at the family, genus or species level, e.g. the genus level or the species level.

It should be understood that any of the methods provided herein for detecting a microbial/bacterial biomarker in a sample are also suitable for determining that the sample contains microbes/bacteria (or contained microbes/bacteria prior to being processed for analysis via the method provided herein) and/or for detecting or diagnosing a microbial/bacterial infection of the sample/the subject from whom the sample is derived. Thus, any of the methods of detecting a microbial/bacterial biomarker are alternatively viewed as methods of detecting microbes/bacteria, methods of detecting a microbial/bacterial infection, and/or methods of diagnosing a microbial/bacterial infection. As mentioned elsewhere herein, preferably the identity of a specific type of microbe/bacterium is detected/determined/diagnosed.

Similarly, any of the methods provided herein for detecting a microbe/bacterium in a sample are also suitable for determining that the sample contains microbes/bacteria and/or for detecting or diagnosing a microbial/bacterial infection of the sample. Thus, any of the methods of detecting microbes/bacteria are alternatively viewed as methods of detecting a microbial/bacterial infection, and/or methods of diagnosing a microbial/bacterial infection, and/or methods of measuring, determining or detecting the presence or level of one or more biomarker peptides as described herein.

The biomarker peptide may be generated by proteolytic digestion of microbial/bacterial proteins. Thus, the method may include a step of proteolysis prior to the detection step. A proteolysis step may break one or more proteins down into one or more peptides, thereby generating peptides that may be biomarker peptides. However, certain biomarker peptides may be naturally present within the microbe/bacterium, displayed on its surface, and/or secreted by the microbe/bacterium. For example, a biomarker peptide may be part of a larger polypeptide or protein and be an epitope for an affinity reagent. The epitope is preferably accessible to the affinity agent when the protein is intact in native and/or denatured form. Therefore, a step of proteolysis may not necessarily be required and in some embodiments, the method does not include a step of proteolysis.

The microbial/bacterial biomarkers mentioned above were identified through a novel process devised by the present inventors, which involves the identification and selection of specific biomarker peptides through bioinformatics processing of mass spectrometry data. More particularly, the method of biomarker identification may include several approaches including bioinformatics (i.e. comparing the genomes of microbial/bacterial species and identifying specific proteins and protein fragments, such as peptides, that are unique to the microbial/bacterial species); and experimentally verified identification of such proteins, protein fragments and/or peptides using cultures of microbes/bacteria and/or spiked clinical samples in order to optimize the sample processing and mass spectrometry analysis; and/or detection of such biomarker peptides directly in processed clinical samples.

Certain methods of identifying potential peptide biomarkers of microbial taxonomy are known in the art. However, the prior art approaches sometimes have limited sensitivity, so there is a risk that they may not be sufficiently sensitive accurately to detect/identify microbes in a complex sample, such as a clinical specimen.

For example, a process involving bottom-up tandem mass spectrometry proteomics and bioinformatics is known in the art as "TCUP" and details thereof are provided in Boulund et al. supra. TCUP relies on curated genomic databases and when a tandem mass spectra is matched to a peptide sequence it uses the algorithm Lowest Common Ancestor (LCA) to find unique peptides for different levels of taxonomy (Family, Genus, Species). In essence, a pan-genomic approach, finding nucleotide sequences that differ between different species, thus identifying gene-markers, enables the discovery of possible genetic markers. The same can be seen in translating these nucleotide sequences into peptide sequences.

The present invention provides an advantageous method of identifying peptide biomarkers of microbial/bacterial taxonomy, e.g. peptide biomarkers specific for a first microbial/bacterial species. The method involves the experimental verification of putative biomarkers.

Thus, in a further related aspect of the invention, there is provided a method of identifying a set of peptide biomarkers specific for a first microbial/bacterial species, said method comprising experimental verification of a first set of biomarkers. The first set of biomarkers may be considered to be a set of putative or preliminary biomarkers. The experimental verification of a biomarker may include mass spectrometric analysis of a clinical sample spiked with the first microbial/bacterial species. Alternatively or in addition, it may include mass spectrometric analysis of a (non-spiked) clinical sample previously determined to be positive for the first microbial/bacterial species.

Exemplary flowcharts of suitable methods are provided in FIGS. 1, 2, 3 and 6, but these are for illustrative purposes only and are not limiting.

The experimental verification of the biomarkers may be used to revise the first set of (putative) peptide biomarkers, thereby generating a second set of peptide biomarkers.

The experimental verification may typically involve determining whether a putative peptide biomarker for a first microbial/bacterial species can reliably be detected in a clinical sample comprising the first microbial/bacterial species. The set of biomarkers may be revised accordingly.

The revision may involve the removal of a putative peptide biomarker from the set of biomarkers, e.g. if the putative peptide biomarker cannot reliably be detected in the clinical sample. Alternatively or in addition, it may involve the addition of a putative peptide biomarker to the set of biomarkers, e.g. if a putative peptide biomarker can reliably be detected in the clinical sample. Alternatively or in addition, it may involve the retention of a putative peptide biomarker in the set of biomarkers, e.g. if the putative peptide biomarker can reliably be detected in the clinical sample it may be retained in the set of biomarkers and may optionally be given a higher ranking than prior to the experimental verification step.

Preferably, there is provided a method of identifying a peptide biomarker, or set of peptide biomarkers, specific for a first microbial/bacterial species, said method comprising
(a) mass spectrometric analysis of a plurality of peptides from a first microbial/bacterial species to generate mass spectral data;
(b) analyzing the mass spectral data to match it to peptide sequence identities, thereby generating peptide sequence data;
(c) comparing the generated peptide sequence data to a reference database to map the peptides to reference genome sequences;
(d) identifying peptides that are putative biomarkers for the first microbial species;
(e) ranking the peptides of step (d) and selecting the top ranked peptides to generate a first set of peptide biomarkers suitable for detecting/identifying the first microbial/bacterial species; and
(f) experimentally verifying one or more of the biomarkers included in the set of peptide biomarkers generated in step (e) to identify a peptide biomarker, or generate a revised set of peptide biomarkers, suitable for detecting/identifying the first microbial/bacterial species.

Steps (a) and (b) may be carried out using simulated data generated by in silico peptide digestion and/or using experimental proteomics data generated by tandem mass spectrometry as explained in Boulund et al. supra.

Step (c) may comprise aligning the peptide sequence data to the complete genomes of one or more microbial/bacterial species translated into all six reading frames and applying filtering steps as explained in Boulund et al. supra.

Step (e) may involve carrying out steps (a) to (d) two or more times, e.g. 2-20 or 8-15 times, e.g. about 10 times and ranking the peptides according to how reliably they were identified in step (d).

Step (f) may, for example, comprise
(i) mass spectrometric analysis of a plurality of peptides in a clinical sample spiked with the first microbial/bacterial species; and revising the set of peptide biomarkers to generate a revised set of peptide biomarkers.

Alternatively or in addition, step (f) may, for example, comprise
(ii) mass spectrometric analysis of a plurality of peptides in a clinical sample known to be infected with the first microbial/bacterial species; and revising the set of peptide biomarkers to generate a revised set of peptide biomarkers.

If the method comprises both steps (i) and (ii), these steps may be in any suitable order. Thus, step (i) may precede step (ii) and/or it may be subsequent to step (ii).

It must be appreciated that the set of biomarkers which is revised will depend on the steps that the method comprises. Thus, the set of biomarkers which is revised may be the first set of peptide biomarkers generated in step (e), or it may be the revised set of biomarkers generated in step (i), or the revised set of biomarkers generated in step (ii).

The set of biomarkers identified via any of the methods described above (or indeed any other biomarker or set of biomarkers as described herein) may be considered to be an "inclusion list".

Inclusion lists may be used during mass spectrometric analysis. A peptide inclusion list may be considered to be instructions for the mass spectrometer to look for the selected set of masses corresponding to the peptides in the inclusion list. An inclusion lists can be used in various different modes of action. For example, an "inclusion list" mode instructs the mass spectrometer only to look for the selected set of masses corresponding to the peptides in the inclusion list. An "inclusion list plus pick others" mode instructs the mass spectrometer to first look for the masses in the inclusion list and pick them for fragmentation; however, if the mass spectrometer does not find the masses in the inclusion list, it will "pick other" ions for fragmentation, usually the top ten most intense ions. The use of an inclusion list may be beneficial if the sample is complex, such as a clinical sample containing both human and microbial/bacterial sources of proteins from which peptides may originate.

Thus, inclusion lists may be used in targeted MS analysis in order to enhance the detection probability of the peptides in the inclusion list, thus lowering the detection limit of the peptides and thereby increasing the sensitivity of the analysis of the sample.

There is provided a peptide biomarker inclusion list prepared according to the method of the invention. There is provided a peptide biomarker inclusion list suitable for the targeted mass spectrometric identification of *Streptococcus pneumoniae, Staphylococcus aureus, Haemophilus influenzae, Escherichia coli*, or *Moraxella catarrhalis*.

Provided is a peptide biomarker inclusion list suitable for the targeted mass spectrometric identification of *Moraxella catarrhalis* which comprises or consists of exactly, about, or at least, 1, 2, 3, 4, 5, 6, 7, 8, 9, 10, 15, 20, 25, 30, 35, 40, 45 or 50, or all of the peptides of Table 5, 11, or 15, and optionally variants thereof, preferably as defined below. Alternatively or in addition, said biomarker inclusion list may comprise or consist of one or more of the *Moraxella catarrhalis* biomarkers disclosed in Table 2.

Provided is a peptide biomarker inclusion list suitable for the targeted mass spectrometric identification of *Haemophilus influenza* which comprises or consists of exactly, about, or at least, 1, 2, 3, 4, 5, 6, 7, 8, 9, 10, 15, 20, 25, 30, 35, 40, 45 or 50, or all of the peptides of Table 6, 12 or 16, and optionally variants thereof, preferably as defined below. Alternatively or in addition, said biomarker inclusion list may comprise or consist of one or more of the *Haemophilus influenza* biomarkers disclosed in Table 2.

Provided is a peptide biomarker inclusion list suitable for the targeted mass spectrometric identification of *Staphylococcus aureus* which comprises or consists of exactly, about, or at least, 1, 2, 3, 4, 5, 6, 7, 8, 9, 10, 15, 20, 25, 30, 35, 40, 45 or 50, or all of the peptides of Table 7, 10 or 14, and optionally variants thereof, preferably as defined below. Alternatively or in addition, said biomarker inclusion list may comprise or consist of one or more of the *Staphylococcus aureus* biomarkers disclosed in Table 2.

Provided is a peptide biomarker inclusion list suitable for the targeted mass spectrometric identification of *Streptococcus pneumonia* which comprises or consists of exactly, about, or at least, 1, 2, 3, 4, 5, 6, 7, 8, 9, 10, 15, 20, 25, 30, 35, 40, 45 or 50, or all of the peptides of Table 8, 13, or 17, and optionally variants thereof, preferably as defined below. Alternatively or in addition, said biomarker inclusion list may comprise or consist of one or more of the *Streptococcus pneumonia* biomarkers disclosed in Table 2 and/or 3.

Provided is a peptide biomarker inclusion list suitable for the targeted mass spectrometric identification of *Escherichia coli* which comprises or consists of exactly, about, or at least, 1, 2, 3, 4, 5, 6, 7, 8, 9, 10, 15, 20, 25, 30, 35, 40, 45 or 50, or all of the peptides of Table 9 and optionally variants thereof, preferably as defined below.

Any reference herein to a "biomarker inclusion list" should be understood to encompass and preferably be a biomarker inclusion list prepared according to the method provided herein, more preferably a biomarker inclusion list as defined above by reference to Table 5, 6, 7, 8, 9, 10, 11, 12, 13, 14, 15, 16, and/or 17, respectively, and/or by reference to Table 2 or 3 respectively.

Also provided is a peptide biomarker inclusion list suitable for the targeted mass spectrometric identification of two or more different bacteria selected from *Moraxella catarrhalis, Haemophilus influenza, Staphylococcus aureus, Streptococcus pneumonia,* and *Escherichia coli*, which comprises or consists of exactly, about, or at least, 1, 2, 3, 4, 5, 6, 7, 8, 9, 10, 15, 20, 25, 30, 35, 40, 45 or 50, or all of the peptides of Table 5, 11, or 15, and optionally variants thereof, preferably as defined below; exactly, about, or at least, 1, 2, 3, 4, 5, 6, 7, 8, 9, 10, 15, 20, 25, 30, 35, 40, 45 or 50, or all of the peptides of Table 6, 12, or 16, and optionally variants thereof, preferably as defined below; exactly, about, or at least, 1, 2, 3, 4, 5, 6, 7, 8, 9, 10, 15, 20, 25, 30, 35, 40, 45 or 50, or all of the peptides of Table 7, 10 or 14, and optionally variants thereof, preferably as defined below; exactly, about, or at least, 1, 2, 3, 4, 5, 6, 7, 8, 9, 10, 15, 20, 25, 30, 35, 40, 45 or 50, or all of the peptides of Table 8, 13, or 17, and optionally variants thereof, preferably as defined below; exactly, about, or at least, 1, 2, 3, 4, 5, 6, 7, 8, 9, 10, 15, 20, 25, 30, 35, 40, 45 or 50, or all of the peptides of Table 9 and optionally variants thereof, preferably as defined below; and/or one or more or all of the peptides of Table 2 and/or 3.

Such combinations of inclusion list may be useful for detecting co-infection of two or more (e.g. three, four or five) different bacteria selected from *Moraxella catarrhalis, Haemophilus influenza, Staphylococcus aureus, Streptococcus pneumonia,* and *Escherichia coli*. Indeed, preferred embodiments of the methods of the invention can be used to detect or identify two or more (e.g. three, four or five) different bacteria selected from *Moraxella catarrhalis, Haemophilus influenza, Staphylococcus aureus, Streptococcus pneumonia,* and *Escherichia coli* in the same sample. Again, such methods can thereby be used to detect co-infections. In such methods and inclusion lists, appropriate peptides (or proteins) or inclusion lists to use (or combine) can be selected depending on the different types of bacteria to be detected or identified, e.g. in a potential coinfection, e.g. can be selected based on the Tables and inclusion lists provided herein. Detection of two or more (e.g. 3 or 4) different bacteria selected from *Moraxella catarrhalis, Haemophilus influenza, Staphylococcus aureus* and *Streptococcus pneumonia*, is also provided.

Also provided is a method to detect a microbial/bacterial biomarker, microbe/bacterium or microbial/bacterial infection using a biomarker inclusion list, wherein said method is characterised by using a biomarker inclusion list as provided herein to perform targeted mass spectrometric analysis of a sample.

Figure 7:
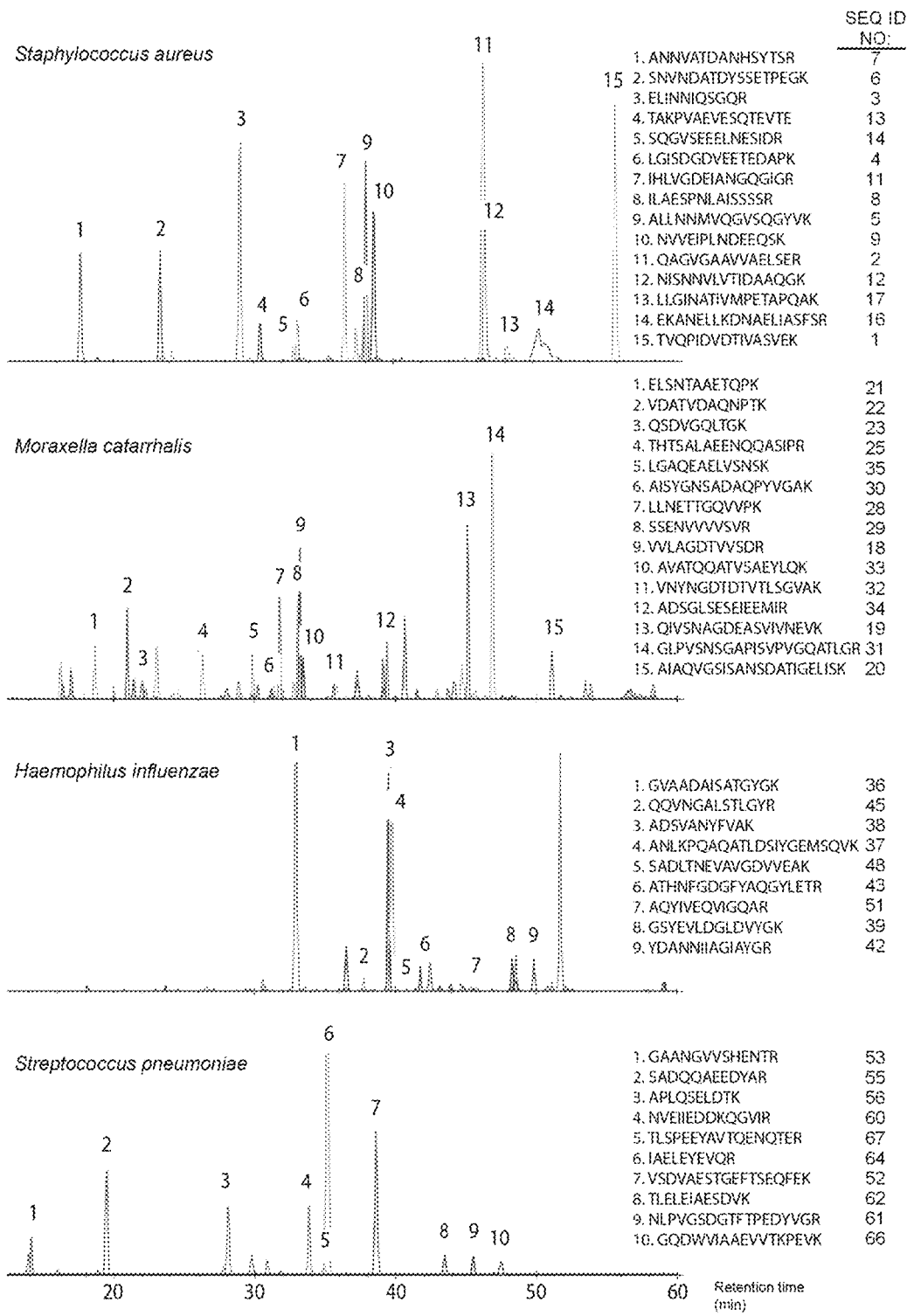

Also provided is to perform a parallel reaction monitoring (PRM) method with increased sensitivity and high selectivity by targeting the most appropriate species-unique peptides identified in the verification phase (Tables 10-13 and Tables 14-17). The peptide identities were verified by matching their fragment patterns to a spectral library containing annotated reference fragment spectra from the qualification and verification phases. Matching against spectra libraries, combined with correction for retention time and mass accuracy, provided high selectivity and sensitivity (FIG. 7). An advantage of the targeted PRM approach is that no advanced database matching is required to confirm the presence of already known peptides in clinical samples.

Also provided is software comprising instructions to cause a computer to carry out this method.

Also provided is a system for use in detecting a microbial/bacterial biomarker, microbe/bacterium or microbial/bacterial infection, said system comprising a computer carrying the software provided herein, or otherwise programmed to carry out the method to detect a microbial/bacterial biomarker, microbe/bacterium or microbial/bacterial infection, e.g. using a biomarker inclusion list as provided herein.

Also provided is a computer readable medium comprising the software provided herein to carry out the method to detect a microbial/bacterial biomarker, microbe/bacterium or microbial/bacterial infection using a biomarker inclusion list as provided herein and/or which comprises a digitally encoded biomarker inclusion list.

Also provided is use of the software, system, or computer readable medium as provided herein to detect a microbial/bacterial biomarker, microbe/bacterium or microbial/bacterial infection.

There is also provided a set of peptides comprising or consisting of 2-50, 3-50, 5-50, 10-50 or 20-50 (e.g. any integer between 2 and 50, or all peptides of a particular list, more preferably 2, 3, 4, 5, 6, 7, 8, 9, or 10, or up to 15 or 20, more preferably 1, 2, 3, 4 or 5) different peptides (a) to (e), (j) or (k), or different peptides (f-i), selected from (a) the peptides listed in Table 5 and optionally variants thereof, preferably as defined below;
(b) the peptides listed in Table 6 and optionally variants thereof, preferably as defined below;
(c) the peptides listed in Table 7 and optionally variants thereof, preferably as defined below;
(d) the peptides listed in Table 8 and optionally variants thereof, preferably as defined below;
(e) the peptides listed in Table 9 and optionally variants thereof, preferably as defined below;
(f) the peptides listed in Table 10 and optionally variants thereof, preferably as defined below;
(g) the peptides listed in Table 11 and optionally variants thereof, preferably as defined below;
(h) the peptides listed in Table 12 and optionally variants thereof, preferably as defined below;
(i) the peptides listed in Table 13 and optionally variants thereof, preferably as defined below;
(j) the peptides listed in Table 2 and optionally variants thereof, preferably as defined below; or
(k) the peptides listed in Table 3 and optionally variants thereof, preferably as defined below.
  Other preferred sets of peptides are provided in Tables 14 to 17. Combinations of these sets are also provided, e.g. combinations of the peptides listed in Tables 10 to 13 or Tables 14 to 17, with one or more of the lists of peptides in Tables 5, 6, 7, 8 or 9.

The set is particularly suitable for detecting/identifying a single type of microbe/bacterium in a sample, preferably a clinical sample. The type of microbe/bacterium is preferably selected from *Moraxella catarrhalis, Haemophilus influenza, Staphylococcus aureus, Streptococcus pneumonia*, and *Escherichia coli*.

Preferably the set comprises or consists of at or at least 1, 2, 3, 4, 5, 6, 7, 8, 9, 10, 15, 20, 30, 40, 45, 48 or all different peptides as defined above, e.g. about 5, 10, 20, 30, 40, 48 or 50. Preferably the set comprises or consists of 1, 2, 3, 4, 5, 6, 7, 8, 9, or 10, or up to 15 or 20, more preferably 1, 2, 3, 4 or 5 different peptides, e.g. selected from the above lists (a) to (k) or selected from the Tables 5-9, preferably Tables 10-13, more preferably Tables 14-17. Preferably, the set comprises no more than 20, 10, 5, 4, 3, 2 or 1 peptides that are not listed in the Table 5, 6, 7, 8, 9, respectively that the peptides are selected from. Preferably, it does not comprise any peptides that are not listed in Table 5, 6, 7, 8, or 9, respectively that the peptides are selected from. Thus, if the set comprises peptides selected from Table 5, it preferably does not comprise any peptides selected from Table 6, 7, 8, or 9.

There is also provided a set of peptides comprising or consisting of 2-50, 3-50, 5-50, 10-50 or 20-50 (e.g. any integer between 2 and 50, or all peptides of a particular list, more preferably 2, 3, 4, 5, 6, 7, 8, 9, or 10, or up to 15 or 20, more preferably 1, 2, 3, 4 or 5) different peptides (a) to (e), (j) or (k), or different peptides (f-i), selected from
(a) the peptides listed in Table 5 and optionally variants thereof, preferably as defined below;
(b) the peptides listed in Table 6 and optionally variants thereof, preferably as
(c) the peptides listed in Table 7 and optionally variants thereof, preferably as defined below;
(d) the peptides listed in Table 8 and optionally variants thereof, preferably as defined below;
(e) the peptides listed in Table 9 and optionally variants thereof, preferably as defined below;
(f) the peptides listed in Table 10 and optionally variants thereof, preferably as defined below;
(g) the peptides listed in Table 11 and optionally variants thereof, preferably as defined below;
(h) the peptides listed in Table 12 and optionally variants thereof, preferably as defined below;
(i) the peptides listed in Table 13 and optionally variants thereof, preferably as defined below;
(j) the peptides listed in Table 2 and optionally variants thereof, preferably as defined below; and
(k) the peptides listed in Table 3 and optionally variants thereof, preferably as defined below.
  Other preferred sets of peptides are provided in Tables 14 to 17. Combinations of these sets are also provided, e.g. combinations of the peptides listed in Tables 10 to 13 or Tables 14 to 17, with one or more of the lists of peptides in Tables 5, 6, 7, 8 or 9. Appropriate and preferred numbers of peptides to be included in the set are described elsewhere herein.

The set is particularly suitable for detecting/identifying two or more different types of microbe/bacterium in a sample, preferably a clinical sample. The types of microbe/bacterium are preferably selected from *Moraxella catarrhalis, Haemophilus influenza, Staphylococcus aureus, Streptococcus pneumonia*, and *Escherichia coli*.

Preferably, the set comprises peptides from 2 or more of (a) to (k), more preferably (a) to (i) e.g. peptides from 2-5, 2-3, 2-4, 3-5, or 3-4 of (a) to (k) or (a) to (i), e.g. at least one peptide selected from (b) and at least one peptide selected from (c); or at least one peptide selected from each of (a) to (k) or (a) to (i).

The above sets of peptides, or other individual peptides or sets of peptides as described elsewhere herein, can also be used for detection or identification of the presence of said peptides or the proteins from which said peptides derive in a sample, for example a clinical sample or any other sample as described elsewhere herein. Thus, such peptides or sets of peptides as described herein can be used in detection or diagnostic kits of the invention. In such detection or identification methods, conveniently the peptides or sets of peptides can be attached to a solid support or immobilized as described elsewhere herein, for example presented in an array (peptide array), e.g. printed array (see for example https://www.pepperprint.com/products/pepperchipr-custom-microarrays/), for example on a chip or biochip.

These peptides or sets of peptides can then be used to detect the presence of peptides or proteins in a clinical sample by for example detecting an elicited immune response towards one or more of the peptide biomarkers which is prompted by a bacterial infection. In this regard, during an infection the immune system produces antibodies against the pathogens of the infection. Some of the antibodies will thus likely be directed towards proteins from which the peptide biomarkers of the present invention originate, or even directly towards the specific peptide sequences themselves, for example within the proteins. Thus, a sample, for example a clinical sample such as a serum or plasma sample, which will potentially contain such antibodies, could be applied to the peptides or sets of peptides of the invention, for example when presented on a solid support or array, and the binding of antibodies towards the biomarker peptides could be measured or detected. If there is binding of antibodies to one or more of the biomarker peptides, this would suggest the presence of an infection of the pathogen from which the biomarker peptides originate. Thus, this can be used for detecting, identifying or diagnosing infection in accordance with the invention, advantageously with potential for use at the point of care. Such point-of-care assays, which are enabled by the use of arrays or affinity reagents as described elsewhere herein, are preferred in some embodiments.

There is also provided a peptide comprising or consisting of an amino acid sequence selected from the amino acid sequences of
  (a) the peptides listed in Table 5 and optionally variants thereof, preferably as defined below;
  (b) the peptides listed in Table 6 and optionally variants thereof, preferably as defined below;
  (c) the peptides listed in Table 7 and optionally variants thereof, preferably as defined below;
  (d) the peptides listed in Table 8 and optionally variants thereof, preferably as defined below;
  (e) the peptides listed in Table 9 and optionally variants thereof, preferably as defined below;
  (f) the peptides listed in Table 10 and optionally variants thereof, preferably as defined below;
  (g) the peptides listed in Table 11 and optionally variants thereof, preferably as defined below;
  (h) the peptides listed in Table 12 and optionally variants thereof, preferably as defined below;
  (i) the peptides listed in Table 13 and optionally variants thereof, preferably as
  (j) the peptides listed in Table 2 and optionally variants thereof, preferably as defined below; and/or
  (k) the peptides listed in Table 3 and optionally variants thereof, preferably as defined below.
    Other preferred peptides are provided in Tables 14 to 17.

The variant may be a peptide comprising or consisting of a fragment of one of the peptides disclosed in any one of Tables 5-13, 14-17, 2 and/or 3, preferably Tables 5-13 or 14-17. Preferably, such a variant comprises a fragment of at least 4, 5, 6, 7, 8, 9 or 10 continuous amino acids of one of the peptide sequences disclosed in any one of Tables 5-9, 14-17, 2 and/or 3, preferably Tables 5-13 or 14-17. Preferably, the variant amino acid sequence consists of exactly, about or no more than 50, 40, 30, 25, 20, 19, 18, 17, 16, 15, 14, 13, 12, 11, 10, 9, 8, 7, 6 or 5 amino acids.

Alternatively or in addition, the variant may comprise or consist of an amino acid sequence having at least 75, 80, 85, 90, 95, 98 or 99% sequence identity with the amino acid sequence of any one of the peptides disclosed in any one of Tables 5-13, 14-17, 2 or 3, preferably Tables 5-13 or 14-17, e.g. with SEQ ID NO: 52 or SEQ ID NO: 171.

Alternatively or in addition, the variant comprise or consist of an amino acid sequence having 1-5 amino acid substitutions, additions and/or deletions, e.g. 1-4, 1-3 or 1-2, e.g. 1 or less than 2, compared to the amino acid sequence of any one of the peptides disclosed in any one of Tables 5-13, 14-17, 2 or 3, preferably Tables 5-13, or 14-17 e.g. SEQ ID NO: 52 or SEQ ID NO: 171. The substitutions may be conservative amino acid substitutions, non-conservative amino acid substitutions, or a mix thereof. Preferably, only conservative amino acid substitutions are present.

The variant preferably consists of no more than 50, 40, 30, 25, 24, 23, 22, 21, 20, 19 or 18 amino acids. If the peptide comprises SEQ ID NO: 171 it may, e.g., consist of 16 or 17 amino acids.

The peptide or variant thereof is preferably isolated, synthetic or recombinant.

Also provided is a peptidomimetic which is a mimetic of any of the peptides provided herein, such as any one of the peptides disclosed in any one of Tables 5-13, 14-17, 2 or 3, preferably Tables 5-13 or 14-17.

Also provided is a kit comprising one or more of the peptide biomarker sets provided herein and/or one or more of the peptides provided herein and/or one or more of the peptidomimetics provided herein, e.g. a kit comprising or consisting of at or at least 1, 2, 3, 4, 5, 6, 7, 8, 9, 10, 15, 20, 30, 40, 45, 48 or all different peptides of a particular set as defined above, e.g. about 5, 10, 20, 30, 40, 48 or 50. Preferably the set comprises or consists of 1, 2, 3, 4, 5, 6, 7, 8, 9, or 10, or up to 15 or 20, more preferably 1, 2, 3, 4 or 5 different peptides, e.g selected from the above lists (a) to (k), or selected from the Tables 5-9, preferably Tables 10-13, more preferably Tables 14-17.

Also provided is a nucleic acid molecule encoding one or more of the biomarker peptides provided herein, e.g. one or more of the peptides provided herein.

Also provided is the complement of such a nucleic acid molecule.

Also provided is a vector comprising a nucleic acid molecule as provided herein. Preferably, the vector comprises a promoter sequence operably linked to the sequence encoding a peptide provided herein.

Also provided is a host cell comprising such a peptide, nucleic acid molecule, and/or vector. Also provided is a kit comprising a nucleic acid molecule, vector, host, peptide and/or peptide set as provided herein.

Also provided is an affinity reagent that can specifically bind to one of the biomarker peptides provided herein, preferably to one of the peptides provided herein, most preferably to one of the peptides listed in Tables 5 to 9, preferably Tables 10 to 13, more preferably Tables 14 to 17, or one of the proteins listed in Tables 10 to 17. Sets of such affinity reagents are also provided, e.g. sets comprising or consisting of 2-50, 3-50, 5-50, 10-50 or 20-50 (e.g. any integer between 2 and 50, or all peptides of a particular list), more preferably 1, 2, 3, 4, 5, 6, 7, 8, 9, or 10, or up to 15 or 20, more preferably 1, 2, 3, 4 or 5 different peptides. Sets of affinity reagents that can specifically bind to a set of peptides or set of proteins as described herein (e.g. sets based on the peptides of Tables 5 to 9, preferably Tables 10 to 13, more preferably Tables 14 to 17, or sets based on the proteins described in Tables 10 to 13, preferably Tables 14 to 17) are also provided. A The nucleic acid molecule, vector, host cell or affinity reagent is preferably isolated, synthetic or recombinant.

The biomarker may preferably be present in, or derived from, a protein selected from (a) general stress protein 24 (Gls24); and (b) methionine adenosyltransferase (MetK-2), or any of the other proteins listed in Tables 10 to 13, preferably Tables 14 to 17. Thus, also provided is a method of detecting microbes/bacteria in a sample, preferably in a clinical specimen, comprising detecting a protein selected from (a) general stress protein 24 (Gls24); and (b) methionine adenosyltransferase (MetK-2) or any of the other proteins listed in Tables 10 to 13, preferably Tables 14 to 17.

Also provided is an affinity reagent that can specifically bind to a protein selected from (a) general stress protein 24 (Gls24); and (b) methionine adenosyltransferase (MetK-2) or any of the other proteins listed in Tables 10 to 13, preferably Tables 14 to 17.

The biomarker may be present in a secreted protein and/or a surface-exposed protein, thereby allowing the detection of microbes/bacteria without requiring a microbial/bacterial lysis and/or proteolysis step. Thus, also provided is a method of detecting microbes/bacteria in a sample, preferably in a clinical specimen, comprising detecting a secreted protein or a surface-exposed protein. The method may, e.g., be used to detect whole microbes/bacteria. The method may involve detecting the protein using an affinity reagent specific for the protein.

Affinity reagents (or sets of affinity reagents) can conveniently be provided as an array, e.g. in a printed array format.

Also provided is a diagnostic kit for detecting specific biomarker peptides, wherein the kit comprises an affinity reagent (or a set of affinity reagents) as provided herein. The kit may further comprise one or more reagents suitable for proteolysis of microbial/bacterial proteins; one or more cell lysis agents; and/or one or more additional components, such as a buffer.

For example, it may comprise a suitable protease, details of which are provided elsewhere herein; and/or a cell lysis agent such as lysis beads and/or a detergent.

Also provided is a diagnostic kit for detecting microbes/bacteria, which may be whole microbes/bacteria, wherein the kit comprises an affinity reagent specific for a protein selected from (a) general stress protein 24 (Gls24); and (b) methionine adenosyltransferase (MetK-2) or any of the other proteins listed in Tables 10 to 13, preferably Tables 14 to 17.

In the cases of S. pneumoniae and H. influenzae, the most prominent peptides originate from only a few proteins, whereas, for M. catarrhalis and S. aureus, the peptides derive from a variety of different proteins. For M. catarrhalis and S. aureus, many of the species-unique peptides originated from highly abundant cytosolic proteins, including ribosomal proteins. Since cytosolic house-keeping proteins, in general, are relatively highly expressed, regardless of growth conditions (e.g., ex situ cultivation or in vivo within a host), the most prominent species-unique peptides would most likely originate from the house-keeping proteins when analyzing clinical samples. These proteins are also used often as targets for identification, using traditional gene-based approaches, as well as MALDI-TOF MS.

In contrast, many of the proteins identified from the species-unique peptides for S. pneumoniae and H. influenzae include those associated with the surface of the cells. This might be due to the differences in taxonomic structure of the different species. M. catarrhalis and S. aureus are phylogenetically more distant from their closest related species; hence, their house-keeping proteins, including ribosomal proteins, do not display substantial overlap in amino acid sequences of the species closest to them. However, for S. pneumoniae and H. influenzae, the taxonomic structures around these species are more complex and the house-keeping proteins, including ribosomal proteins, display larger amounts of overlapping amino acid sequences, thus making it more difficult to find species-unique peptides from these proteins. Surface-associated proteins have different functions, helping the bacteria survive in diverse and dynamic ecological niches and, particularly, these proteins are often involved in host-pathogen interactions, effectively functioning, for example, as virulence factors. Many of the proteins identified from S. pneumoniae and H. influenzae by their respective species-unique peptides belong to the group of surface-associated virulence factors, which could be explained by the fact that these proteins are the ones differentiating them from their closest relatives, as well as being expressed significantly in clinical samples, making detection of these species-unique peptides possible.

Also provided is a pharmaceutical composition comprising a peptide, peptidomimetic, nucleic acid molecule, vector, host cell, or affinity reagent as provided herein. The pharmaceutical composition may be a vaccine.

Any of the detection methods provided herein may form part of a diagnostic method. Thus, provided is a method of diagnosis comprising detecting a microbial/bacterial biomarker in a sample, wherein said microbial/bacterial biomarker is a peptide selected from any one of the peptides disclosed in Tables 5-13, 14-17, 2 or 3, preferably Tables 5-9, preferably Tables 10-13, more preferably Tables 14-17, or a variant thereof as defined herein. As discussed elsewhere herein, said detection step may involve mass spectrometry and/or an affinity agent. Said method may comprise a step of making a determination whether microbes/bacteria, preferably a specific type of microbes/bacteria, are present in the sample and preferably on the basis of that determination making a diagnosis. Thus, a determination may be made that microbes/bacteria are present and on that basis a diagnosis of a microbial/bacterial infection may be made; or a determination may be made that microbes/bacteria are not present and on that basis a diagnosis of that no microbial/bacterial infection is present may be made.

Also provided is a method of diagnosis comprising detecting microbes/bacteria, preferably S. pneumoniae, Staphylococcus aureus, Haemophilus influenzae, Escherichia coli, and/or Moraxella catarrhalis in a sample, comprising detecting (a) general stress protein 24 (Gls24); and/or (b) methionine adenosyltransferase (MetK-2) or any of the other proteins listed in Tables 10 to 13 (as appropriate for the bacteria concerned), preferably Tables 14 to 17 (as appropriate for the bacteria concerned). As discussed elsewhere herein, said detection step may involve an affinity agent (or a set of affinity reagents). Said method may comprise a step of making a determination that S. pneumonia, Staphylococcus aureus, Haemophilus influenzae, Escherichia coli, and/or Moraxella catarrhalis, is present in the sample and preferably on the basis of that determination making a diagnosis.

It can be noted that for all embodiments of the invention described herein, alternative bacterial biomarkers for various bacteria are listed in Table 18.

In addition, other preferred peptide biomarkers for various bacteria are shown in FIG. 7. Other preferred peptide biomarkers for various bacteria are shown in Tables 10-13, more preferably Tables 14-17.

Also provided is a peptide, peptidomimetic, nucleic acid molecule, vector, host cell, affinity reagent or pharmaceutical composition as provided herein for use in diagnosis or therapy.

Thus, there is provided a method of diagnosis, comprising contacting a subject or a clinical specimen with an agent selected from a peptide, peptidomimetic, nucleic acid molecule, vector, host cell, affinity reagent, kit, or pharmaceutical composition as provided herein. The diagnostic method may be performed in vivo, ex vivo, or in vitro.

Also provided is a method of treatment, comprising administering to a subject in need thereof a therapeutically effective amount of an agent selected from a peptide, peptidomimetic, nucleic acid molecule, vector, host cell, affinity reagent, kit, or pharmaceutical composition as provided herein. Also provided is the use of an agent selected from a peptide, peptidomimetic, nucleic acid molecule, vector, host cell, affinity reagent, kit, or pharmaceutical composition as provided herein in the manufacture of a composition for use in diagnosis or therapy.

The treatment may be vaccination.

As used herein, the singular forms "a", "an" and "the" are intended to include the plural forms as well, unless the context clearly indicates otherwise. Also, as used herein, "and/or" refers to and encompasses any and all possible combinations of one or more of the associated listed items.

When a range is employed (e.g., a range from x to y) it is it meant that the measurable value is a range from about x to about y, or any range therein, such as about $x_1$ to about $y_1$, etc.

It will be further understood that the terms "comprises" and/or "comprising" when used herein specify the presence of stated features, integers, steps, operations, elements, and/or components, but do not preclude the presence or addition of one or more other features, integers, steps, operations, elements, components, and/or groups thereof.

Unless otherwise defined, all terms, including technical and scientific terms used herein, have the same meaning as commonly understood by one of ordinary skill in the art to which this invention belongs.

A microbe, also known as a micro-organism, is an organism which is too small to be visible to the naked eye, i.e. is microscopic. A microbe may be selected from bacteria, fungi, archaea, algae, protozoa, and viruses. Although the terms bacteria, fungi, archaea, algae, protozoa and viruses technically denote the plural form, it is common practice to use them also to denote the singular form. Consequently, the terms "microbes/bacteria" and "microbe/bacterium" are used interchangeably herein.

The microbe may be selected from bacteria, fungi, archaea, algae, virus and protozoa, preferably bacteria.

The microbe/bacterium may be a pathogen, e.g. a pathogen of the respiratory tract. For example, the microbe/bacterium may be selected from *Streptococcus pneumoniae, Staphylococcus aureus, Haemophilus influenzae, Moraxella catarrhalis, Chlamydia pneumoniae, Mycoplasma pneumoniae, Klebsiella pneumoniae, Escherichia coli,* and *Pseudomonas aeruginosa*. Preferably, it is selected from *Streptococcus pneumoniae, Staphylococcus aureus, Haemophilus influenzae, Escherichia coli,* and *Moraxella catarrhalis*.

Any reference herein to a "type of microbe" or "type of bacterium" means a microbe/bacterium of the desired type, which may be at the genus, species or strain level as desired. Thus, for example, if it is desired to determine whether any members of the genus *Staphylococcus* are present in a sample, the type of bacterium is the genus *Staphylococcus*; whereas if it is desired to determine whether any members of the species *Staphylococcus aureus* are present in a sample, the type of bacterium is the species *Staphylococcus aureus*.

Mass spectrometry is a sensitive technique used to detect, identify and quantitate molecules based on their mass-to-charge (m/z) ratio. Suitable mass spectrometry for identifying peptides includes tandem mass spectrometry (MS/MS). This may be combined with other techniques such as liquid chromatography (LC) or gas chromatography (GC), e.g. LC-MS/MS.

Any of the peptides, nucleic acid molecules, vectors and/or affinity reagents provided herein may be isolated, recombinant, synthetic and/or mutant. They may incorporate, or be linked to, a moiety, which may be a detectable moiety.

The peptide may incorporate one or more, e.g. at least 1, 2, 3, 4 or 5 amino acids which possess a side chain that is not coded for by the standard genetic code, termed herein "non-coded amino acids". These may be selected from amino acids which are formed through metabolic processes such as ornithine or taurine, and/or artificially modified amino acids such as 9H-fluoren-9-ylmethoxycarbonyl (Fmoc), (tert)-(B)utyl (o)xy (c)arbonyl (Boc), 2,2,5,7,8-pentamethylchroman-6-sulphonyl (Pmc) protected amino acids, or amino acids having the benzyloxy-carbonyl (Z) group.

The peptide may comprise or consist of only amino acids having the L-configuration. Alternatively, it may comprise one or more amino acids having the D configuration, e.g. it may contain at least 1, 2, 3, 4 or 5 D-amino acids.

By "peptidomimetic" is meant a compound which is functionally equivalent or similar to a peptide and which can adopt a three-dimensional structure similar to its peptide counterparts, but which is not solely composed of amino acids linked by peptide bonds.

For example, the backbone of the peptidomimetic may incorporate one or more nitrogen atoms instead of one or more carbon atoms. A preferred class of peptidomimetics are peptoids, i.e. N-substituted glycines. Peptoids are closely related to their natural peptide counterparts, but they differ chemically in that their side chains are appended to nitrogen atoms along the molecule's backbone, rather than to the α-carbons as they are in amino acids.

The peptidomimetic may incorporate one or more di-amino acids and/or β-amino acids.

By "affinity reagent" is meant an agent that can specifically bind to a target. In the present context, the target is a peptide or protein, more particularly a specific peptide, preferably selected from the peptides or proteins disclosed in any one of Tables 5-13, 14-17, 2 or 3, preferably Tables 5-9, more preferably Tables 10-13 or 14-17, or variants thereof as defined herein. Thus, the affinity reagent is an agent that can specifically bind to a specific target peptide (or protein). By that is meant that the affinity reagent will be specific for a target peptide (or protein) having a particular amino acid sequence, so the affinity reagent will bind to this peptide (or protein), but will not bind to, or not significantly bind to, a non-target peptide (or protein) having a different amino acid sequence. For example, an affinity reagent specific for the peptide (or protein) having the sequence APLLFGG will not bind to, or not significantly bind to, a peptide (or protein) having the sequence YFPAA.

The term "does not significantly bind to" a non-target peptide (or protein) should be understood such that any binding of the affinity reagent to a non-target peptide (or protein) does not prohibit the use of said affinity reagent for the purpose of detecting a target peptide (or protein) in a method provided herein. Thus, by "insignificant" binding to a non-target peptide (or protein) is meant that the binding of the affinity reagent to non-target peptides (or proteins) is weaker than its binding to the target peptide (or protein). Some minor cross-reaction with non-target peptides (or proteins) may thus occur, but this level of binding can be considered to be "background" binding.

The affinity reagent may, for example, be selected from an antibody, a nucleic acid aptamer, and an affinity protein scaffold. In some embodiments, peptides, e.g. a set of peptides, as described herein can be used as affinity reagents, e.g. to detect antibodies in appropriate samples.

The term "antibody" extends to all antibodies and antigen binding fragments thereof, including whole antibodies, dimeric, trimeric and multimeric antibodies; bispecific antibodies; chimeric antibodies; recombinant and engineered antibodies, and fragments thereof.

The term "antibody" is thus used to refer to any antibody-like molecule that has an antigen binding region, and this term includes antibody fragments that comprise an antigen binding domain such as Fab', Fab, F(ab')2, single domain antibodies (DABs), Fv, scFv (single chain Fv), dsFv, ds-scFv, Fd, minibodies, diabodies, triabodys (scFv-Fab fusions); sc-diabodys; Bispecific T-cell Engager (BITE) (scFv-scFv tandems to attract T cells); dual variable domain (DVD)-Ig; small immunoprotein (SIP); DART (ds-stabilized diabody "Dual Affinity ReTargeting").

The techniques for preparing and using various antibody-based constructs and fragments are well known in the art (see Kabat et al., 1991, specifically incorporated herein by reference).

The term "aptamer" extends to any single-stranded oligonucleotides that are capable of binding a target molecule with specificity. The aptamer may comprise or consist of DNA and/or RNA. It may comprise or consist of 10-100 nucleotides, preferably 20 to 60 nucleotides, more preferably about 40 nucleotides. Thus, it may preferably comprise or consist of at least 10, 20, 30, or 40 nucleotides and no more than 100, 90, 80, 70, 60, or 50 nucleotides.

The techniques for preparing and using various aptamers are well known in the art. For example, a method for aptamer engineering known as SELEX (systematic evolution of ligands by exponential enrichment) is widely used (see Tuerk and Gold, Systematic evolution of ligands by exponential enrichment: RNA ligands to bacteriophage T4 DNA polymerase Science 1990; 249(4968):505-10 specifically incorporated herein by reference).

The term "affinity protein scaffold" extends to any affinity reagents based on an affinity moiety linked to a non-antibody protein scaffold. The "affinity moiety" is a moiety that is capable of binding a target molecule with specificity. The affinity moiety may, for example, comprise or consist of an oligopeptide or an oligonucleotide. For example, the affinity moiety may comprise or consist of an aptamer. The affinity moiety may comprise or consist of 3-100 amino acids, preferably 5 to 40 amino acids, more preferably about 10-20 amino acids. Thus, it may preferably comprise or consist of at least 5, 6, 7, 8, 9 or 10 and no more than 40, 30, 20, 18, 15 or 12 amino acids.

The affinity reagent is preferably an antibody or an aptamer. The affinity reagent may incorporate, or be linked to, a detectable moiety.

A "detectable moiety" is a label such as, e.g., an enzymatic or radioactive label. Suitable examples include biotin; fluorescein isothiocyanate, rhodamine or luciferin; or an enzyme such as alkaline phosphatase, beta-galactosidase or horseradish peroxidase.

The "nucleic acid molecule" may be a DNA or an RNA molecule. It may have any length, e.g. comprising or consisting of at least 9 nucleotides and preferably no more than 1000 nucleotides. The nucleic acid molecule may be a probe, in which case it preferably comprises no more than 100, 90, 80, 70, 60, 50, 40 or 30 nucleotides. Preferably, it comprises or consists of about 9-50, 9-40, 9-35, 9-30 or 9-21 nucleotides, e.g. about 9, 10, 11, 12, 13, 14, 15, 16, 17, 18, 19, 20, 21, 22, 23, 24, 25, 26, 27, 28, 29 or 30 nucleotides. The nucleic acid molecule may incorporate, or be linked to, a detectable moiety.

The nucleic acid molecule may be immobilized on a solid support. In the case of a set of nucleic acid molecules, the nucleic acid molecules may be immobilized on one or more solid supports. The solid support may e.g. be a sheet, filter, membrane, plate, chip or biochip. Indeed, any of the affinity reagents as described herein (or the peptides or sets of peptides as described herein), may similarly be immobilized on one or more solid supports.

The "sample" may be any sample that may contain microbes/bacteria and/or microbial/bacterial biomarkers. It may contain live microbes/bacteria and/or dead microbes/bacteria, e.g. microbes/bacteria that have been lysed, and/or microbial/bacterial biomarkers that have been released by microbes/bacteria into their environment.

The sample may thus contain microbes/bacteria and/or microbial/bacterial biomarkers, or be suspected of containing microbes/bacteria and/or microbial/bacterial biomarkers.

The sample may be, or comprise, a microbial/bacterial culture, which may, e.g., be a colony or a liquid culture. However, in some embodiments the sample is not a microbial/bacterial culture. Advantageously, the methods provided herein do not require a step of culturing microbes/bacteria prior to the detection step. Therefore, the method does preferably not include a microbial/bacterial culture step. Preferably, the method is carried out on a sample that has not been cultured. By "cultured" or "culture step" is meant incubating the sample under conditions to encourage the growth of microbes/bacteria, e.g. incubating in the presence of suitable nutrients at a suitable temperature, pH and the like for a suitable period of time, e.g. at least a few hours or a few days.

The sample may e.g. be an environmental specimen, a food, or a beverage.

It may be an ex vivo or in vitro sample, e.g., a specimen, which may be a clinical specimen. The specimen may optionally be a provided specimen, i.e. a specimen that was previously obtained or removed from a subject. Optionally, the method may include a step of obtaining a specimen from a subject.

A (clinical) sample that has been spiked with microbes/bacteria, i.e. to which microbes/bacteria have been deliberately added, is referred to herein as a "spiked (clinical) sample". Typically, a spiked sample will have been spiked with a single known type of microbe/bacterium ("single spiked sample"), although spiked samples spiked with two or more types of known microbes/bacteria ("multiple spiked sample") may alternatively be used. In some embodiments, a spiked sample may additionally have been spiked with one or more unidentified types of microbes/bacteria.

Any reference to a (clinical) sample that does not include the term "spiked" should be understood to refer to a non-spiked sample, i.e. a sample which has not deliberately been altered to contain added microbes/bacteria.

The terms "subject" and "patient" are used interchangeably herein unless specified otherwise. The "subject" may be a human or a non-human animal, preferably a mammal, for example any livestock, domestic or laboratory animal. Specific examples include mice, rats, pigs, cats, dogs, sheep, rabbits, cows and monkey. Preferably, however, the subject is a human.

The subject may, e.g., be a subject having a microbial/bacterial infection, a subject suspected of having a microbial/bacterial infection, a subject diagnosed as having an infection of unknown cause, or a subject suspected of having an infection of unknown cause. By "unknown cause" is meant in this context that it is unknown whether the infection is caused by bacteria, viruses, a combination of bacteria and viruses, or caused by a different causal agent. Samples obtained from such subjects, or any other subjects as described herein are preferred samples for analysis in accordance with the present invention.

The specimen may optionally be selected, for example, from a tissue specimen, and/or body fluid specimen. For example, it may be a surgical resection specimen, a biopsy specimen, a swab, a lavage, and/or a smear.

A body fluid may, for example, be selected from blood, plasma, serum, sputum, lavage fluid, pus, urine, saliva, phlegm, vomit, faeces, amniotic fluid, cerebrospinal fluid, pleural fluid, semen, vaginal secretion, interstitial fluid, and/or lymph. The blood may be a peripheral blood sample.

The specimen is preferably derived from the respiratory tract. It may be derived from the upper respiratory tract, e.g. the nose, mouth, sinuses, and/or throat; and/or from the lower respiratory tract, e.g. the trachea, bronchial tubes, and/or the lungs. It may, for example, be a nasopharyngeal swab, a nasopharyngeal wash, a bronchoalveolar lavage or an endotracheal aspirate.

The sample may be processed prior to the biomarker detection step. Thus, the method may include a sample processing step, and/or it may be carried out on a previously processed sample. The sample processing may include one or more wash steps, microbial/bacterial enrichment steps, lysis steps, proteolysis steps, and/or purification steps.

By "microbial/bacterial enrichment" is meant a step to enrich the proportion of microbes/bacteria in the sample. This may involve the removal of some or all non-microbial biomass, such as animal biomass. This may involve the selective lysis of animal cells and optionally the degradation of DNA. For example, the MolYsis™ kit may be used.

By "lysis" is meant that the microbes/bacteria are lysed, i.e. their cell membranes are disrupted such that the cellular content, including proteins and peptides, is released from the microbial/bacterial cell. The lysis step may be physical, e.g., be carried out using bead beating; and/or it may be reagent based, e.g. using a denaturing or non-denaturing detergent such as Sodium deoxycholate, SDS, Triton X-100 or CHAPS.

By "proteolysis" is meant the (hydrolytic) breakdown of proteins/polypeptides into polypeptides, oligopeptides and/or free amino acids. A proteolysis step may include contacting a sample with a suitable protease. By "protease" is meant an enzyme which catalyses hydrolytic proteolysis. The protease may be selected from endoproteases and exoproteases, endoproteases being preferred. Suitable endoproteases include Serine proteases, Threonine proteases, Cysteine proteases, Aspartate proteases, Metalloproteases and Glutamic acid proteases. Examples of suitable serine endoproteases include pepsin, trypsin, chymotrypsin and elastase. Thus, it can be seen that peptides or sets of peptides of or for use in the present invention may not be or may not correspond to naturally occurring peptides, for example are not or do not correspond to peptides which are found in the form of that peptide in an appropriate subject, even though the peptides may be present in larger native proteins found in the subject (e.g. the peptides are fragments of such proteins).

A purification step is any step that removes unwanted material, which may, e.g. be cellular debris such as membrane fractions, nucleic acid and the like; chemical agents; salts and the like. Purification steps may involve a centrifugation step to generate a pellet and a supernatant. The unwanted material, which may be in the pellet or in the supernatant depending on the nature of the purification step, may easily be discarded. A purification step may conveniently be carried out using appropriate commercially available columns. For example, peptides may be desalted using Pep Clean C18 spin columns.

Digestion of microbial/bacterial lysates and generation of peptides may, e.g., be performed using the Lipid-based Protein Immobilization (LPI) methodology, as discussed in the Examples.

The diagnosis may be the diagnosis of a microbial/bacterial infection of any part of the respiratory tract. The diagnosis may be carried out on a subject who has not previously been diagnosed as having an infection; on a subject who has previously been diagnosed as having an infection, wherein a diagnosis as to whether the infection is microbial/bacterial has not yet been made; or on a subject who has previously been diagnosed as having a microbial/bacterial infection, wherein the identity of the microbial/bacterial species causing the infection has not yet been determined.

The therapy is preferably the treatment a microbial/bacterial infection, which may be the vaccination against a current and/or future microbial/bacterial infection.

The infection may be selected from otitis (ear infection), meningitis (infection of the lining of the brain and/or spinal cord), bacteremia (blood stream infection), an infection of any part of the respiratory tract, Epiglotittis (swelling of the windpipe that can cause breathing trouble), Cellulitis (skin infection) and/or Infectious arthritis (inflammation of the joint). If it is otitis, it may be otitis externa, otitis media or otitis interna (labyrinthitis).

The infection may preferably be an infection of any part of the respiratory tract, e.g. tonsillitis, sinusitis, laryngitis, bronchitis, and/or pneumonia. It may be an acute respiratory infection.

As used herein, the term "acute respiratory infection" or "ARI" refers to an infection, or an illness showing symptoms and/or physical findings consistent with an infection (e.g., symptoms such as coughing, wheezing, fever, sore throat, and/or congestion; physical findings such as elevated heart rate, elevated breath rate, abnormal white blood cell count, and/or low arterial carbon dioxide tension ($PaCO_2$), etc.), of the upper or lower respiratory tract, often due to a microbial/bacterial or viral pathogen, and/or characterized by rapid progression of symptoms over hours to days. ARIs may primarily be of the upper respiratory tract (URIs), the lower respiratory tract (LRIs), or a combination of the two. ARIs may have systemic effects due to spread of the infection beyond the respiratory tract or due to collateral damage induced by the immune response. An example of the former includes *Staphylococcus aureus* pneumonia that has spread to the blood stream and can result in secondary sites of infection, including endocarditis (infection of the heart valves), septic arthritis (joint infection), or osteomyelitis (bone infection). An example of the latter includes *influenza* pneumonia leading to acute respiratory distress syndrome and respiratory failure.

The microbial/bacterial infection is preferably caused by a microbe/bacterium selected from *Streptococcus pneumoniae, Staphylococcus aureus, Haemophilus influenzae, Escherichia coli,* and/or *Moraxella catarrhalis*.

As used herein, the terms "treatment," "treat," and "treating" refer to reversing, alleviating, inhibiting the progress of a disease or disorder as described herein; or delaying, eliminating or reducing the incidence or onset of a disorder or disease as described herein, as compared to that which would occur in the absence of the measure taken. Thus, the treatment may be prophylactic.

The terms "prophylaxis" or "prophylactic use" and "prophylactic treatment" as used herein, refer to any medical or public health procedure whose purpose is to prevent the disease herein disclosed. As used herein, the terms "prevent", "prevention" and "preventing" refer to the reduction in the risk of acquiring or developing a given condition, or the reduction or inhibition of the recurrence or said condition in a subject who is not ill. An example of a prophylactic treatment is vaccination against a disease.

Any of the methods of detecting or identifying or diagnosing as described herein may thus optionally further comprise a therapeutic step, for example if a positive detection, identification, or diagnosis is reached. Appropriate therapies for the various bacterial infections described herein would be well known to a person skilled in the art, and any of these could be used. Preferably however a therapeutic step using an antibiotic or other antibacterial or antimicrobial treatment for the particular bacteria concerned could be carried out. Alternatively a treatment involving vaccination against the bacteria which has been detected and/or a future microbial/bacterial infection can be carried out. Thus, methods of treatment of microbial/bacterial infection in a subject, comprising the methods of detecting or identifying or diagnosing as described herein, are also provided. Such methods of treatment may comprise obtaining or receiving results of the level or presence of one or more of the bacterial biomarkers, or bacteria, in a subject (e.g. a sample from a subject) as described herein, and administering a treatment for example as described above, for example when the level or presence of said biomarkers is indicative of disease or infection, e.g. is above an appropriate control or reference level.

A "subject in need" of the methods of the invention can be a subject known to have, or suspected of having, a microbial/bacterial infection, such as a respiratory tract infection. The subject may be a subject who has an increased susceptibility to microbial/bacterial infections, but who does not yet have symptoms of microbial/bacterial infection. The term "increased susceptibility" in this context refers to a subject that has a likelihood of suffering from said disease that is at least 10% higher than that for the average population.

By "biomarker" is meant an objective, quantifiable characteristic of a specific type of microbe/bacterium. The biomarker may be a single peptide, or a plurality of peptides.

A pharmaceutical composition as provided herein may further comprise a pharmaceutically acceptable excipient. The excipient may include any excipients known in the art, for example any carrier or diluent or any other ingredient or agent such as buffer, antioxidant, chelator, binder, coating, disintegrant, filler, flavour, colour, glidant, lubricant, preservative, sorbent and/or sweetener.

All patents, patent applications and publications referred to herein are incorporated by reference in their entirety. In the event of conflicting terminology, the present specification is controlling. Further, the embodiments described in one aspect of the present invention are not limited to the aspect described. The embodiments may also be applied to a different aspect of the invention as long as the embodiments do not prevent these aspects of the invention from operating for their intended purpose.

It should be appreciated that the invention may be embodied in different forms and should not be construed as limited to the embodiments set forth herein. Rather, these embodiments are provided so that this disclosure will be thorough and complete, and will fully convey the scope of the invention to those skilled in the art. The terminology used in the description of the invention herein is for the purpose of describing particular embodiments only and is not intended to be limiting of the invention.

FIGURES

The following drawings are provided to illustrate various aspects of the present inventive concept and are not intended to limit the scope of the present invention unless specified herein.

FIG. 1. Exemplary workflow for generating peptide biomarker database identified by MS, followed by ranking by number of hits to generate a preliminary inclusion list, i.e. a first set of peptide biomarkers.

Figure 2:
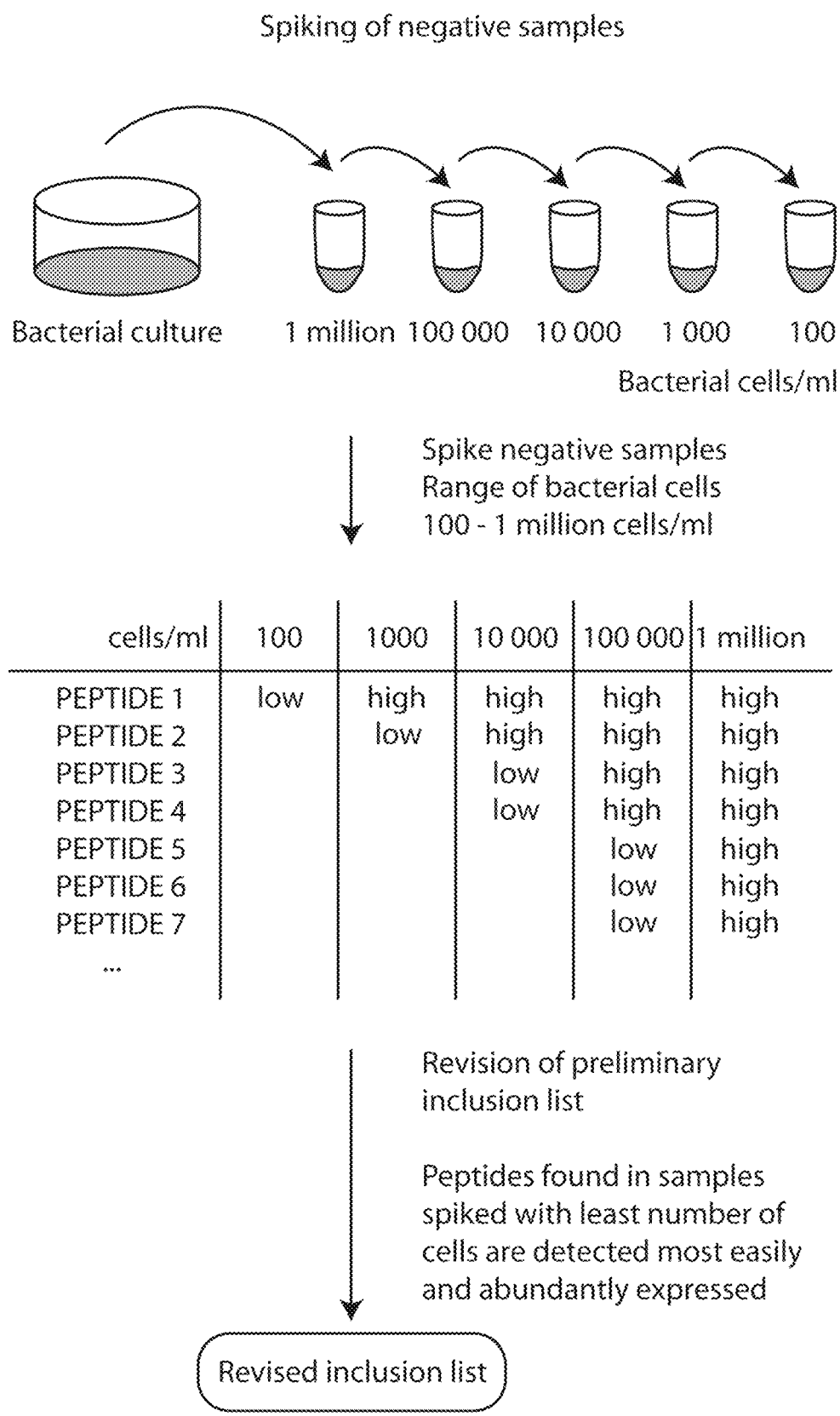

FIG. 2. Exemplary workflow for experimentally verifying and revising an inclusion list (set of peptide biomarkers) involving spiking of negative samples and ranking of peptides according to sensitivity of detection.

Figure 3:
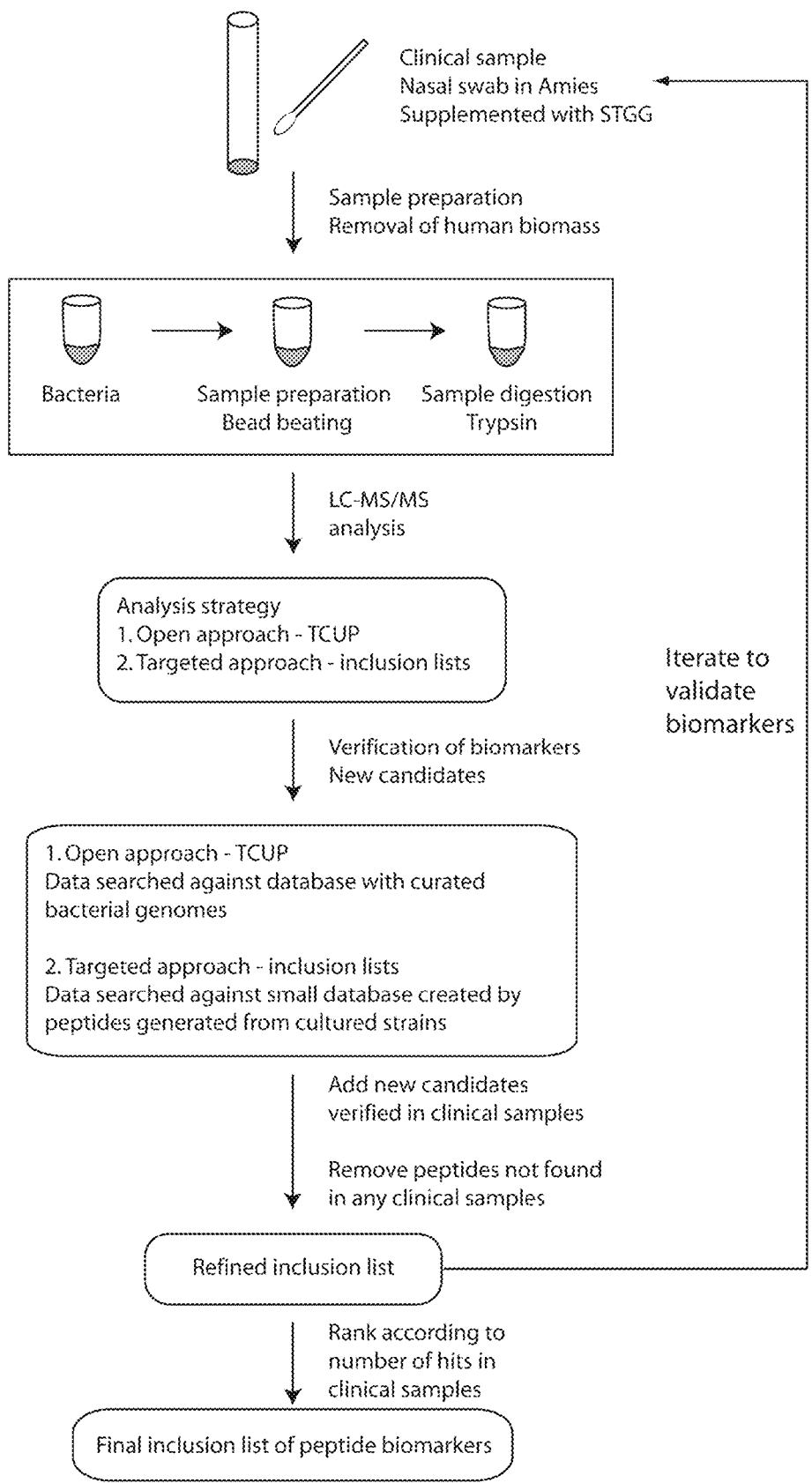

FIG. 3. Exemplary workflow for experimentally verifying and revising an inclusion list. The workflow includes analysing clinical samples, exemplified by nasal swabs, followed by bioinformatics processing using a targeted approach ("inclusion list only" mode or "inclusion list plus pick others" mode) and optionally also an open (TCUP) approach, followed by and revision of the inclusion list. The revision of the inclusion list may include verifying any peptide biomarkers of the inclusion list on the basis of their detection in the clinical sample; removing any peptide biomarkers on the basis of their non-detection in the clinical sample; and/or the addition of new biomarkers on the basis of their detection in the clinical sample.

Figure 4:
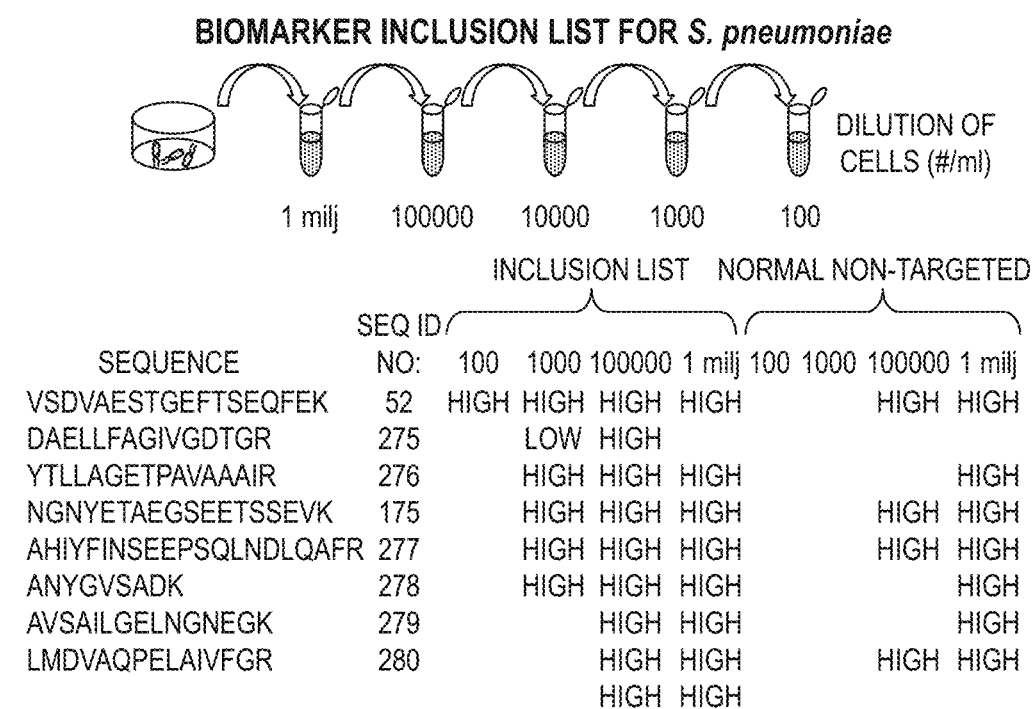

FIG. 4. Comparison of dilution series for detecting certain peptide species using targeted (here: "inclusion list plus pick others" mode) and normal MS analysis approach.

Figure 5:
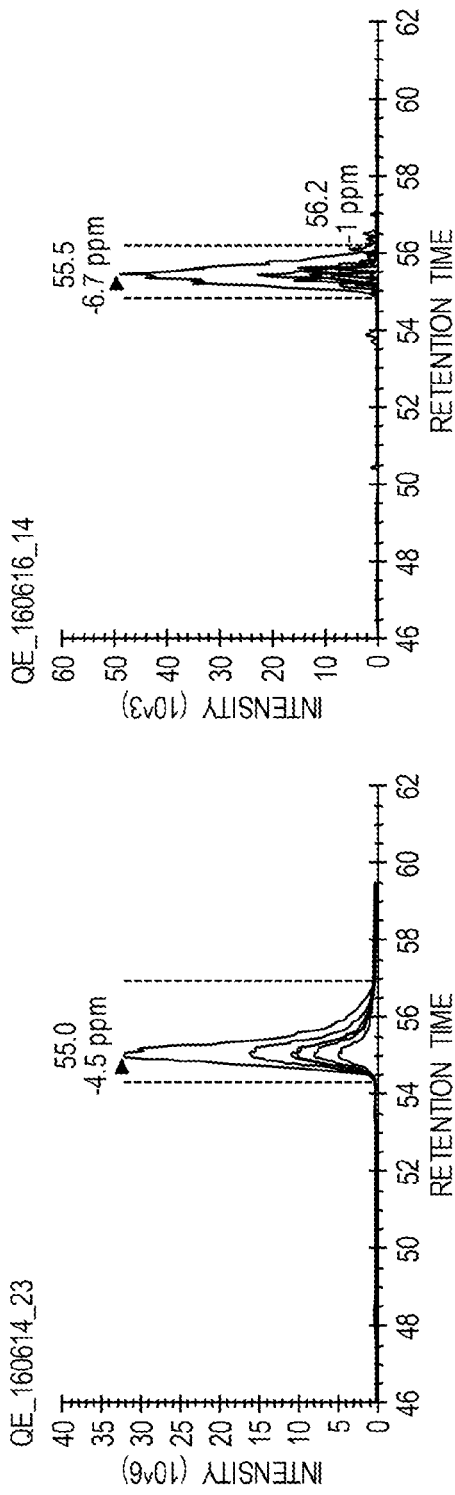

FIG. 5. Identification of species unique peptides in clinical samples using parallel reaction monitoring (PRM) methods and comparison to results from cultures.

Figure 6:
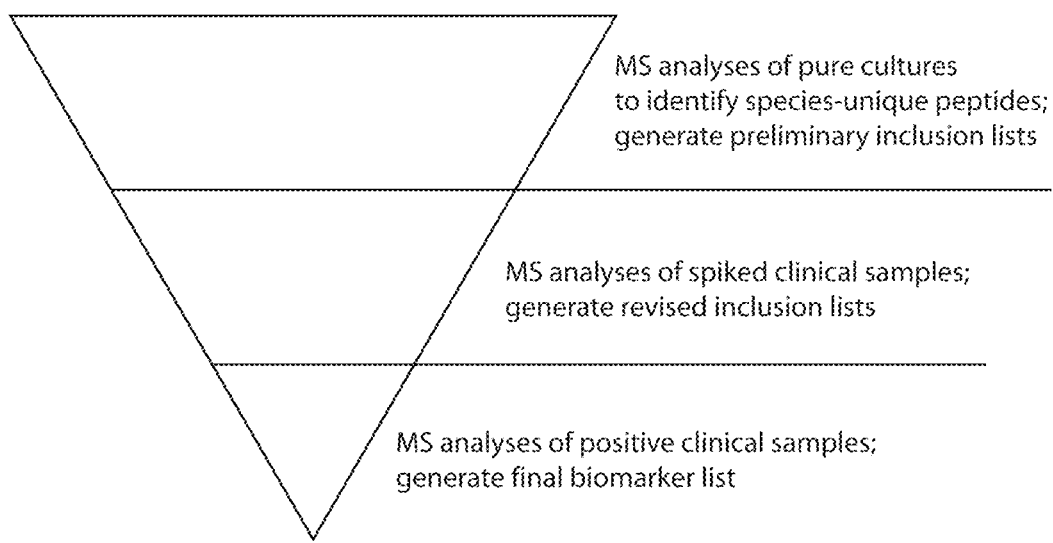

FIG. 6. Exemplary workflow of generating an inclusion list (set of peptide biomarkers) using spiked negative samples for a first revision of the preliminary inclusion list and clinical samples to for a further revision of the (revised) inclusion list. In the first step thousands of peptides (+15000 peptides) in cultures from the different microbes/bacteria (Sp, Hi, Mc, Sa) are identified. In the second step negative clinical samples are spiked with the respective microbes/bacteria in order to mimic clinical samples, thus reducing the list of peptides to hundreds instead of thousands of candidate peptide biomarkers. Finally validation of the peptides is performed by analysing real positive clinical samples thus resulting in a final inclusion list of peptide biomarkers.

FIG. 7. Direct analyses of clinical respiratory tract samples using PRM, targeting the most promising peptides. The peptide peaks are labeled with numbers corresponding their sequences from Table 10 (*Staphylococcus aureus*), Table 11 (*Moraxella catarrhalis*), Table 12 (*Haemophilus influenzae*) and Table 13 (*Streptococcus pneumonia*).

TABLES

TABLE 1

Bacterial strains selected from the Culture Collection University of Gothenburg (CCUG). The strains were selected by to represent the genetic diversity within each species.

| *Haemophilus influenzae* | *Moraxella catarrhalis* | *Streptococcus pneumoniae* | *Staphylococcus aureus* |
|---|---|---|---|
| CCUG 23945T | CCUG 353T | CCUG 28588T | CCUG 41582T |
| CCUG 35273 | CCUG 34455 | CCUG 35272 | CCUG 62707 |
| CCUG 4559 | CCUG 63408 | CCUG 1350 | CCUG 68900 |
| CCUG 60440 | CCUG 18284 | CCUG 11780 | CCUG 62271 |
| CCUG 26214 | CCUG 56314 | CCUG 33774 | CCUG 1964 |
| CCUG 23969 | CCUG 36757 | CCUG 7206 | CCUG 39740 |
| CCUG 33775 | CCUG 41836 | CCUG 35180 | CCUG 49245 |
| CCUG 32226 | CCUG 18283 | | CCUG 64138 |
| CCUG 9188 | CCUG 27321 | | CCUG 1979 |
| | CCUG 33013 | | CCUG 69160 |
| | CCUG 63533 | | CCUG 62274 |
| | | | CCUG 1988 |
| | | | CCUG 1914 |

TABLE 2

Species discriminatory peptide biomarkers found in dilution series (10^4).

| H. influenzae | M. catarrhalis |
|---|---|
| GVAADAISATGYGK<br>SEQ ID NO: 36 | VGDEIEIIGIKPTAK<br>SEQ ID NO: 251 |
| AVVYNNEGTNVELGGR<br>SEQ ID NO: 41 | TDEQLQAELDNK<br>SEQ ID NO: 252 |
| FGQGEAPVVAAPEVVSK<br>SEQ ID NO: 249 | GLITNSIENTNNITK<br>SEQ ID NO: 253 |
| DGQVTGALATLGEPYK<br>SEQ ID NO: 250 | QIVSNAGDEASVIVNEVK<br>SEQ ID NO: 19 |
| LSVIAEQSNSTR<br>SEQ ID NO: 47 | NTIEGENSVAIGSNNTVK<br>SEQ ID NO: 254 |
| YDANNIIAGIAYGR<br>SEQ ID NO: 42 | QQTEAIDALNK<br>SEQ ID NO: 255 |

TABLE 2-continued

Species discriminatory peptide biomarkers found in dilution series (10^4).

| S. pneumoniae | S. aureus (10^3) |
|---|---|
| VQYEGGTEDELIR<br>SEQ ID NO: 256 | ITYTMIGDPSQTITR<br>SEQ ID NO: 262 |
| VSDVAESTGEFTSEQFEK<br>SEQ ID NO: 52 | AILNNENNVLNVSIQLDGQYGGHK<br>SEQ ID NO: 263 |
| GLDVTDEEGDDVTNGIFVGAK<br>SEQ ID NO: 257 | GLEVGQIVESGAEADIK<br>SEQ ID NO: 264 |
| SQTEQGEINIER<br>SEQ ID NO: 258 | TVEVDGYNAIQVGFEDK<br>SEQ ID NO: 265 |
| PAPAPQPAPAPKPEK<br>SEQ ID NO: 259 | SINPADTSQVIANASK<br>SEQ ID NO: 266 |
| AEADKPETEAGKER<br>SEQ ID NO: 260 | GGLTDTFTNAFSSGNNVTQGVSVEVGEK<br>SEQ ID NO: 267 |
| GAANGVVSHENTR<br>SEQ ID NO: 53 | NFDVLDEATGLAQR<br>SEQ ID NO: 268 |
| AEGVATASETAEAASAAKPEEK<br>SEQ ID NO: 261 | |

TABLE 3

Results of Example 2

| Peptide | Present | Putative protein from which peptide is potentially derived |
|---|---|---|
| AEKPADQQAEEDYAR<br>SEQ ID NO: 181 | YES | hypothetical protein |
| AIEAGQTVDFSDLAIK<br>SEQ ID NO: 185 | YES | glycerol facilitator-aquaporin |
| AIENPFAVEVADVETEK<br>SEQ ID NO: 269 | YES | phosphoglucomutase |
| AVVVNPESTGVAIEEK<br>SEQ ID NO: 270 | YES | alcohol dehydrogenase |
| IDTFGTGTVAESQLEK<br>SEQ ID NO: 171 | YES | IS1380-Spn1 transposase |
| ILDLNEEEGRVSLSIK<br>SEQ ID NO: 271 | YES | 30S ribosomal protein S1 |
| LLAGADPDDGTEVIEAK<br>SEQ ID NO: 174 | YES | pneumococcal surface protein A |
| LYQNAEEVINK<br>SEQ ID NO: 272 | YES | NADH oxidase |
| LYQNAEEVINKLSDK<br>SEQ ID NO: 273 | YES | NADH oxidase |
| NLPVGSDGTFTPEDYVGR<br>SEQ ID NO: 61 | YES | methionyl-tRNA synthetase |
| NVEIIEDDKQGVIR<br>SEQ ID NO: 60 | YES | 30S ribosomal protein S8 |
| VSDVAESTGEFTSEQFEK<br>SEQ ID NO: 52 | YES | general stress protein |
| VSDVTTLEEARPATTPSSPNVR<br>SEQ ID NO: 274 | YES | capsular polysaccharide biosynthesis protein Wzd |

TABLE 4

E. coli strains selected from the Culture Collection University of Gothenburg (CCUG). The strains were selected by to represent the genetic diversity within each species.

| | | | | | |
|---|---|---|---|---|---|
| CCUG | 24T | | | Human urine, cystitis | Sweden |
| CCUG | 65156 | A | ECOR4 | Human faeces, healthy woman | USA (Iowa) |
| CCUG | 65157 | B1 | ECOR29 | Kangaroo faeces, healthy | USA (Nevada) |
| CCUG | 65158 | C | ECOR70 | Gorilla faeces, healthy | USA (Washington) |
| CCUG | 65159 | D | ECOR37 | Marmoset faeces, healthy | USA (Washington) |
| CCUG | 65160 | E | ECOR47 | Sheep faeces, healthy | New guinea |
| CCUG | 65161 | F | ECOR39 | Human faeces, healthy woman | Sweden |
| CCUG | 65162 | B2 | ECOR53 | Human faeces, healthy woman | USA (Iowa) |
| CCUG | 65163 | B2 | ECOR56 | Human urine, woman | Sweden |
| ATCC | 35320 | A | ECOR1 | Human, woman | USA (Iowa) |
| ATCC | 35345 | B1 | ECOR26 | Human, infantis | USA (Massachusetts) |
| ATCC | 35359 | D | ECOR40 | Human, woman | Sweden |
| ATCC | 35379 | B2 | ECOR60 | Human, woman | Sweden |

TABLE 5

Moraxella catarrhalis biomarker peptides

| SEQ ID NO | | |
|---|---|---|
| SEQ ID NO: 27 | 1 | SQIYQTTASVSGAR |
| SEQ ID NO: 22 | 2 | VDATVDAQNPTK |
| SEQ ID NO: 28 | 3 | LLNETTGQVVPK |
| SEQ ID NO: 20 | 4 | AIAQVGSISANSDATIGELISK |
| SEQ ID NO: 72 | 5 | AQYDITQNAGTER |
| SEQ ID NO: 21 | 6 | ELSNTAAETQPK |
| SEQ ID NO: 19 | 7 | QIVSNAGDEASVIVNEVK |
| SEQ ID NO: 18 | 8 | VVLAGDTVVSDR |
| SEQ ID NO: 26 | 9 | YVVEGANMPLDAQAIDIVR |
| SEQ ID NO: 31 | 10 | GLPVSNSGAPISVPVGQATLGR |
| SEQ ID NO: 29 | 11 | SSENVVVSVR |
| SEQ ID NO: 25 | 12 | THTSALAEENQQASIPR |
| SEQ ID NO: 24 | 13 | FNATAALGGYGSK |
| SEQ ID NO: 33 | 14 | AVATQQATVSAEYLQK |
| SEQ ID NO: 73 | 15 | TFHVGGAASAASVDNSVSVGNAGSVR |
| SEQ ID NO: 35 | 16 | LGAQEAELVSNSK |
| SEQ ID NO: 23 | 17 | QSDVGQLTGK |
| SEQ ID NO: 32 | 18 | VNYNGDTDTVTLSGVAK |
| SEQ ID NO: 34 | 19 | ADSGLSESEIEEMIR |
| SEQ ID NO: 30 | 20 | AISYGNSADAQPYVGAK |
| SEQ ID NO: 74 | 21 | ANLDTSTEEAR |
| SEQ ID NO: 75 | 22 | ASSENTQNIAK |
| SEQ ID NO: 76 | 23 | DADAVEAGQVIAK |
| SEQ ID NO: 77 | 24 | FAATADAITK |

TABLE 5-continued

Moraxella catarrhalis biomarker peptides

| SEQ ID NO | | |
|---|---|---|
| SEQ ID NO: 78 | 25 | LNTQGASFDYPVASNATEQGR |
| SEQ ID NO: 79 | 26 | NKADADASFETLTK |
| SEQ ID NO: 80 | 27 | AKLESLTEDMVAR |
| SEQ ID NO: 81 | 28 | IITNNHAIALNLAAEGYGIAK |
| SEQ ID NO: 82 | 29 | ILADIAMHDAAAFTAITEK |
| SEQ ID NO: 83 | 30 | IYRPEIYNANSVAGQIYK |
| SEQ ID NO: 84 | 31 | LDITETTDDSR |
| SEQ ID NO: 85 | 32 | ALESNVEEGLLDLSGR |
| SEQ ID NO: 86 | 33 | EFYAAETLPAESR |
| SEQ ID NO: 87 | 34 | MNIEQTLQSAEDTAR |
| SEQ ID NO: 88 | 35 | QDPANQEVYTK |
| SEQ ID NO: 89 | 36 | SVTATDNTTQATVIK |
| SEQ ID NO: 90 | 37 | VGVMAGPEQAVAEVAGQVAK |
| SEQ ID NO: 91 | 38 | AHIGLAQAQFPEGLASSQVDALAR |
| SEQ ID NO: 92 | 39 | ALATDYSHVVAPATTTGK |
| SEQ ID NO: 93 | 40 | ENTVIVDGAGDKASIEAR |
| SEQ ID NO: 94 | 41 | LPVDKETAPSDDATATTQFSR |
| SEQ ID NO: 95 | 42 | LTYTDGSDPGSYYR |
| SEQ ID NO: 96 | 43 | NLGAAVNEVTANEQSAEAKAPEDQQY |
| SEQ ID NO: 97 | 44 | SDALYVVEDSVK |
| SEQ ID NO: 98 | 45 | LADEGDIDVR |
| SEQ ID NO: 99 | 46 | LTQATAQASAPQGR |
| SEQ ID NO: 100 | 47 | LYPNDPTYQAASEK |

TABLE 5-continued

Moraxella catarrhalis biomarker peptides

| SEQ ID NO | | |
|---|---|---|
| SEQ ID NO: 101 | 48 | NQADIANNINNIYELAQQQDQHSSDIK |
| SEQ ID NO: 102 | 49 | SEVLDGMNSAYNPVVEDK |
| SEQ ID NO: 103 | 50 | SLENDLGVSLLHR |

TABLE 6

Haemophilus influenza biomarker peptides

| SEQ ID NO | | |
|---|---|---|
| SEQ ID NO: 36 | 1 | GVAADAISATGYGK |
| SEQ ID NO: 41 | 2 | AVVYNNEGTNVELGGR |
| SEQ ID NO: 37 | 5 | ANLKPQAQATLDSIYGEMSQVK |
| SEQ ID NO: 42 | 6 | YDANNIIAGIAYGR |
| SEQ ID NO: 38 | 7 | ADSVANYFVAK |
| SEQ ID NO: 48 | 8 | SADLTNEVAVGDVVEAK |
| SEQ ID NO: 104 | 9 | FGGNAQQTAQLPR |
| SEQ ID NO: 39 | 10 | GSYEVLDGLDVYGK |
| SEQ ID NO: 40 | 11 | LSQERADSVANYFVAK |
| SEQ ID NO: 51 | 12 | AQYIVEQVIGQAR |
| SEQ ID NO: 43 | 13 | ATHNFGDGFYAQGYLETR |
| SEQ ID NO: 105 | 14 | GLSVGDQIQAGINSPIK |
| SEQ ID NO: 45 | 15 | QQVNGALSTLGYR |
| SEQ ID NO: 50 | 16 | TSPTQNLSLDAFVAR |
| SEQ ID NO: 44 | 17 | AVVYNNEGTKVELGGR |
| SEQ ID NO: 47 | 18 | LSVIAEQSNSTR |
| SEQ ID NO: 49 | 19 | SADLTSEVAVGDVVEAK |
| SEQ ID NO: 46 | 20 | YVPTNGNTVGYTFK |
| SEQ ID NO: 106 | 21 | ATGEINLDGENLLTTK |
| SEQ ID NO: 107 | 22 | ATHNLGDGFYAQGYLETR |
| SEQ ID NO: 108 | 23 | GIASGTEVSFGTYGLK |

TABLE 6-continued

Haemophilus influenza biomarker peptides

| SEQ ID NO | | |
|---|---|---|
| SEQ ID NO: 109 | 24 | GVAAIVTLSSTGR |
| SEQ ID NO: 110 | 25 | NNEGTNVELGGR |
| SEQ ID NO: 111 | 26 | TISDGITSAEDKEYGVLK |
| SEQ ID NO: 112 | 27 | AILPPQEIEQGTVK |
| SEQ ID NO: 113 | 28 | ATNLSAEQLNVTDASEK |
| SEQ ID NO: 114 | 29 | FKQTAPSNNEVENELTNEQLTK |
| SEQ ID NO: 115 | 30 | GIDGLVLGANYLLAQER |
| SEQ ID NO: 116 | 31 | IAEQSNSTIKDQK |
| SEQ ID NO: 117 | 32 | TAQFSTGGVYIDSR |
| SEQ ID NO: 118 | 33 | YAYVTLGNNTFGEVK |
| SEQ ID NO: 119 | 34 | ANLKPQAQATLDSVYGEISQVK |
| SEQ ID NO: 120 | 35 | AQQLSTDVKNK |
| SEQ ID NO: 121 | 36 | EITEDPAIYPSADILK |
| SEQ ID NO: 122 | 37 | GLKVENTNNPIQVPVGTK |
| SEQ ID NO: 123 | 38 | GVITVSAVGDQINPTLAR |
| SEQ ID NO: 124 | 39 | INATEGAATLTAESGK |
| SEQ ID NO: 125 | 40 | LSVIAEQSNSTADDQK |
| SEQ ID NO: 126 | 41 | LSVIAEQSNTTVDDQK |
| SEQ ID NO: 127 | 42 | LVSAQSGTESDNFGHIITK |
| SEQ ID NO: 128 | 43 | NEGTNVELGGR |
| SEQ ID NO: 129 | 44 | RAELEATAAANLAAAQAR |
| SEQ ID NO: 130 | 45 | SADLTSEVAVGDVVDAK |
| SEQ ID NO: 131 | 46 | SIIAEQSNSTIKDQK |
| SEQ ID NO: 132 | 47 | SVDLTSEVAVGDVVEAK |
| SEQ ID NO: 133 | 48 | TIADGITSAEDKEYGVLNNSK |
| SEQ ID NO: 134 | 49 | TIIGANLSQLTQNELSAGK |
| SEQ ID NO: 135 | 50 | TQTSTSIGFNAK |

TABLE 7

Staphylococcus aureus biomarker peptides

| SEQ ID NO | | |
|---|---|---|
| SEQ ID NO: 2 | 1 | QAGVGAAVVAELSER |
| SEQ ID NO: 3 | 2 | ELINNIQSGQR |
| SEQ ID NO: 1 | 3 | TVQPIDVDTIVASVEK |
| SEQ ID NO: 4 | 4 | LGISDGDVEETEDAPK |
| SEQ ID NO: 5 | 5 | ALLNNMVQGVSQGYVK |
| SEQ ID NO: 8 | 6 | ILAESPNLAISSSSR |

TABLE 7-continued

*Staphylococcus aureus* biomarker peptides

| SEQ ID NO | | |
|---|---|---|
| SEQ ID NO: 136 | 7 | NALIIEDTGDNNVVK |
| SEQ ID NO: 6 | 8 | SNVNDATDYSSETPEGK |
| SEQ ID NO: 10 | 9 | ATEATNATNNQSTQVSQATSQPINFQVQK |
| SEQ ID NO: 15 | 10 | AEENGLTVVDAFNFEAPK |
| SEQ ID NO: 16 | 11 | EKANELLKDNAELIASFSR |
| SEQ ID NO: 11 | 12 | IHLVGDEIANGQGIGR |
| SEQ ID NO: 7 | 13 | ANNVATDANHSYTSR |
| SEQ ID NO: 248 | 14 | AQENGLTVVDAFNFEAPK |
| SEQ ID NO: 137 | 15 | DLSFGENYGVVMEELR |
| SEQ ID NO: 17 | 16 | LLGINATIVMPETAPQAK |
| SEQ ID NO: 12 | 17 | NISNNVLVTIDAAQGK |
| SEQ ID NO: 9 | 18 | NVVEIPLNDEEQSK |
| SEQ ID NO: 14 | 19 | SQGVSEEELNESIDR |
| SEQ ID NO: 13 | 20 | TAKPVAEVESQTEVTE |
| SEQ ID NO: 138 | 21 | TPTEQTKPVQPK |
| SEQ ID NO: 139 | 22 | VMGVDYVSNITEAR |
| SEQ ID NO: 140 | 23 | YLGDEEISVSELK |
| SEQ ID NO: 141 | 24 | AEAQANQMVGDAVEK |
| SEQ ID NO: 142 | 25 | ANELLKDNAELIASFSR |
| SEQ ID NO: 143 | 26 | ATDAENVEKEEAITK |
| SEQ ID NO: 144 | 27 | AVAGAAGGADAAAEK |
| SEQ ID NO: 145 | 28 | ELINGVFTDINPYIK |
| SEQ ID NO: 146 | 29 | HIGTPGEVLEPGQQVNVK |
| SEQ ID NO: 147 | 30 | KAQSEQDQAFLSK |
| SEQ ID NO: 148 | 31 | MIAVLIPDDGSGK |
| SEQ ID NO: 149 | 32 | NAGIGSGFSNDMYEKEGAK |
| SEQ ID NO: 150 | 33 | QNLPVLDVPEDVVEEGVR |
| SEQ ID NO: 151 | 34 | VVITAQTINEETEPELYDAEGNLINNSK |
| SEQ ID NO: 152 | 35 | ADSGTVIQAISK |
| SEQ ID NO: 153 | 36 | ATIDGLQNLKNAEDVAK |
| SEQ ID NO: 154 | 37 | DSDIATTATKVELATK |
| SEQ ID NO: 155 | 38 | FIAETYLDDVEQFNTVR |
| SEQ ID NO: 156 | 39 | FIEETPELFDIQPSLDR |
| SEQ ID NO: 157 | 40 | GLWNENKENEVIER |
| SEQ ID NO: 158 | 41 | IFSEVEPNPSTNTVYK |
| SEQ ID NO: 159 | 42 | LAEQKATDAENVEKEEA |
| SEQ ID NO: 160 | 43 | LAVNEMLNAIQNK |
| SEQ ID NO: 161 | 44 | LNDVEQTNTPGSLNPK |

TABLE 7-continued

Staphylococcus aureus biomarker peptides

| SEQ ID NO | | |
|---|---|---|
| SEQ ID NO: 162 | 45 | MQEVGVTAISGETIIK |
| SEQ ID NO: 163 | 46 | NLSEQGINEATR |
| SEQ ID NO: 164 | 47 | NMLPEVKPSSEVYGK |
| SEQ ID NO: 165 | 48 | NVKDNAIVLEAISGADVNDSTSAPVDDVDFTSDIGKDIK |
| SEQ ID NO: 166 | 49 | QNLPVLDVPEDVVEEGVRK |
| SEQ ID NO: 167 | 50 | SGADVNDSTSAPVDDVDFTSDIGKDIK |

TABLE 8

Streptococcus pneumonia biomarker peptides

| SEQ ID NO | | |
|---|---|---|
| SEQ ID NO: 52 | 1 | VSDVAESTGEFTSEQFEK |
| SEQ ID NO: 53 | 2 | GAANGVVSHENTR |
| SEQ ID NO: 54 | 3 | EEAPVASQSK |
| SEQ ID NO: 60 | 4 | NVEIIEDDKQGVIR |
| SEQ ID NO: 55 | 5 | SADQQAEEDYAR |
| SEQ ID NO: 61 | 6 | NLPVGSDGTFTPEDYVGR |
| SEQ ID NO: 65 | 7 | AVAAADAADAGAAK |
| SEQ ID NO: 63 | 8 | DIGLANDGSIVGINYAK |
| SEQ ID NO: 67 | 9 | TLSPEEYAVTQENQTER |
| SEQ ID NO: 56 | 10 | APLQSELDTK |
| SEQ ID NO: 66 | 11 | GQDWVIAAEVVTKPEVK |
| SEQ ID NO: 62 | 12 | TLELEIAESDVK |
| SEQ ID NO: 64 | 13 | IAELEYEVQR |
| SEQ ID NO: 70 | 14 | IGVISVVEDGDEALAK |
| SEQ ID NO: 68 | 15 | KDEAEAAFATIR |
| SEQ ID NO: 57 | 16 | LKEIDESDSEDYVK |
| SEQ ID NO: 69 | 17 | SQPSSETELSGNKQEQER |
| SEQ ID NO: 71 | 18 | VAYFNEIDTYSEVK |
| SEQ ID NO: 58 | 19 | AKLEEAEKKATEAK |
| SEQ ID NO: 59 | 20 | AVNEPEKPAEESENPAPAPK |
| SEQ ID NO: 168 | 21 | DVPENLITAVVQSNK |
| SEQ ID NO: 169 | 22 | EAEANFNTEQAK |
| SEQ ID NO: 170 | 23 | EIDESDSEDYLKEGLR |
| SEQ ID NO: 171 | 24 | IDTFGTGTVAESQLEK |
| SEQ ID NO: 172 | 25 | LKEIDESDSEDYVKEGFR |
| SEQ ID NO: 173 | 26 | LKEIDESDSEDYVKEGLR |
| SEQ ID NO: 174 | 27 | LLAGADPDDGTEVIEAK |
| SEQ ID NO: 175 | 28 | NGNYETAEGSEETSSEVK |
| SEQ ID NO: 176 | 29 | NTLLELGLDESQIK |
| SEQ ID NO: 177 | 30 | VAAGDLLVTADLNAIR |
| SEQ ID NO: 178 | 31 | VIPKETELATTK |
| SEQ ID NO: 179 | 32 | VVPEAEQLAETK |
| SEQ ID NO: 180 | 33 | AEKDYDAAMKNAEDAK |
| SEQ ID NO: 181 | 34 | AEKPADQQAEEDYAR |
| SEQ ID NO: 182 | 35 | AESTGEFTSEQFEK |
| SEQ ID NO: 183 | 36 | AGITYSEGLVFESK |
| SEQ ID NO: 184 | 37 | AGVVVVDNTSYFR |
| SEQ ID NO: 185 | 38 | AIEAGQTVDFSDLAIK |
| SEQ ID NO: 186 | 39 | ALTPEEVQKR |
| SEQ ID NO: 187 | 40 | AQNTESTVVQLNNGDVK |
| SEQ ID NO: 188 | 41 | DAEHAEEVAPQVK |
| SEQ ID NO: 189 | 42 | DIILAQTEENLTR |
| SEQ ID NO: 190 | 43 | DLENVETVIEKEDVETNASNGQR |
| SEQ ID NO: 191 | 44 | EAGDQATYFDEIR |
| SEQ ID NO: 192 | 45 | EGFVKNVEIIEDDKQGVIR |
| SEQ ID NO: 193 | 46 | ELATQIYQVAR |
| SEQ ID NO: 194 | 47 | GSDGKQFYNNYNDAPLK |
| SEQ ID NO: 195 | 48 | GSIESMHNLPVNLAGAR |
| SEQ ID NO: 196 | 49 | IAEATKEVQQAYLAYQQASNESQR |
| SEQ ID NO: 197 | 50 | IGGGYAGQSGAIR |

TABLE 9

Escherichia coli biomarker peptides

| SEQ ID NO | | |
|---|---|---|
| SEQ ID NO: 198 | 1 | AIDDLVKGFEELDTSK |
| SEQ ID NO: 199 | 2 | ANSSTTTAAEPLK |
| SEQ ID NO: 200 | 3 | QVPILQKDDSR |
| SEQ ID NO: 201 | 4 | VFDVNEPLSQINQAK |
| SEQ ID NO: 202 | 5 | VPVFAGDTEDDITAR |
| SEQ ID NO: 203 | 6 | SVQTVTGQPDVDQVVLDEAIKNR |
| SEQ ID NO: 204 | 7 | LIAAAPTAVAPEESGFYAR |
| SEQ ID NO: 205 | 8 | NAEFLQAYGVAIADGPLK |
| SEQ ID NO: 206 | 9 | EIAFEELGSQAR |
| SEQ ID NO: 207 | 10 | AEVPSGTVLAEKQELVR |
| SEQ ID NO: 208 | 11 | APRPAPAPQAPAQNTTPVTK |
| SEQ ID NO: 209 | 12 | RTEPAAPVASTK |
| SEQ ID NO: 210 | 13 | SDTYGWQEDSTYIR |
| SEQ ID NO: 211 | 14 | SYEEELAKDPR |
| SEQ ID NO: 212 | 15 | RTEPAAPVASTKAPAATSTPAPK |
| SEQ ID NO: 213 | 16 | ADGINPEELLGNSSAAAPR |
| SEQ ID NO: 214 | 17 | IVQSPDVIPADSEAGR |
| SEQ ID NO: 215 | 18 | MAERPEVQDALSAEGLK |
| SEQ ID NO: 216 | 19 | NAEFLQAYGVAIADGPLKGLAAR |
| SEQ ID NO: 217 | 20 | QQAEVTEKAR |
| SEQ ID NO: 218 | 21 | APAATSTPAPK |
| SEQ ID NO: 219 | 22 | AFDSQTEDSSPAIGR |
| SEQ ID NO: 220 | 23 | PNELLNSLAAVK |
| SEQ ID NO: 221 | 24 | APAKESAPAAAAPAAQPALAAR |
| SEQ ID NO: 222 | 25 | MNAFDSQTEDSSPAIGR |
| SEQ ID NO: 223 | 26 | SGDLTAFEPELLKEHNAR |
| SEQ ID NO: 224 | 27 | SLSDTLEEVLSSSGEK |
| SEQ ID NO: 225 | 28 | NIPVELHVLLNDDAETPTR |
| SEQ ID NO: 226 | 29 | QAQINGLEMAFLSAEEKR |
| SEQ ID NO: 227 | 30 | QEAAPAAAPAPAAGVK |
| SEQ ID NO: 228 | 31 | SRLPQNITLTEV |
| SEQ ID NO: 229 | 32 | HLAKAPAKESAPAAAAPAAQPALAAR |
| SEQ ID NO: 230 | 33 | LTSSTATAATSKPVTSVASGPR |
| SEQ ID NO: 231 | 34 | NVEYLVVEAAGATR |
| SEQ ID NO: 232 | 35 | SDDMSMGLPSSAGEHGVLR |
| SEQ ID NO: 233 | 36 | VRYEQSVAEEAVVAPVVEETVAAEPIVQEAPAPR |
| SEQ ID NO: 234 | 37 | AVTNSPVVVALDYHNR |
| SEQ ID NO: 235 | 38 | EAPLAVELDHDKVMNMQVK |
| SEQ ID NO: 236 | 39 | IMSGNSETETQEVGFKER |
| SEQ ID NO: 237 | 40 | KRPEQPALATFAMPDVPPAPTPAEPAAPVVAPAPK |
| SEQ ID NO: 238 | 41 | SQPIFNDKQFQEALSR |
| SEQ ID NO: 239 | 42 | ALDLSAEEKAAVR |
| SEQ ID NO: 240 | 43 | ALEKVVGLQTEAPLKR |
| SEQ ID NO: 241 | 44 | EAAIQVSNVAIFNATTGK |
| SEQ ID NO: 242 | 45 | ETATTAPVQTASPAQTTATPAAGGK |
| SEQ ID NO: 243 | 46 | FSAVLEQGAIAAGSDNK |
| SEQ ID NO: 244 | 47 | LHHANDTDSFSATNVH |
| SEQ ID NO: 245 | 48 | NVEYLVVEAAGTTR |
| SEQ ID NO: 246 | 49 | SLEHEVTLVDDTLVR |
| SEQ ID NO: 247 | 50 | TNGSLNAAEATETLR |

TABLE 10

The most prominent species-unique peptides of *S. aureus*. The corresponding Gen Bank accession numbers and descriptions of the proteins are shown.

| SEQ ID NO | Peptide sequence | Protein | |
|---|---|---|---|
| SEQ ID NO: 1 | TVQPIDVDTIVASVEK | AKJ16950.1 | 2-oxoisovalerate dehydrogenase |
| SEQ ID NO: 2 | QAGVGAAVVAELSER | | |
| SEQ ID NO: 3 | ELINNIQSGQR | AKJ17520.1 | preprotein translocase subunit YajC |
| SEQ ID NO: 4 | LGISDGDVEETEDAPK | AKJ17148.1 | recombinase RecA |
| SEQ ID NO: 5 | ALLNNMVQGVSQGYVK | AKJ18065.1 | 50S ribosomal protein L6 |
| SEQ ID NO: 6 | SNVNDATDYSSETPEGK | AKJ17216.1 | transketolase |
| SEQ ID NO: 7 | ANNVATDANHSYTSR | AKJ17623.1 | hypothetical protein |

TABLE 10-continued

The most prominent species-unique peptides of *S. aureus*. The corresponding Gen Bank accession numbers and descriptions of the proteins are shown.

| SEQ ID NO | Peptide sequence | Protein | |
|---|---|---|---|
| SEQ ID NO: 8 | ILAESPNLAISSSSR | AKJ16422.1 | HAD family hydrolase |
| SEQ ID NO: 9 | NVVEIPLNDEEQSK | AKJ16109.1 | lactate dehydrogenase |
| SEQ ID NO: 10 | ATEATNATNNQSTQVSQATSQPINFQVQK | AKJ16987.1 | heme transporter IsdA |
| SEQ ID NO: 11 | IHLVGDEIANGQGIGR | AKJ17576.1 | pyruvate kinase |
| SEQ ID NO: 12 | NISNNVLVTIDAAQGK | | |
| SEQ ID NO: 13 | TAKPVAEVESQTEVTE | AKJ16406.1 | DNA-directed RNA polymerase subunit beta' |
| SEQ ID NO: 14 | SQGVSEEELNESIDR | AKJ16022.1 | acetaldehyde dehydrogenase |
| SEQ ID NO: 15 | AEENGLTVVDAFNFEAPK | AKJ18079.1 | 50S ribosomal protein L4 |
| SEQ ID NO: 16 | EKANELLKDNAELIASFSR | AKJ18460.1 | fructose-16-bisphosphate aldolase |
| SEQ ID NO: 17 | LLGINATIVMPETAPQAK | AKJ17317.1 | threonine dehydratase |

TABLE 11

The most prominent species-unique peptides of *M. catarrhalis*. The corresponding GenBank accession numbers and descriptions of the proteins are shown.

| SEQ ID NO | Peptide sequence | Protein | |
|---|---|---|---|
| SEQ ID NO: 18 | VVLAGDTVVSDR | WP_003666427.1 | TonB-dependent receptor |
| SEQ ID NO: 19 | QIVSNAGDEASVIVNEVK | WP_063454121.1 | chaperonin GroEL |
| SEQ ID NO: 20 | AIAQVGSISANSDATIGELISK | | |
| SEQ ID NO: 21 | ELSNTAAETQPK | WP_003659702.1 | 30S ribosomal protein S1 |
| SEQ ID NO: 22 | VDATVDAQNPTK | WP_003660336.1 | hypothetical protein |
| SEQ ID NO: 23 | QSDVGQLTGK | | |
| SEQ ID NO: 24 | FNATAALGGYGSK | WP_063454085.1 | cell surface protein |
| SEQ ID NO: 25 | THTSALAEENQQASIPR | WP_063454087.1 | cell division protein FtsZ |
| SEQ ID NO: 26 | YVVEGANMPLDAQAIDIVR | WP_049156084.1 | NADP-specific glutamate dehydrogenase |
| SEQ ID NO: 27 | SQIYQTTASVSGAR | WP_003657351.1 | Ohr family peroxiredoxin |
| SEQ ID NO: 28 | LLNETTGQVVPK | WP_003657987.1 | DUF4377 domain-containing protein |
| SEQ ID NO: 29 | SSENVVVSVR | WP_063454071.1 | electron transfer flavoprotein subunit beta |
| SEQ ID NO: 30 | AISYGNSADAQPYVGAK | WP_003658939.1 | porin family protein |
| SEQ ID NO: 31 | GLPVSNSGAPISVPVGQATLGR | WP_003658974.1 | F0F1 ATP synthase subunit beta |
| SEQ ID NO: 32 | VNYNGDTDTVTLSGVAK | WP_003656943.1 | peptidoglycan-binding protein LysM |

TABLE 11-continued

The most prominent species-unique peptides of *M. catarrhalis*. The corresponding GenBank accession numbers and descriptions of the proteins are shown.

| SEQ ID NO | Peptide sequence | Protein | |
|---|---|---|---|
| SEQ ID NO: 33 | AVATQQATVSAEYLQK | WP_003657125.1 | ABC transporter substrate-binding protein |
| SEQ ID NO: 34 | ADSGLSESEIEEMIR | WP_003669031.1 | molecular chaperone DnaK |
| SEQ ID NO: 35 | LGAQEAELVSNSK | WP_003660298.1 | CTP synthase |

TABLE 12

The most prominent species-unique peptides of *H. influenzae*. The corresponding GenBank accession numbers and descriptions of the proteins are shown.

| SEQ ID NO | Peptide sequence | Protein | |
|---|---|---|---|
| SEQ ID NO: 36 | GVAADAISATGYGK | WP_038441355.1 | porin OmpA |
| SEQ ID NO: 37 | ANLKPQAQATLDSIYGEMSQVK | | |
| SEQ ID NO: 38 | ADSVANYFVAK | | |
| SEQ ID NO: 39 | GSYEVLDGLDVYGK | | |
| SEQ ID NO: 40 | LSQERADSVANYFVAK | | |
| SEQ ID NO: 41 | AVVYNNEGTNVELGGR | WP_058222193.1 | porin |
| SEQ ID NO: 42 | YDANNIIAGIAYGR | | |
| SEQ ID NO: 43 | ATHNFGDGFYAQGYLETR | | |
| SEQ ID NO: 44 | AVVYNNEGTKVELGGR | | |
| SEQ ID NO: 45 | QQVNGALSTLGYR | | |
| SEQ ID NO: 46 | YVPTNGNTVGYTFK | | |
| SEQ ID NO: 47 | LSVIAEQSNSTR | | |
| SEQ ID NO: 48 | SADLTNEVAVGDVVEAK | WP_011272719.1 | 30S ribosomal protein S1 |
| SEQ ID NO: 49 | SADLTSEVAVGDVVEAK | | |
| SEQ ID NO: 50 | TSPTQNLSLDAFVAR | WP_058222202.1 WP_050846043.1 | ShlB/FhaC/HecB family hemolysin secretion/activation protein |
| SEQ ID NO: 51 | AQYIVEQVIGQAR | WP_011272712.1 | pyruvate dehydrogenase (acetyl-transferring), homodimeric type |

TABLE 13

The most prominent species-unique peptides of *S. pneumoniae*. The corresponding GenBank accession numbers and descriptions of the proteins are shown.

| SEQ ID NO | Peptide sequence | Protein | |
|---|---|---|---|
| SEQ ID NO: 52 | VSDVAESTGEFTSEQFEK | WP_000064115.1 | Asp23/Gls24 family envelope stress response protein |
| SEQ ID NO: 53 | GAANGVVSHENTR | | |
| SEQ ID NO: 54 | EEAPVASQSK | WP_001035310.1 | hypothetical protein |
| SEQ ID NO: 55 | SADQQAEEDYAR | | |
| SEQ ID NO: 56 | APLQSELDTK | | |
| SEQ ID NO: 57 | LKEIDESDSEDYVK | | |
| SEQ ID NO: 58 | AKLEEAEKKATEAK | | |
| SEQ ID NO: 59 | AVNEPEKPAEESENPAPAPK | | |

TABLE 13-continued

The most prominent species-unique peptides of *S. pneumoniae*. The corresponding GenBank accession numbers and descriptions of the proteins are shown.

| SEQ ID NO | Peptide sequence | Protein | |
|---|---|---|---|
| SEQ ID NO: 60 | NVEIIEDDKQGVIR | WP_000245505.1 | 30S ribosomal protein S8 |
| SEQ ID NO: 61 | NLPVGSDGTFTPEDYVGR | WP_001291372.1 | methionine--tRNA ligase |
| SEQ ID NO: 62 | TLELEIAESDVK | WP_000458177.1 | hypothetical protein |
| SEQ ID NO: 63 | DIGLANDGSIVGINYAK | WP_000927809.1 | sugar ABC transporter substrate-binding protein |
| SEQ ID NO: 64 | IAELEYEVQR | WP_001008677.1 | Asp-tRNA(Asn)/Glu-tRNA(Gln) amidotransferase subunit GatB |
| SEQ ID NO: 65 | AVAAADAADAGAAK | WP_001196960.1 | 50S ribosomal protein L7/L12 |
| SEQ ID NO: 66 | GQDWVIAAEVVTKPEVK | WP_000116461.1 | trigger factor |
| SEQ ID NO: 67 | TLSPEEYAVTQENQTER | WP_000998307.1 | peptide-methionine (R)-S-oxide reductase |
| SEQ ID NO: 68 | KDEAEAAFATIR | WP_001284361.1 | thiol-activated toxin pneumolysin |
| SEQ ID NO: 69 | SQPSSETELSGNKQEQER | WP_078148305.1 | sialidase |
| SEQ ID NO: 70 | IGVISVVEDGDEALAK | WP_000808063.1 | elongation factor Ts |
| SEQ ID NO: 71 | VAYFNEIDTYSEVK | WP_000685088.1 | nucleotide sugar dehydrogenase |

TABLE 14

The five most prominent species-unique peptides of *S. aureus*. The corresponding GenBank accession numbers and descriptions of the proteins are shown.

| TVQPIDVDTIVASVEK | SEQ ID NO: 1 | AKJ16950.1 | 2-oxoisovalerate dehydrogenase |
| QAGVGAAVVAELSER | SEQ ID NO: 2 | | |
| ELINNIQSGQR | SEQ ID NO: 3 | AKJ17520.1 | preprotein translocase subunit YajC |
| LGISDGDVEETEDAPK | SEQ ID NO: 4 | AKJ17148.1 | recombinase RecA |
| ALLNNMVQGVSQGYVK | SEQ ID NO: 5 | AKJ18065.1 | 50S ribosomal protein L6 |

TABLE 15

The five most prominent species-unique peptides of *M. catarrhalis*. The corresponding GenBank accession numbers and descriptions of the proteins are shown.

| VVLAGDTVVSDR | SEQ ID NO: 18 | WP_003666427.1 | TonB-dependent receptor |
| QIVSNAGDEASVIVNEVK | SEQ ID NO: 19 | WP_063454121.1 | chaperonin GroEL |
| AIAQVGSISANSDATIGELISK | SEQ ID NO: 20 | | |
| ELSNTAAETQPK | SEQ ID NO: 21 | WP_003659702.1 | 30S ribosomal protein S1 |
| VDATVDAQNPTK | SEQ ID NO: 22 | WP_003660336.1 | hypothetdol protein |

TABLE 16

The five most prominent species-unique peptides of *H. influenzae*. The corresponding GenBank accession numbers and descriptions of the proteins are shown.

| | | | |
|---|---|---|---|
| GVAADAISATGYGK | SEQ ID NO: 36 | WP_038441355.1 | porin OmpA |
| ANLKPQAQATLDSIYGEMSQVK | SEQ ID NO: 37 | | |
| AWYNNEGTNVELGGR | SEQ ID NO: 41 | WP_058222193.1 | porin |
| YDANNIIAGIAYGR | SEQ ID NO: 42 | | |
| SADLTNEVAVGDVVEAK | SEQ ID NO: 48 | WP_011272719.1 | 30S ribosomal protein S1 |

TABLE 17

The five most prominent species-unique peptides of *S. pneumoniae*. The corresponding GenBank accession numbers and descriptions of the proteins are shown.

| | | | |
|---|---|---|---|
| VSDVAESTGEFTSEQFEK | SEQ ID NO: 52 | WP_000064115.1 | Asp23/Gls24 family envelope stress response protein |
| GAANGVVSHENTR | SEQ ID NO: 53 | | |
| EEAPVASQSK | SEQ ID NO: 54 | WP_001035310.1 | hypothetical protein |
| SADQQAEEDYAR | SEQ ID NO: 55 | | |
| NVEIIEDDKQGVIR | SEQ ID NO: 60 | WP_000245505.1 | 30S ribosomal protein S8 |

EXAMPLES

Examples 1—Biomarker Identification

In order to identify candidate peptide biomarkers, several strains from each of the four target species, *H. influenzae, M. catarrhalis, S. pneumonia*, and *S. aureus*, including the Type strain of each species, were selected to represent the genetic variability within the species (Table 1). Bacterial cells were grown, washed and prepared by bead beating as described in the examples and methods (FIG. 1).

Digestion of bacterial lysates and generation of peptides was performed using the Lipid-based Protein Immobilization (LPI) methodology. Peptides were analyzed by LC-MS/MS and subsequently, the tandem mass spectra were processed by a bioinformatics pipeline, TCUP, to discover species unique peptides, also described in the examples and methods. For *S. pneumoniae* 7 strains were analyzed in triplicate (21 MS runs), resulting in 782 species unique peptide candidates found in at least one of the 21 MS runs. For *H. influenzae* 9 strains were analyzed in triplicate (26 MS runs; 1 run failed), resulting in 2978 species unique peptide candidates found in at least one of the 26 MS runs. For *M. catarrhalis* 11 strains were analyzed in triplicate (33 MS runs), resulting in 5810 species unique peptide candidates found in at least one of the 33 MS runs. For *S. aureus* 13 strains were analyzed in triplicate (36 MS runs; 3 runs failed), resulting in 5847 species unique peptide candidates found in at least one of the 36 MS runs. From the sum of these species unique peptides, a targeted database containing 15417 peptides were created.

The peptides within this database were ranked according to frequency of detection to generate a preliminary inclusion list (see FIG. 1).

The preliminary inclusion list was experimentally verified as set out below.

In order to find biomarkers which were being expressed in sufficient amounts as well as being detected most easily by the mass spectrometer, different ranges of numbers of cells per ml were spiked to negative clinical samples. Thus, spiked negative samples were used to evaluate which peptides should be included in an inclusion list (50 to 100 peptides per species). Negative samples were spiked with a range of cells, ranging from 1 million cells per ml down to 100 cells per ml.

Removal of human biomass was performed by use of the MolYsis kit (Molzym, Germany) and in-solution digestion was performed using sodium deoxycholate (SDC), also described in the enclosed examples and methods. The samples were analysed via tandem MS and the tandem mass spectra were processed by a bioinformatics pipeline, TCUP, using the targeted database of mentioned above (15417 peptides) or via an open, non-targeted approach.

The peptides found in the most diluted spiked samples were considered to be promising as peptide biomarker candidates, due to a sufficient expression level and suitable properties for ionization, fragmentation and detection in the mass spectrometer (FIG. 2 and Table 2). On this basis, 100 peptides were selected as good candidate peptides per species, creating a revised inclusion list per species. Each inclusion list contained about 100 peptides and was divided into two lists of 50 for ease of handling.

In the next step of the process, true positive clinical samples were analysed to verify/revise the inclusion lists (FIG. 3). As before, removal of human biomass was performed by use of the MolYsis kit (Molzym, Germany), bacteria were lyzed using bead beating and in-solution digestion was performed using sodium deoxycholate (SDC), again described in the enclosed examples and methods. The clinical samples were analyzed using both an open approach (running all the raw files through TCUP) and a targeted approach (matching the raw data against the inclusion lists and/or targeted database mentioned above, 15417 peptides). The benefit of the open approach is that it is not targeted and thus peptides not present in the targeted database (15417 peptides) can be detected, whereas the drawback is lesser sensitivity. The benefit of the targeted approach is a higher sensitivity, but the drawback lies in the greater risk of false positives.

Approximately 1600 MS analyses were carried out, including on approximately 500 clinical samples containing *S. pneumoniae, H. influenzae, M. catarrhalis* and *S. aureus*

(as determined by traditional culture-dependent methods, including MALDI-TOF MS-based identification). This analysis was used to validate (or invalidate, as the case may be) the candidate peptide biomarkers in the inclusion lists mentioned above.

The inclusion lists were revised as follows (see FIG. 3): If any peptide biomarkers identified in the true positive clinical samples were already present in the inclusion lists, this validated their relevance. If any peptide biomarkers present in the inclusion lists were not detected in any of the true positive clinical samples, they were removed from the inclusion lists, or were given a lower ranking.

If any peptide biomarkers that were not present in the inclusion list, but were present in the targeted database (15417 peptides), were identified in the true positive clinical samples, their ranking was noted and they were then included in an updated inclusion list.

Some peptides were ranked low in the first run based on bacterial cultures, e.g. found only in 1 out of 21 MS runs (in case of S. pneumoniae), but were nevertheless found in all clinical samples. This was likely due to different expression levels in the blood agar cultures as compared to actual clinical samples. For example, a virulence factor might be highly expressed in a clinical sample, whereas it is only moderately expressed in a blood agar culture.

The same strategy also is also being used to generate a peptide biomarker inclusion list for E. coli.

Some peptides were also selected for PRM studies (FIGS. 5 and 7). Parallel reaction monitoring (PRM) is an ion monitoring technique based on high-resolution and high-precision mass spectrometry. The principle of this technique is comparable to SRM/MRM, but it is more convenient in assay development for absolute quantification of proteins and peptides. It is most suitable for quantification of multiple proteins in complex sample with an attomole-level detection. PRM is based on Q-Orbitrap as the representative quadrupole-high resolution mass spectrum platform. Unlike the SRM, which performs one transition at a time, the PRM performs a full scan of each transition by a precursor ion, that is, parallel monitoring of all fragments from the precursor ion. First, the PRM uses the quadrupole (Q1) to select the precursor ion, and the selection window is usually m/z≤2; then, the precursor ion is fragmented in the collision cell (Q2); finally, Orbitrap replaces Q3, scans all product ions with high resolution and high accuracy. Therefore, PRM technology not only has the SRM/MRM target quantitative analysis capabilities, but also have the qualitative ability. (1) The mass accuracy can reach to ppm level, which can eliminate the background interference and false positive better than SRM/MRM, and improve the detection limit and sensitivity in complex background effectively; (2) Full scan of product ions, without the need to select the ion pair and optimize the fragmentation energy, easier to establish the assay; (3) a wider linear range: increased to 5-6 orders of magnitude. Using this approach, it was possible to verify the presence of a biomarker peptide in a clinical sample by observing the same retention time and the same set of fragment ions when comparing to an analysis of a bacterial culture containing the same peptide.

Methods:
Cultivation of Bacteria and Preparation of Samples

In order to generate lists of candidate peptide biomarkers, approximately ten strains from each of the four target species, H. influenzae, M. catarrhalis, S. pneumoniae and S. aureus, including the Type strain of each species, were selected to represent the genetic variability within the species (Table 1).

Bacterial strains were grown on Blood Agar medium. S. pneumoniae and M. catarrhalis were grown at 36° C. with 5% CO2 overnight, S. aureus at 37° C. overnight, and H. influenzae was grown on chocolate agar medium at the same conditions as S. pneumoniae and M. catarrhalis. Bacterial biomass was collected and resuspended in phosphate-buffered saline (PBS). Bacterial densities were measured at A600 (A600=1 corresponding to $1*10^9$ bacteria). For each experiment, the same amounts of bacterial biomass were established, by adjusting the A to 1.0 in 1.0 ml of PBS. The bacterial biomass was washed with PBS three times by centrifuging the sample for 5 min at 12,000 g, discarding the supernatant, and resuspending the pellet in 1.0 ml of PBS. The bacteria were finally resuspended in 150 µl of PBS. The bacterial cell suspensions were transferred to 200-µl vials containing glass beads (Sigma-Aldrich, G1145). The bacterial cells were lysed by bead-beating, using a TissueLyser (Qiagen, 85220), with the following settings: frequency 1/25 s and 5 min. The bacterial lysates were frozen at −20° C. until analysis.

Spiking of Negative Samples for Discovery of Candidate Peptide Biomarkers

Clinical samples (respiratory tract nasopharyngeal and nasal swabs) deemed negative by culture and MALDI-TOF-MS were collected and spiked with cells of the Type strains of the four species H. influenzae, M. catarrhalis, S. pneumoniae and S. aureus. The spikes of added cells ranged from 1 million cells/ml down to 100 cells/ml.

Clinical Sample Clean-Up Using MolYsis Kit

The clinical samples (respiratory tract nasopharyngeal and nasal swabs), collected in Amies media, were supplemented with STGG (Skim milk, tryptone, glucose, glycerol) and frozen until processing.

For removal of human biomass (mucus, cells and proteins), the MolYsis kit (MolYsis Basic5 kit, Molzym, Germany) was used according to protocol provided by the supplier. The biomass was collected by centrifuging the samples 15000 g (5 min) in 1.5 ml Eppendorf tubes. Supernatant was discarded. The pellet was resuspended in 1 ml (500 µl SU buffer+500 µl PBS). CM buffer (250 µl) was added and the sample was vortexed for 15 s and then allowed to stand at room temp for 10 min. The samples were transferred to 2.0 ml tubes. If visible clusters of bacteria/mucus were present the sample was pipetted up and down until they were dissolved. DB1 buffer (250 µl) was added and the sample was vortexed before allowing standing at room temp for 15 min. If visible clusters of bacteria/mucus were present the sample was pipetted up and down until dissolving. The sample was centrifuged—15000 g for 10 min to collect bacteria. Supernatant discarded and pellet saved. Pellet was resuspended in 1 ml RS buffer.

The sample was centrifuged—15000 g for 5 min to collect bacteria. Supernatant discarded and pellet saved. Pellet was resuspended in 1 ml PBS buffer. The sample was centrifuged—15000 g for 5 min to collect bacteria. Supernatant discarded and pellet saved. Supernatant was discarded and the bacteria were resuspended in 120 µl ammonium bicarbonate (20 mM pH 8). The sample was subjected to bead beating in order to break the cells and release as many proteins as possible, making them accessible for digestion. Glass beads (Sigma-Aldrich G1145) had already been placed in the vials. The bead beater used was a TissueLyser from Qiagen. Settings: Frequency 1/25 s and continuous shaking for a total time of 5 min. The bead beaten samples were frozen until analysis.

Digestion of Clinical Samples Using In-Solution Digestion with Sodium Deoxycholate (SDC)

Frozen samples where thawed. SDC 1% was added from a 5% stock and bead beating was repeated. Samples were removed from the glass beads and transferred to new tubes (1.5 ml). The remaining glass beads were rinsed by adding 100 µl 1% SDC in ammonium bicarbonate (20 mM) and transferred to the samples. Trypsin (2 µg/ml, 100 µl ammonium bicarbonate, 20 mM pH 8) was added and samples were allowed to be digested for 8 h at 37 degrees Celsius. Formic acid (3 µl, neat) was subsequently added to remove SDC. Samples were centrifuged at 15000 g (10 min) to pellet biomass/debris. Pellet was discarded and supernatant (peptides) was transferred to a new tube (1.5 ml). Samples were kept frozen at −20 degrees Celsius until analysis.

Peptide Analysis Using Tandem Mass Spectrometry

The tryptic peptides were desalted on Pep Clean C18 spin columns (Thermo Fisher Scientific, Inc., Waltham, Mass.), according to the manufacturer's guidelines, dried, and reconstituted with 15 µl of 0.1% formic acid (Sigma-Aldrich) in 3% gradient-grade acetonitrile (Merck KGaA, Darmstadt, Germany). A 2.0 µl sample was injected, with an Easy-nLC autosampler (Thermo Fisher Scientific), and analyzed, using an interfaced Q Exactive hybrid mass spectrometer (Thermo Fisher Scientific). The peptides were trapped on a pre-column (45µ 0.075-mm inner diameter) and separated on a reversed-phase column, 200 0.075 mm, packed in-house with 3-m Reprosil-Pur C18-AQ particles (Dr. Maisch, Ammerbuch, Germany). The nanoLC (liquid chromatography) gradient was running at 200 nl/min, starting at 7% acetonitrile (ACN) in 0.2% formic acid, increased to 27% CAN for 25 min, then increased to 40% ACN for 5 min, and finally to 80% ACN for 5 min and held at 80% ACN for 10 min. Electrospray ionization was applied under a voltage of 1.8 kV and a capillary temperature of 320° C. in data-dependent positive ion mode. Full scan (MS1) spectra were acquired in the Orbitrap over the m/z range 400-1600, with a charge range of 2-6, at a resolution of 70,000, until reaching an AGC target value of 1e6 at a maximum of 250 ms. MS/MS spectra were acquired, using higher energy collision dissociation, at 30% from m/z 110 for the 10 most abundant parent ions, at a resolution of 35,000, using a precursor isolation window of 2 Da until reaching an AGC target value of 1e5 during an injection time of 110 ms. Dynamic exclusion for 30 s after selection for MS/MS was enabled to allow for detection of as many precursors as possible.

TCUP—Typing and Characterization Using Proteomics

The input to TCUP is a set of peptides identified from spectra generated by bottom-up tandem MS specified as a file in FASTA format. TCUP is general and can be used with peptide data from any spectral matching software, including de novo methods (e.g. SEQUEST (18), X!Tandem (19, 20), TIDE (21), Mascot (22), PEAKS (23), PepNovo (24), and Lutefisk (25)). The output from TCUP is in Excel format and includes the following: 1) the relative abundances of all organisms identified in a sample at and below a user-specified taxonomic level; 2) specific genes in the reference genomes that are matched by peptides in the analysis; and 3) the relative abundances of identified antimicrobial resistance genes. TCUP is implemented in Python 3.5, and the code and usage documentation are freely available under the ISC license from the project's repository. After alignment to the translated reference genome sequences, each peptide is matched to zero, one, or multiple reference genomes. To remove matches that are too dissimilar and unlikely to contain any relevant information about the taxonomic affiliation, two filtering steps were applied. The first step requires matches to have an identity of at least 90% and a coverage of 100% (only complete peptide matches are considered). Also, peptides shorter than six amino acids are removed. In the second filtering step, all matches with sequence identity of at least 5% below the best match for that peptide are discarded.

After filtering, the remaining peptides are assigned to nodes in a taxonomic tree, using the lowest common ancestor algorithm (30). The taxonomic affiliation of a sample is then assigned based on the set of discriminative peptides, i.e. the peptides with a lowest common ancestor at a node that is at or below the user-specified taxonomic level. The taxonomic tree used in TCUP is based on the full NCBI Taxonomy (31) (taxdump downloaded Nov. 17, 2015), in which each reference genome is associated with a unique node. Our implementation extends the SQLite3 database used in the ETE3 package (32) with a table of taxonomic affiliations for all reference genome sequences included in the reference database.

Example 2—Detection of *S. Pneumoniae* Through Detection of Peptide Biomarkers in a Clinical Sample Step 1. Ten respiratory tract samples (nasopharyngeal swabs) deemed positive for *S. Pneumoniae* by traditional methods, including culturing and isolation of bacterial isolates, followed by MALDI-TOF-MS identification, were selected. The samples were in the form of swabs in commercial Amies media (Copan Diagnostics Inc).

Step 2. 50% of the liquid Amies media (0.5 ml) was transferred to a cryotube and supplemented with STGG buffer (Skim milk, tryptone, glucose, glycerol) for storage at −20 degrees Celsius until analysis.

Step 3. Human biomass was removed from the sample using the MolYsis kit (Molzym Gbh, Germany), according to manufacturer's protocol.

Step 4. Sample was homogenized using bead beating and subsequently, the bacterial proteins were digested into peptides using trypsin in a buffer supplemented with sodium deoxycholate (SDC).

Step 5. The peptides were desalted and purified using C18 spin column clean-up. After drying in speedvac, the peptides were resuspended in dilute formic acid.

Step 6. The peptides were analyzed using LC-MS/MS, using the inclusion lists in a mode called inclusion list plus pick others. In this fashion were the MS instrument first looks only at the masses of the selected peptides in the inclusion list. If there are no masses matching to the 50 peptides in the inclusion list during the MS instrument cycle time (milliseconds), the instrument looks for everything else and picks the top ten most intense ion peaks (pick others).

Step 7. The raw files were run through TCUP to match, identify and report the peptides identified in the samples. The results from this analysis are shown in Table 3. Thirteen peptides were identified belonging to the inclusion list among the ten clinical samples, thus resulting in a positive match for *S. Pneumoniae*.

Example 3—Example Showing a Panel of the Peptide Biomarkers for Performing Clinical Diagnostics Table 18 below shows an exemplary panel of the peptide biomarkers proposed for use in performing clinical diagnostics. Five different samples containing one or more of the four pathogens are analyzed. In each sample, a particular combination of the peptide biomarkers (shown by SEQ ID NOs) is shown. The detection of the peptide biomarkers are detected by any of the suggested methodologies, i.e. targeted MS approaches, or based on antibody detection or other suitable methodologies.

|  | S. aureus | M. catarrhalis | H. influenzae | S. pneumoniae |
|---|---|---|---|---|
| Sample 1 | SEQ ID NO: 1 |  |  |  |
| S. aureus | SEQ ID NO: 2 |  |  |  |
| Sample 2 |  | SEQ ID NO: 20 | SEQ ID NO: 36 |  |
| M. catarrhalis |  | SEQ ID NO: 21 | SEQ ID NO: 37 |  |
| H. influence |  | SEQ ID NO: 22 | SEQ ID NO: 41 |  |
|  |  |  | SEQ ID NO: 42 |  |
| Sample 3 |  | SEQ ID NO: 18 |  | SEQ ID NO: 52 |
| M catarrhalis |  | SEQ ID NO: 19 |  | SEQ ID NO: 53 |
| S. pneumoniae |  | SEQ ID NO: 20 |  | SEQ ID NO: 54 |
|  |  |  |  | SEQ ID NO: 55 |
| Sample 4 |  |  | SEQ ID NO: 41 | SEQ ID NO: 54 |
| H. influence |  |  | SEQ ID NO: 42 | SEQ ID NO: 55 |
| S. pneumoniae |  |  | SEQ ID NO: 48 | SEQ ID NO: 60 |
| Sample 5 |  |  |  | SEQ ID NO: 52 |
| S. pneumoniae |  |  |  | SEQ ID NO: 55 |

The invention claimed is:

1. A non-naturally occurring set of peptides comprising 2-50 different peptides,
   wherein at least two peptides of the 2-50 different peptides are desalted and wherein the at least two peptides of the 2-50 different peptides consist of an amino acid sequence selected from one of the following groups:
   (i) SEQ ID NOs:52-71 and 168-197;
   (ii) SEQ ID NOs:36-51 and 104-135;
   (iii) SEQ ID NOs:1-17, 136-167, and 248;
   (iv) SEQ ID NOs:18-35 and 72-103;
   (v) SEQ ID NOs:198-247;
   (vi) SEQ ID NOs:52-71;
   (vii) SEQ ID NOs:36-51;
   (viii) SEQ ID NOs:1-17;
   (ix) SEQ ID NOs:18-35
   (x) SEQ ID NOs:19, 36, 41, 42, 47, 52, 53, 249-268; or
   (xi) SEQ ID NOs:52, 60, 61, 171, 174, 181, 185, 269-274.

2. The non-naturally occurring set of peptides according to claim 1, wherein the at least two peptides of the 2-50 different peptides consist of an amino acid sequence selected from one of the following groups:
   (i) SEQ ID NOs:52-55 and 60;
   (ii) SEQ ID NOs:36, 37, 41, 42, and 48;
   (iii) SEQ ID NOs:1-5; or
   (iv) SEQ ID NOs:18-22.

3. A method of detecting or identifying a bacterial biomarker in a sample, the method comprising: detecting in the sample at least one desalted peptide of the non-naturally occurring set of peptides of claim 1.

4. The method according to claim 3, wherein the method is
   used to detect or identify one of *Streptococcus pneumoniae*, *Staphylococcus aureus*, *Haemophilus influenzae*, *Escherichia coli*, and *Moraxella catarrhalis*.

5. The method of claim 3, wherein said method is used to detect or identify two or more bacteria selected from *Streptococcus pneumoniae*, *Staphylococcus aureus*, *Haemophilus influenzae*, *Escherichia coli*, and *Moraxella catarrhalis* in the sample.

6. The method of claim 3, wherein the detecting comprises detecting at least two desalted peptides in the non-naturally occurring set of peptides.

7. The method of claim 3, wherein the detecting is carried out using mass spectrometry and/or an affinity reagent specific for the biomarker.

8. The method of claim 3, further comprising, prior to the detecting step, a cell lysis step and/or a proteolysis step.

9. The method of claim 3, further comprising, responsive to detecting in the sample the at least one desalted peptide, diagnosing bacterial infection.

10. A diagnostic kit for detecting specific biomarker peptides in a sample, wherein the kit comprises the non-naturally occurring set of peptides according to claim 1, wherein the kit further comprises a protease.

11. A non-naturally occurring peptide having an amino acid sequence consisting of one of SEQ ID NOs:1-71, wherein the non-naturally occurring peptide is desalted.

12. The non-naturally occurring peptide of claim 11, wherein the non-naturally occurring peptide has an amino acid sequence consisting of one of SEQ ID NOs:1-5, 18-22, 36, 37, 41, 42, 48, 52-55 and 60.

13. A pharmaceutical composition comprising the non-naturally occurring peptide according to claim 11.

* * * * *

UNITED STATES PATENT AND TRADEMARK OFFICE
CERTIFICATE OF CORRECTION

| | | |
|---|---|---|
| PATENT NO. | : 11,740,237 B2 | Page 1 of 1 |
| APPLICATION NO. | : 17/052731 | |
| DATED | : August 29, 2023 | |
| INVENTOR(S) | : Karlsson et al. | |

It is certified that error appears in the above-identified patent and that said Letters Patent is hereby corrected as shown below:

In the Specification

Column 9, Line 59: Please correct "thereof, preferably as" to read --thereof, preferably as defined below,--

Column 11, Line 25: Please correct "thereof, preferably as" to read --thereof, preferably as defined below,--

Columns 39-40, Table 15: Please delete and replace with the following:
Table 15 The five most prominent species-unique peptides of *M. calarrhalis*. The corresponding GenBank accession numbers and descriptions of the proteins are shown.

| VVLAGDTVVSDR | SEQ ID NO:18 | WP_003666427.1 | TonB-dependent receptor |
|---|---|---|---|
| QIVSNAGDEASVIVNEVK | SEQ ID NO:19 | WP_063454121.1 | chaperonin GroEL |
| AIAQVGSISANSDATIGELISK | SEQ ID NO:20 | | |
| ELSNTAAETQPK | SEQ ID NO:21 | WP_003659702.1 | 30S ribosomal protein S1 |
| VDATVDAQNPTK | SEQ ID NO:22 | WP_003660336.1 | hypothetical protein |

Signed and Sealed this
Thirteenth Day of February, 2024

*Katherine Kelly Vidal*

Katherine Kelly Vidal
*Director of the United States Patent and Trademark Office*